Figure 1:
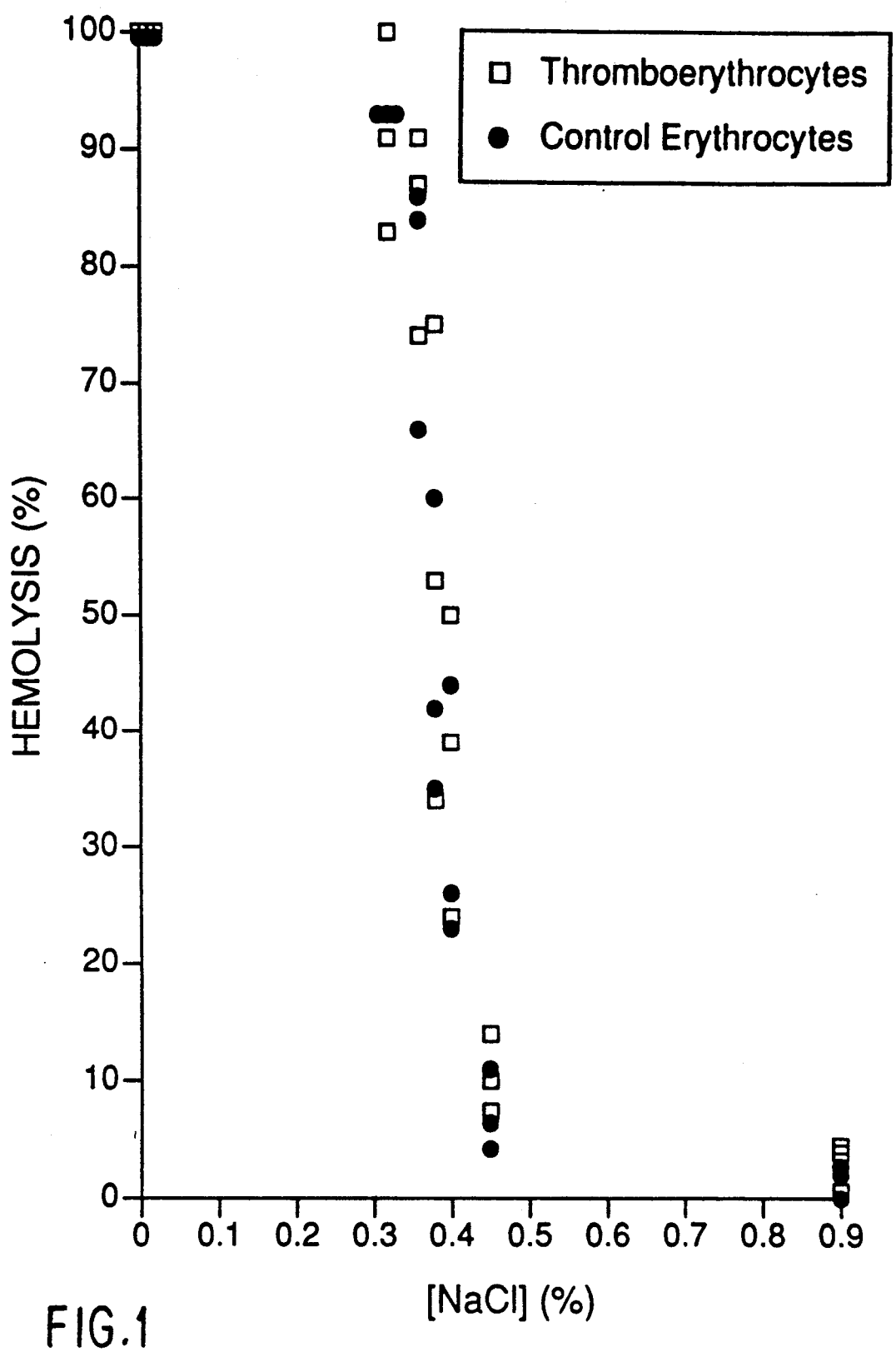

United States Patent [19]
Coller

[11] Patent Number: 5,328,840
[45] Date of Patent: Jul. 12, 1994

[54] METHOD FOR PREPARING TARGETED CARRIER ERYTHROCYTES

[75] Inventor: Barry S. Coller, Dix Hills, N.Y.

[73] Assignee: The Research Foundation of the State University of New York, Albany, N.Y.

[21] Appl. No.: 790,851

[22] Filed: Nov. 12, 1991

Related U.S. Application Data

[63] Continuation-in-part of Ser. No. 611,164, Nov. 9, 1990, abandoned, which is a continuation-in-part of Ser. No. 394,018, Aug. 15, 1989, abandoned.

[51] Int. Cl.$^5$ .................. C12N 5/00; C12N 11/08; A61K 37/02; A61K 37/00
[52] U.S. Cl. ........................ 435/240.2; 435/240.1; 435/240.23; 435/240.243; 435/70.21; 435/180; 435/181; 514/2; 530/300; 530/350
[58] Field of Search ............. 435/240.1, 240.2, 240.23, 435/240.243, 4, 180, 181, 300, 70.21; 530/350, 351, 387, 388, 829, 810, 811, 812; 424/85.8; 514/2

[56] References Cited

U.S. PATENT DOCUMENTS

| | | |
|---|---|---|
| 4,244,946 | 1/1981 | Rivier et al. |
| 4,305,872 | 12/1981 | Johnston et al. |
| 4,316,891 | 2/1982 | Guillemin et al. |
| 4,517,686 | 5/1985 | Ruoslahti et al. |
| 4,578,079 | 3/1986 | Ruoslahti et al. |
| 4,589,881 | 5/1986 | Pierschbacher et al. |
| 4,614,517 | 9/1986 | Ruoslahti et al. |
| 4,661,111 | 4/1987 | Ruoslahti et al. |
| 4,789,734 | 12/1988 | Pierschbacher . |
| 4,792,525 | 12/1988 | Ruoslahti et al. |
| 4,857,508 | 8/1989 | Adams et al. |
| 4,988,621 | 1/1991 | Ruoslahti et al. |

OTHER PUBLICATIONS

Caulfield et al., 1984, "The 64-kilodalton membrane protein of *Bacillus subtilis* is also present as a multiprotein complex on membrane-free ribosomes," Proc. Natl. Acad. Sci. USA 81:7772-7776.

Coller et al., 1990, "Thromboerythrocytes: preliminary in vitro attempts to develop a semi-artificial, autologous platelet (P) substitute," Circulation, Suppl. III., 82(4), Abstract 2377.

Coller, 1980 "Interaction of normal, thrombasthenic, and Bernard-Soulier platelets with immobilized fibrinogen: defective platelet-fibrinogen interaction in thrombasthenia," Blood 55:169-178.

Cumber et al., 1985, "Preparation of antibody-toxin conjugates," Meth. Enzymol. 112:207-225.

*Primary Examiner*—Robert J. Hill, Jr.
*Assistant Examiner*—Gian P. Wang
*Attorney, Agent, or Firm*—Pennie & Edmonds

[57] ABSTRACT

The present invention provides new compounds and methods for promoting platelet aggregation, and controlling bleeding. The present invention is based on the surprising discovery that erythrocytes conjugated to certain peptides and polypeptides containing an R-G-D (Arg-Gly-Asp) sequence (collectively termed herein "RGD peptides") according to the invention, selectively bind to activated platelets but not to unactivated platelets. In recognition of the dual nature of the derivatized erythrocytes, they are termed herein "thromboerythrocytes". The thrombo-erythrocytes have no significant change in their rheological properties. In a preferred aspect, the thrombo-erythrocytes have the majority of RGD peptide cross-linked specifically to glycophorin A and glycophorin B on the surface of the erythrocyte. In the thrombo-erythrocytes of the invention, preferably, the N-terminal Arg of the R-G-D sequence should be spaced within 9-50 Angstroms, more preferably 10-40 Angstroms, and most preferably 11-25 Angstroms, from the erythrocyte protein to which the RGD peptide is conjugated. The invention is further directed to erthrocytes modified by replacement of their intracellular contents with a composition comprising a label or agent. Such modified erythrocytes are termed herein "carrier erythrocytes". The carrier erythrocytes have use in delivery of such labels or biologically active agents to specific tissues by conjugation 20 Claims, 23 Drawing Sheets

OTHER PUBLICATIONS

Hamada and Tsuruo, 1987, "Determination of membrane antigens by a covalent crosslinking method with monoclonal antibodies," Anal. Biochem. 160:483–488.

Lerner et al., 1981, "Chemically synthesized peptides predicted from the nucleotide sequence of the hepatitis B virus genome elicit antibodies reactive with the native envelope protein of Dane particles," Proc. Natl. Acad. Sci. USA 78:3403–3407.

Merrifield, 1964, "Solid phase peptide synthesis. II. The synthesis of bradykinin," J. Am. Chem. Soc. 83:304–305.

Merrifield, 1964, "Solid phase synthesis. I. The synthesis of a tetrapeptide," J. Am. Chem. Soc. 85:2149–2154.

Pilch and Czech, 1979, "Interaction of cross-linking agents with the insulin effector system of isolated fat cells," J. Biol. Chem. 254:3375–3381.

Plow et al., 1987, "Arginyl-glycyl-aspartic acid sequences and fibrinogen binding to platelets", Blood 70:110–115.

Sun et al., 1974, "Topography of ribosomal proteins of the *Escherichia coli* 30S subunit as studied with the reversible cross-linking reagent methyl 4-mercaptobutyrimidate," Biochemistry 13:2334–2340.

Vale et al., 1981, "Characterization of a 41-residue ovine hypothalamic peptide that stimulates secretion of croticotropin and β-endorphin," Science 213:1394–1397.

Yoshitake et al., 1982, "Mild and efficient conjugation of rabbit Fab' and horseradish peroxidase using a maleimide compound and its use for enzyme immunoassay," J. Biochem. 92:1413–1424.

Youle and Neville, 1980, "Anti-Thy 1.2 monoclonal antibody linked to ricin is a potent cell-type-specific toxin," Proc. Natl. Acad. Sci. USA 77:5483–5486.

1984, "*Red Blood Cells as Carriers for Drugs. A Method for Disseminating Chemotherapeutics, Hormones, Enzymes and Other Therapeutic Agents via the Circulatory System,*" De Loach and Sprangel, eds., First International Conference on Red Blood Cell Carriers at the Rockefeller Foundation Bellagio Study and Conference Center, Bellagio (Italy), Feb. 27–Mar. 2, 1984, Table of Contents.

1987, *Red Blood Cells as Carriers for Drugs. Potential Therapeutic Applications*, Ropars et al., eds., Pergamon Press, Oxford, Great Britain, Table of Contents and Forward, pp. v–x.

Alpar and Irwin, 1987, "Some unique applications of erythrocytes as carrier systems," in *Red Blood Cells as Carriers for Drugs. Potential Therapeutic Applications*, Ropars et al., eds., Pergamon Press, Oxford, Great Britain, pp. 1–9.

DeLoach et al., 1977, "Effect of glutaraldehyde treatment on enzyme-loaded erythrocytes," Biochim. et Biophys. Acta 496:507–515.

DeLoach et al., 1985, "Carrier erythrocytes: a prospectus for the future," in *Red Blood Cells as Carriers for Drugs. A Method for Disseminating Chemotherapeutics, Hormones, Enzymes and Other Therapeutic Agents via the Circulatory System*, DeLoach and Sprangel, eds., First International Conference on Red Blood Cell Carriers at the Rockefeller Foundation Bellagio Study and Conference Center, Bellagio (Italy), Feb. 27–Mar. 2, 1984, Karger, Basel, pp. 157–159.

DeLoach et al., 1987, "Erythrocytes as carriers of mycotoxins for targeting to the reticuloendothelial system," in *Red Blood Cells as Carriers for Drugs, Potential Therapeutic Applications*, Ropars et al., eds., Pergamon Press, Oxford, Great Britain, pp. 191–197.

DeLoach and Corrier, 1988, "Subcutaneous administration of carrier erythrocytes: slow release of entrapped agent," Biotechnol. Appl. Biochem. 10:359–364.

Eichler et al., 1987, "*In vitro* drug release from human carrier erythrocytes," in *Red Blood Cells as Carriers for Drugs. Potential Therapeutic Applications*, Ropars et al., eds., Pergamon Press, Oxford, Great Britain, pp. 11–15.

Kruse et al., 1987, "Methotrexate loaded erythrocyte carriers: optimizing their formation, their characterization, and their pharmacological efficacy in treating hepatoma 129 ascites tumors in mice," in *Red Blood Cells as Carriers for Drugs. Potential Therapeutic Applications*, Ropars et al., eds., Pergamon Press, Oxford, Great Britain, pp. 137–144.

Makler et al., 1987, "Erythrocyte membrane changes associated with ligands which bind to the glycophorins," in *Red Blood Cells as Carriers for Drugs. Potential Therapeutic Applications*, Ropars et al., eds., Pergamon Press, Oxford, Great Britain, pp. 251–260.

Mishra et al., 1985, "Encapsulation and targeting of drugs in electrically hemolysed red cells," in *Red Blood*

(List continued on next page.)

OTHER PUBLICATIONS

*Cells as Carriers for Drugs. A Method for Disseminating Chemotherapeutics, Hormones, Enzymes and Other Therapeutic Agents via the Circulatory System*, DeLoach and Sprangel, eds., First International Conference on Red Blood Cell Carriers at the Rockefeller Foundation Bellagio Study and Conference Center, Bellagio (Italy), Feb. 27–Mar. 2, 1984, Karger, Basel, pp. 115–126.

Ropars et al., 1985, "Resealed red blood cells as a new blood transfusion product," in *Red Blood Cells as Carriers for Drugs. A Method for Disseminating Chemotherapeutics, Hormones, Enzymes and Other Therapeutic Agents via the Circulatory System*, DeLoach and Sprangel, eds., First International Conference on Red Blood Cell Carriers at the Rockefeller Foundation Bellagio Study and Conference Center, Bellagio (Italy), Feb. 27–Mar. 2, 1984, Karger, Basel, pp. 82–91.

Schlegel, 1985, "Red cell-mediated microinjection of antibodies," in *Red Blood Cells as Carriers for Drugs. A Method for Disseminating Chemotherapeutics, Hormones, Enzymes, and Other Therapeutic Agents via the Circulatory System*, DeLoach and Sprangel, eds., First International Conference on Red Blood Cell Carriers at the Rockefeller Foundation Bellagio Study and Conference Center, Bellagio (Italy), Feb. 27–Mar. 2, 1984, Karger, Basel, pp. 134–141.

Sprandel, 1985, "Erythrocytes as carrier for therapeutic enzymes—an approach towards enzyme therapy of inborn errors of metabolism," in *Red Blood Cells as Carriers for Drugs. A Method for Disseminating Chemotherapeutics, Hormones, Enzymes and Other Therapeutics Agents via the Circulatory System*, DeLoach and Sprangel, eds., First International Conference on Red Blood Cell Carriers at the Rockefeller Foundation Bellagio Study and Conference Center, Bellagio (Italy), Feb. 27–Mar. 2, 1984, Karger, Basel, pp. 7–14.

Sprandel, 1987, "Towards cellular drug targeting and controlled release of drugs by magnetic fields," in *Red Blood Cells as Carriers for Drugs. Potential Therapeutic Applications*, Ropars et al., eds., Pergamon Press, Oxford, Great Britain, pp. 243–250.

Zocchi et al., 1987, "Encapsulation of glucose oxidase in mouse erythrocytes: an experimental model of oxidant-induced cytotoxicity and a means for splenic targeting of carrier erythrocytes," in *Red Blood Cells as Carriers for Drugs. Potential Therapeutic Applications*, Ropars, et al., eds., Pergamon Press, Oxford, Great Britain, pp. 95–101.

Zocchi et al., 1987, "Hepatic or splenic targeting of carrier erythrocytes: a murine model," Biotechnol. Appl. Biochem. 9:423–434.

Zocchi et al., 1988, "*In vivo* liver and lung targeting of adriamycin encapsulated in glutaraldehyde-treated murine erythrocytes," Biotechnol. Appl. Biochem. 10:555–562.

Zocchi et al., 1989, "Encapsulation of doxorubicin in liver-targeted erythrocytes increases the therapeutic index of the drug in a murine metastatic model," Proc. Natl. Acad. Sci. USA 86:2040–2044.

Blätter et al., 1985, "New heterobifunctional protein cross-linking reagent that forms an acid-labile link," Biochemistry 24:1517–1524.

Carlsson et al., 1978, "Protein thiolation and reversible protein-protein conjugation", Biochem. J. 173:723–737.

Coller et al., 1990, "Thromboerythrocytes: preliminary in vitro attempts to develop a semi-artificial, autologous platelet (P) substitute," Circulation, Suppl. III., 82(4), Abstract 2377.

Coller, 1989, "Theoretical And Practical Considerations In The Use Of Monoclonal Antibodies To Image Thrombi In Vivo", *Monoclonal Antibodies In Immunoscintography*, pp. 357–364 [Pre-printing draft].

Jue et al., 1978, "Addition of sulhydryl groups to *Escherichia coli* ribosomes by protein modification with 2-iminothiolane (methyl 4-mercaptobutyrimidate)," Biochemistry 17:5399–5405.

Jung and Moroi, 1983, "Crosslinking of platelet glycoprotein Ib by N-succinimidyl(4-azidophenyldithio)propionate and 3,3'-dithiobis(sultosuccinimidyl propionate," Biochem. Biophys. Acta, 761:152–162.

Kaplan, 1982, "Sodium pump-mediated ATP:ADP exchange: The side effect of sodium and potassium ions," J. Gen. Physiol. 80:915–937.

Liu et al., 1979, "New procedures for preparation and isolation of conjugates of proteins and a synthetic copolymer of D-amino acids and immunochemical characterization of such conjugates," Biochemistry 18:690–697.

Märki et al., 1981, "Total solid-phase synthesis of por- (List continued on next page.)

OTHER PUBLICATIONS cine gut gastrin releasing peptide (GRP), a mammalian bombesin," J. Am. Chem. Soc. 103:3178-3185.

Novick et al., 1987, "The human interferon-γ receptor," J. Biol. Chem. 262:8483-8487.

Poznansky et al., 1984, "Insulin: carrier potential for enzyme and drug therapy," Science 223:1304-1306.

Sachs, 1988, "Volume-Sensitive K Influx in Human Red Cell Ghosts", J. Gen. Physiol. 92:685-711.

Staros, 1982, "N-hydroxysulfosuccinimide active esters: Bis(N-hydroxysulfosuccinimide) esters of two dicarboxylic acids are hydrophilic, membrane-impermeant, protein cross-linkers," Biochemistry 21:3950-3955.

Yoshitake et al., 1979, "Conjugation of Glucose Oxidase from *Aspergillus niger* and Rabbit Antibodies Using N-Hydroxysuccinimide Ester of N-(4-Carboxycyclohexylmethyl)-Maleimide", Eur. J. Biochem. 101:395-399.

Tonetti et al., 1990, Construction and characterization of adriamycin-loaded canine red blood cells as a potential slow delivery system, Biotechnology and Applied Biochemistry 12:621-629.

Agam et al., (1983) "Passive Participation of Fixed Platelets in Aggregation Facilitated by Covalently Bound Fibrinogen", Blood, 61, 186-191.

Blatter et al., (1985) Biochemistry, 24, 1517-152.

Brearley et al., 1990, "The Retention of Entrapped Molecules Within Erythrocyte Ghosts During Cryopreservation", J. Pharm. Pharmocol., 42:297-301.

Carlsson et al., (1987) "Protein Thiolation and Reversible Protein-Protein Conjugation", Biochem. J., 173, 723-737.

Cole et al., 1985, "The EBV-Hybridoma Technique and Its Application to Human Lung Cancer", in *Monoclonal Antibodies and Cancer Therapy*, Alan R. Liss Inc., pp. 77-96.

Coller, "Theoretical And Practical Considerations In The Use Of Monoclonal Antibodies To Image Thrombi In Vivo", *Monoclonal Antibodies In Immunoscintography*, 357-364, (1989).

Coller et al., 1991, Further in vitro characterization of Thromboerythrocytes (TE). A potential analogous semi-artificial platelet substitute, Thrombosis and Haemostasis 65(6):755.

Cote et al., 1983, "Generation of Human Monoclonal Antibodies Reactive With Cellular Antigens", Proc. Natl. Acad. Sci., U.S.A. 80:2026-2030.

Editorial, 1988, "Drug Delivery in Red Blood Cells", Lancet, pp. 1437-1438.

Hashida et al., 1984, J. Applied Bhiochem. 6:56-63.

Jue et al., (1978) Biochemistry, 17, 5399-5405.

Jung and Moroi, 1983, Biochem. Biophys. Acta. 761:152-162.

Kaplan, 1982, Sodium Pump-Mediated ATP:ADP Exchange: The Side Effect of Sodium and Potassium Ions, J. Gen. Physiol., 80:915-937.

Kohler & Milstein, 1975, "Continuous Cultures of Fused Cells Secreting Antibody of Predefined Specificity", Nature 256:495-497.

Kozbor et al., 1983, "The Production of Monoclonal Antibodies From Human Lymphocytes", Immunology Today 4:72.

Liu et al., (1979) Biochemistry, 18:690-697.

Marki et al., 1981, J. Am. Chem. Soc., 103, 3178.

Morrison et al., 1984, "Chimeric Human Antibody Molecules. Mouse Antigen-Binding Domains With Human Constant Region Domains", Proc. Natl. Acad. Sci., U.S.A. 81:6851-6855.

Neuberger et al., 1984, "Recombinant Antibodies Possessing Novel Effector Functions", Nature 312:604-608.

Novick et al., (1987) J. Biol. Chem., 262, 8483-8487.

Poznansky et al., Science, 223, 1304-1306 (1984).

Ramsey et al., 1986, "The Influence of Hypotonic Lysis and Desferrioxamine Encapsulation on Survival Kinetics of C3H Erythrocytes", Clin. Res., 34:468A.

Sachs, 1988, "Volume-Sensitive K Influx in Human Red Cell Ghosts", Volume Sensitive K Influx in Human Red Cell Ghosts, J. Gen. Physiol., 92:685-711.

Staros, (1982) Biochemistry, 21, 3950-3955.

Takeda et al., 1985, "Construction of Chimaeric Processed Immunoglobulin Genes Containing Mouse Variable and Human Constant Region Sequences", Nature 314:452-454.

Updike & Wakamiya, 1983, Infusion of Red Blood Cell-Loaded Asparaginase in Monkey, J. Lab. Clin. Med., pp. 679-691.

Yoshitake et al., (1979) "Conjugation of Glucose Oxidase from *Aspergillus niger* and Rabbit Antibodies Using N-Hydroxysuccinimide Ester of N-(4-Carboxycyclohexylmethyl)-Maleimide", Eur. J. Biochem., 101, 395-399.

Thromboerythrocytes

Control Erythrocytes

METHOD FOR PREPARING TARGETED CARRIER ERYTHROCYTES

The invention disclosed in this specification was partially made with Government Support under research grant NHLBI 19278 awarded by The National Institutes of Health. The Government has certain rights in this invention.

This is a continuation-in-part of copending application Ser. No. 07/611,164 filed Nov. 9, 1990, which in turn is a continuation-in-part of copending application Ser. No. 07/394,018 filed Aug. 15, 1989 now abandoned, the disclosures of which are incorporated by reference herein in their entireties.

1. FIELD OF THE INVENTION

The present invention is directed to a new composition of matter called thrombo-erythrocytes, which have the ability to bind selectively to activated platelets but not to unactivated platelets. The thrombo-erythrocytes are useful in controlling bleeding in thrombocytopenic (blood platelet deficient) mammals, and for the uptake and delivery of labels, therapeutic agents and genetic materials to selected targets. The invention further relates to targeted erythrocytes and their uses in the uptake and delivery of compounds.

2. BACKGROUND OF THE RELATED ART

2.1. Control of Bleeding

Mammals control bleeding by producing platelets, which are activated with agents that are produced or released at the site of a wound. Activation is necessary for the platelets to aggregate into clumps or clots.

The activation of platelets is a complicated process, which includes producing or exposing receptors for the plasma protein fibrinogen on the platelet surface. Fibrinogen has multiple binding sites, and binds two or more platelets simultaneously, initiating the aggregation. A platelet receptor that is present on the surface of platelets and becomes exposed during the activation process is GPIIb/IIIa. Patients with low platelet counts often require transfusions of platelets in order to control bleeding.

In 1910, Duke provided data suggesting that transfusion of whole blood containing platelets could arrest hemorrhage due to thrombocytopenia (Duke, 1910, *J. Am. Med. Assoc.* 60:1185-1192). It was not, however, until the 1950's that unequivocal data on the efficacy of platelet transfusions were obtained in animals made thrombocytopenic by treatment with total body irradiation (Cronkite et al., 1959, in *Progress in Hematology*, vol. 2, Tocantins, ed, Grune and Stratton, N.Y., pp. 239-257). The difficulties in platelet procurement and storage led investigators to seek alternatives to fresh platelets soon thereafter. Studies performed with lyophilized platelets and disintegrated platelets indicated that these products failed to arrest bleeding (Cronkite et al., supra; Jackson et al., 1959, *J. Clin. Invest.* 38:1689; Hjort et al., 1959, *Proc. Soc. Exp. Biol. Med.* 102:31-35). When phospholipids were found capable of substituting for platelets in accelerating coagulation reactions, the cephalin fraction of soy bean phosphatides was investigated as a platelet substitute in thrombocytopenic children (Shulman et al., 1959, *Ann. N.Y. Acad. Sci.* 75:195, Abstr.). Although a preliminary report suggested clinical improvement in some patients (Schulman et al., supra) animal studies did not identify a benefit and this approach was eventually abandoned (Kahn, et al., 1985 *Blood* 66:1-12, Abstr.). Cryopreservation of autologous platelets has been successfully utilized in patients with problems related to alloimmunization and isoimmunization (Schiffer et al., *N. Engl. J. Med.* 299:7-12), but the platelet yield is less than with fresh platelets, and the technique is limited by the need for extra processing and the availability of storage space (Murphy, 1991, In *Principles of Transfusion Medicine*, Williams & Wilkins, Baltimore, pp. 205-213).

Improved understanding of platelet physiology has led to additional approaches to obtain a platelet substitute. Several investigators have been able to introduce platelet glycoproteins into liposomes for in vitro experiments (Parise and Phillips, 1985, *J. Biol. Chem.* 260:1750-1756; Baldassare et al., 1988, *J. Clin. Invest.* 75:35-39; Rybak, 1986, *Thromb. Haemostas.* 55:240-245). More recently, Ryback and Renzulli incorporated a deoxycholate extract of platelet membranes containing 15 proteins, including GPIb, GPIIb/IIIa, and GPIV, into small (50-200 nm) unilamellar liposomes prepared from either sphingomyelin:phosphatidylcholine:monosialyloganglioside or egg phosphatide (*Blood Suppl.* 1:473a, abstr). Intra-arterial injections of both preparations decreased bleeding in thrombocytopenic rats to the same extent as human platelets did, but neither produced complete normalization of the bleeding time. Interestingly, liposomes containing GPIIb/IIIa alone were ineffective (Rybak and Renzulli, 1990, *Blood Suppl.* 1:473a, Abstr.). This approach may provide important mechanistic information but as a therapeutic intervention it potentially suffers from the generic problems of liposomes, including the possibility of short in vivo survival and potential blockade of the reticuloendothelial system (Kahn et al., 1985, *Blood* 66:1-12, Abstr.). Moreover, since platelets remain the starting material, problems of platelet procurement and the risks of transmitting infectious diseases may not be eliminated. Finally, if whole platelet extracts are required, immunogenicity may limit the opportunity for repeat therapy because platelets have class I HLA antigens (McFarland and Aster, 1991, In *Principles of Transfusion Medicine*, Williams & Wilkins, Baltimore, pp. 193-204), and some platelet glycoproteins are polymorphic (Lopez and Ludwig, 1991, *Clin. Res.* 39:327 a.s.).

Agam and Livne took an approach based on their observations that passive, fixed platelets coated with fibrinogen could function to augment platelet aggregation of native, fresh platelets (Agam and Livne, 1983, *Blood* 61:186; Agam and Livne, 1984, *Thromb. Haemostas.* 51:145-149; Agam and Livne, 1988, *Thromb. Haemostas.* 59:504-506). They concluded that the activated platelets had to undergo the release reaction and expose thrombospondin on their surface in order for the interactions to occur, with the final interaction between the fibrinogen on the fixed platelets and the thrombospondin on the activated platelets (Agam and Livne, 1983, *Blood* 61:186; Agam and Livne, 1984, *Thromb. Haemostas.* 51:145-149; Agam and Livne, 1988, *Thromb. Haemostas.* 59:504-506). This suggests that the fixation process alters the fibrinogen so that it cannot interact directly with GPIIb/IIIa, but leaves intact portions of the fibrinogen molecule that can interact with thrombospondin. This approach involves a significant limitation in that it relies on the purification of fibrinogen from plasma, and thus has the risk of transmitting blood-borne disease. Moreover, formaldehyde is a cytotoxic agent that may have carcinogenic potential (Feron et al., 1991, *Mutation Res.* 259:363-385) and so it may not be the most desirable crosslinking reagent for in vivo use.

Until the present invention, platelet transfusion was the only effective therapy for the prevention and treatment of hemorrhage due to thrombocytopenia (Heyman et al., 1991, in *Principles of Transfusion Medicine,* William & Wilkens, Baltimore, pp. 223-231). The number of units of platelets transfused each year in the United States has grown rapidly since the widespread introduction of platelet transfusion therapy in the 1960's; in fact, just between 1980 and 1987 the number nearly doubled, reaching in excess of 6 million units per year (Surgenor et al., 1990, *N. Engl. J. Med.* 322:1646-1651). Despite its enormous success, platelet transfusion therapy has a number of very serious limitations and drawbacks: 1) supplies are often limited due to difficulties in procurement and the relatively short shelf life (5-7 days) (Murphy, 1991, in *Principles of Transfusion Medicine,* Williams & Wilkens, Baltimore, pp. 205-213); 2) there is a risk of transmitting blood-borne pathogens such as the viruses that produce hepatitis and AIDS, especially since multiple units are usually administered with each transfusion (Heyman et al., supra); 3) febrile reactions, presumably due to white blood cell contaminants, are common in patients receiving repeated transfusions (Snyder et al., 1991, in *Principles of Transfusion Medicine,* Williams & Wilkens, Baltimore, pp. 641-648); 4) alloimmunization results in patients becoming refractory to random donor platelets, necessitating a switch to single donor platelets matched for HLA antigens, and even HLA matched platelet transfusions are not universally successful (Heyman, et al., supra).

The interaction between fibrinogen and platelets has been the subject of prior investigations. For example, platelets interact with fibrinogen-coated polyacrylonitrile beads via a mechanism involving fibrinogen receptors on platelet surfaces (see the paragraph bridging pages 177 and 178 in Coller et al., 1980, *Blood,* 55:169-178). Agam and Livne (1983, *Blood* 61:186-191) disclosed that fixed platelets to which fibrinogen had been bound participated in the aggregation of activated platelets, by selective reaction with activated platelets. Ruoslahti et al., U.S. Pat. No. 4,792,525 suggested that the ability of proteins such as fibrinogen to interact with cells is associated with the amino acid sequence Arg-Gly-Asp-Ser within the fibrinogen structure. The Ruoslahti et al. patent further discloses that a tetrapeptide consisting of the sequence Arg-Gly-Asp-Ser, when properly immobilized on a substrate, has the property of causing cell attachment to the substrate. The tetrapeptide could be extended with additional amino acids at either end, and the possibility of very limited substitution for the amino acids constituting the tetrapeptide was suggested. A practical application envisioned by Ruoslahti et al. was platelet aggregation.

Despite the known role of platelets in controlling bleeding and of the interaction between fibrinogen and platelets, there are no current procedures for controlling bleeding in thrombocytopenic patients other than platelet transfusions, with all the disadvantages of such transfusions, as discussed above.

The availability of an abundant and safe alternative to human platelets would, therefore, be of considerable benefit. It is vital, however, that such an alternative retain the platelet's specificity for forming thrombi at sites of vascular injury, to be certain that indiscriminate thrombus formation does not occur. Prior to the instant invention, no abundant safe alternative to human platelets has been found.

Alternative procedures are needed in order to reduce the large amount of blood necessary to obtain sufficient platelets. The ideal procedure would utilize a patient's own blood cells in order to reduce the possibility of blood borne disease.

In addition, the precise delivery of radiolabeled molecules, diagnostic, and therapeutic agents to specific target tissues is an important laboratory and clinical problem.

Accordingly, one objective of the present invention is to solve the problems of obtaining cells from a small amount of blood, particularly autologous blood, that can be used to deliver precisely agents to specific target issues.

Another objective is to provide compositions of matter that are able to bind selectively to activated platelets but not to unactivated platelets in vivo. Activation refers to the process by which platelets become more susceptible to aggregation. The process by which platelets become activated is poorly understood, especially, in vivo. It appears that the activation process is induced by a number of agonists, such as ADP, epinephrine, collagen, thrombin and thromboxane A2. Indiscriminate binding of an agent to both activated and unactivated platelets exposes the patient to the risk of thrombosis (blood clots) that can lead to the death of tissues in vital organs, including the heart and brain.

3. SUMMARY OF THE INVENTION

The present invention provides new compounds and methods for promoting platelet aggregation, and preventing hemorrhage. The present invention is based on the surprising discovery that erythrocytes conjugated to certain peptides and polypeptides containing an R-G-D (Arg-Gly-Asp) sequence (collectively termed herein "RGD peptides") according to the invention, selectively bind to activated platelets but not to unactivated platelets. In recognition of the dual nature of the derivatized erythrocytes, they are termed herein "thrombo-erythrocytes". The methods and compounds of the invention overcome the problems with prior art platelet substitutes by providing abundant, safe material to promote platelet aggregation, specific for sites of injury. By following the methods of the instant invention, thrombo-erythrocytes are produced which surprisingly, have no significant change in their rheological properties. In addition, contrary to expectations, and in a preferred aspect, the thrombo-erythrocytes have the majority of RGD peptide cross-linked specifically to glycophorin A and glycophorin B on the surface of the erythrocyte, producing a thrombo-erythrocyte that has an altered membrane surface that can interact selectively with activated platelets via the platelet GPIIb-/IIIa receptor. In the thrombo-erythrocytes of the invention, preferably, the N-terminal Arg of the R-G-D sequence should be spaced within 9-50 Angstroms, more preferably 10-40 Angstroms, and most preferably 11-25 Angstroms, from the erythrocyte protein to which the RGD peptide is conjugated. As a result, the activated platelets aggregate with the erythrocytes, forming clumps or clots. When such clumps or clots form in vivo in mammals, including humans, they are helpful in controlling bleeding, and are especially helpful in controlling bleeding from small wounds.

The invention is further directed to erthrocytes modified by replacement of their intracellular contents with a composition comprising a label or agent. Such modified erythrocytes are termed herein "carrier erythrocytes". The carrier erythrocytes have use in delivery of such labels or biologically active agents to specific tissues by conjugation to a targeting agent. In one embodiment, the carrier erythrocytes are thrombo-erthrocytes, and are thus targeted to a specific tissue, in particular an activated platelet, by conjugation with an RGD peptide in accordance with the present invention. In other embodiments, different targeting molecules, such as peptides, proteins, antibodies, antibody fragments, lectins, carbohydrates, or steroids can be conjugated to a carrier erythrocyte or, in particular, a carrier thrombo-erythrocyte.

4. BRIEF DESCRIPTION OF THE DRAWINGS

FIG. 1. Osmotic fragility of control erythrocytes and thrombo-erythrocytes. The lysis of control erythrocytes and thrombo-erythrocytes was measured after a 20 min incubation in solutions containing various salt concentrations. The results are expressed in comparison to the hemolysis produced by distilled water, which was defined as 100%. Data are from 3 separate experiments.

Figure 2:
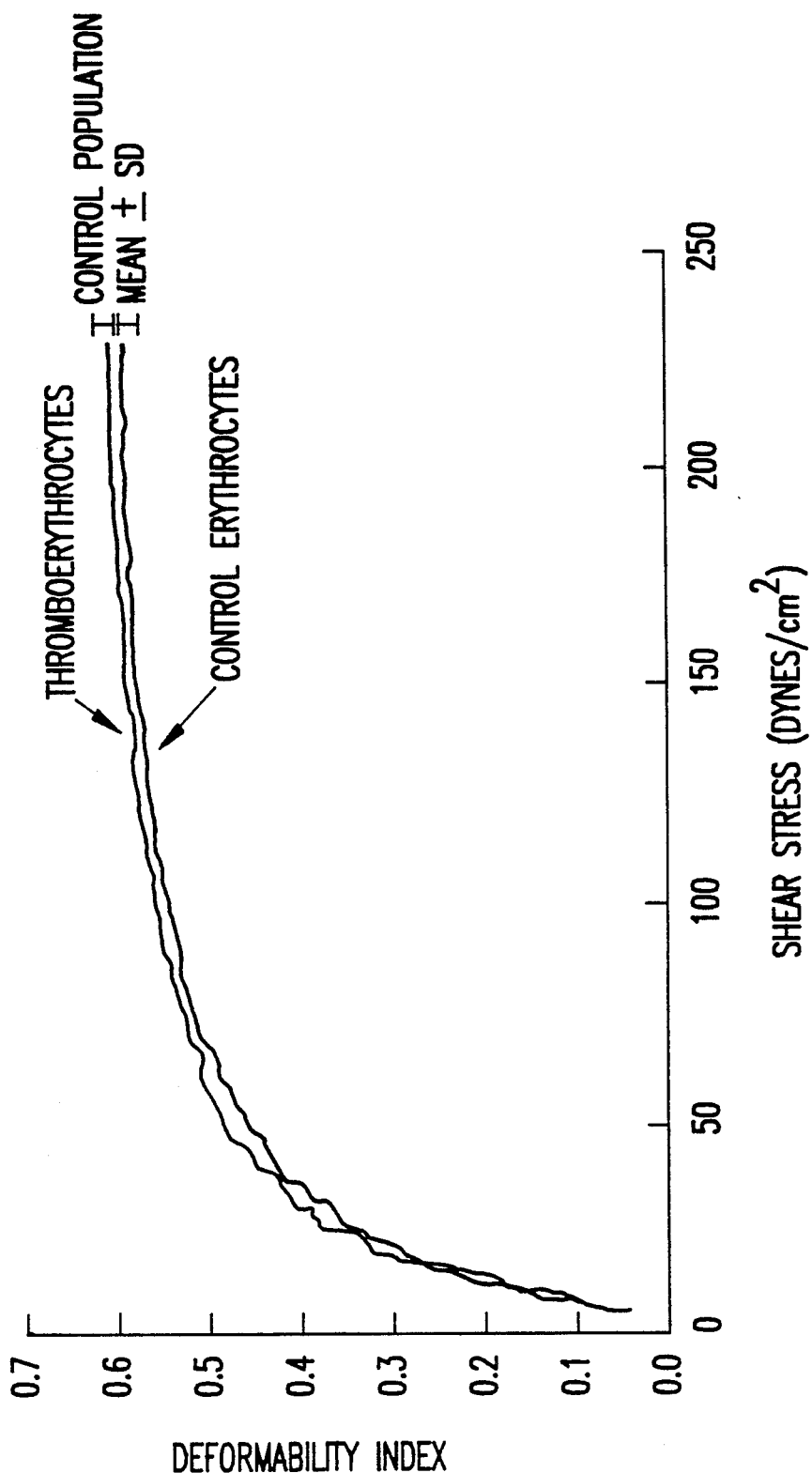

FIG. 2. Ektacytometer analysis of thrombo-erythrocytes and control erythrocytes. Thrombo-erythrocytes were prepared as described, with samples removed after 15 min, 30 min, 60 min, and 120 min of incubation. The thrombo-erythrocytes were then washed in 0.15 M NaCl, 10 mM Tris/HCl, 5 mM KCl, 10 mM glucose, 1% bovine serum albumin, pH 7.4, and resuspended to a hematocrit of ~33%. Three different erythrocyte controls were prepared: 1) erythrocytes that were just washed in the above buffer, 2) erythrocytes incubated with peptide, but no mal-sac-HNSA, and 3) erythrocytes incubated with mal-sac-HNSA, but no peptide. The deformability index of each sample was measured as a function of shear rate in an isotonic medium of 22 cp viscosity. All of the thrombo-erythrocyte samples and control samples gave virtually superimposable curves, and so for simplicity only the washed erythrocyte control and the 120 min thrombo-erythrocyte sample are shown. The plateau deformability index (mean±SD) of more than 200 normal samples is also shown, indicating that all of the samples tested were within this normal range.

Figure 3:
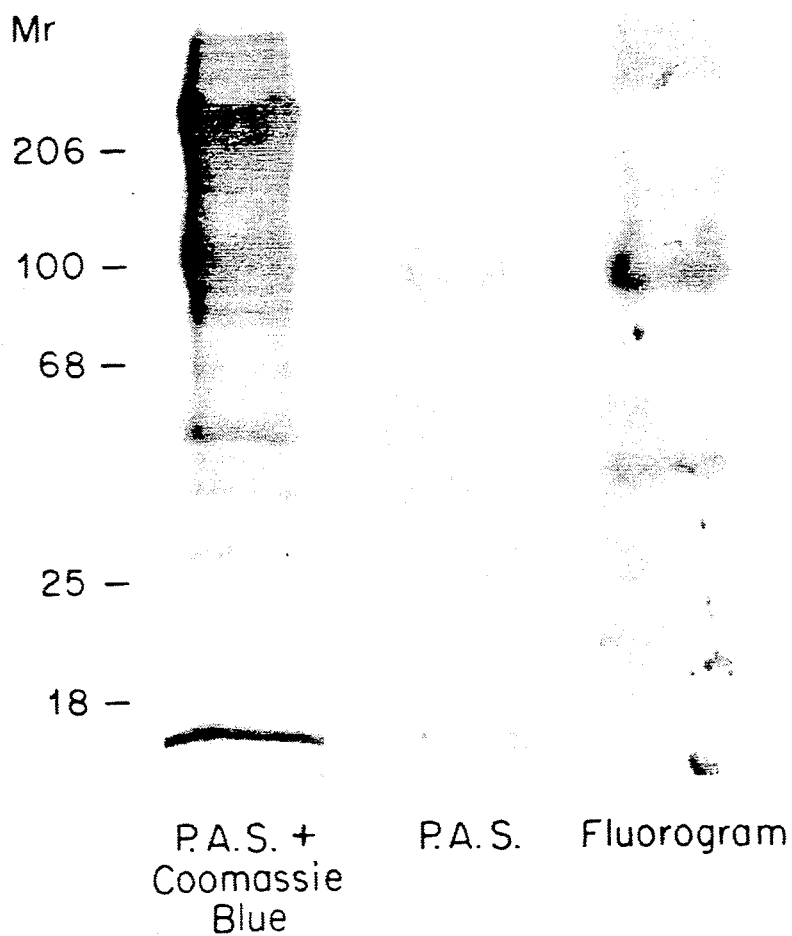

FIG. 3. Analysis of thrombo-erythrocyte membrane proteins involved in peptide crosslinking. After cross-linking the $^3$H-peptide to erythrocytes, the cells were washed and lysed. The thrombo-erythrocyte ghosts were then solubilized in sodium dodecyl sulfate and electrophoresed in a 12.5% polyacrylamide gel. The gel was sequentially stained with the periodic acid-Schiff technique (P.A.S.), photographed, stained with Coomassie blue, photographed, and then prepared for fluorography by reactions with precipitating and aqueous fluorescent solutions. The gel was subsequently dried and placed a cassette with X-ray film at −70° C. for 7 days. The P.A.S. stain revealed 3 major bands of Mr 87,000, 42,000, and 22,000, which corresponded to the radioactive bands identified by fluorography.

Figure 4:
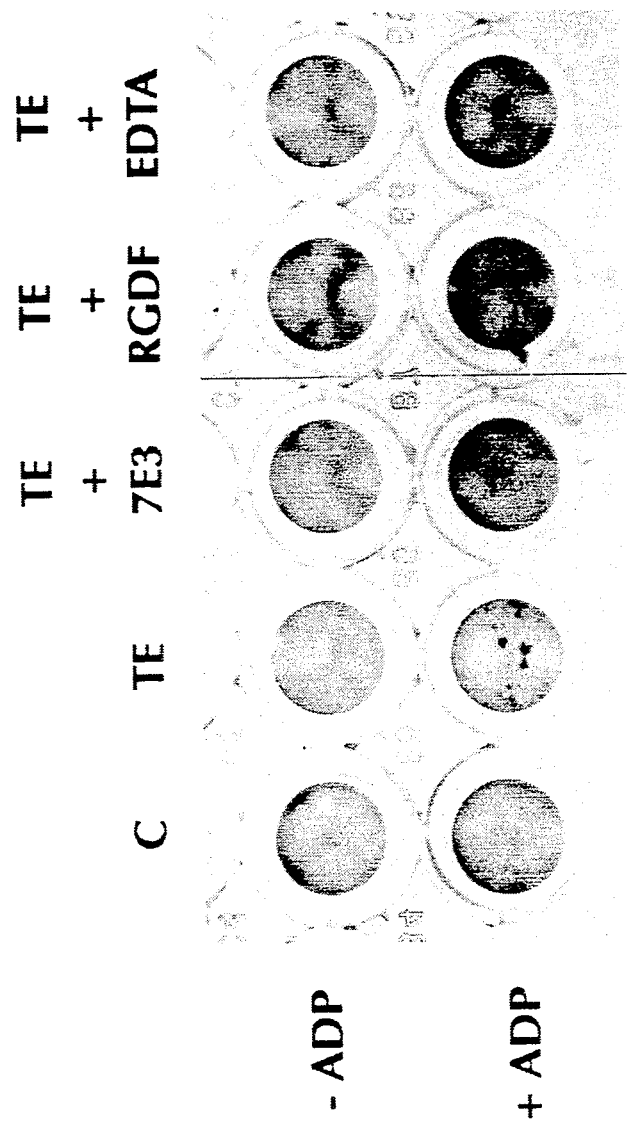

FIG. 4. Platelet-thrombo-erythrocyte co-aggregation assay. Thrombo-erythrocytes and control erythrocytes were prepared as described in Section 8.1 and adjusted to a 10% hematocrit. Citrated platelet-rich plasma was prepared (~500,000 platelets/µl) and incubated with antibody 7E3 (anti-GPIIb/IIIa+anti-$\alpha v\beta_3$ vitronectin receptor; 40 µg/ml final concentration), EDTA (10 mM final concentration), RGDF (300 µg/ml final concentration) or buffer (0.15M NaCl, 0.01M Tris/HCl, 0.05% Na azide, pH 7.4) for 30 min at 22° C. The assay was performed by adding 50 µl of PRP to microtiter wells, followed by 10 µl of ADP to selected wells, and finally 5 µl of the thrombo-erythrocytes. The microtiter plate was then rotated at 270 rpm at 22° C. for approximately 6 min and then the plate was photographed. Note the absence of platelet aggregation or platelet-erythrocyte co-aggregation in the samples without ADP. With ADP treatment, the thrombo-erythrocytes enter into mixed aggregates with the platelets. Careful inspection of the sample of control erythrocytes with ADP stimulation shows small white aggregates of platelets, indicating that platelet activation and aggregation occurred, but the control erythrocytes did not enter into the aggregates.

Figure 5:
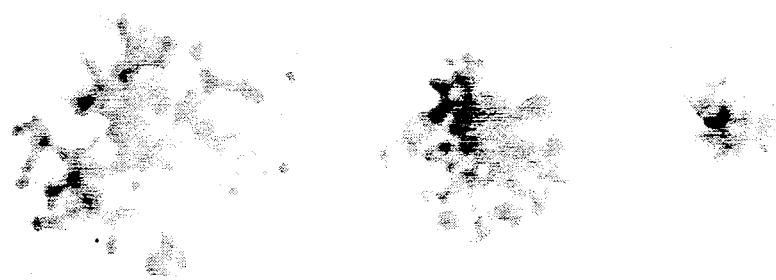
Figure 5:
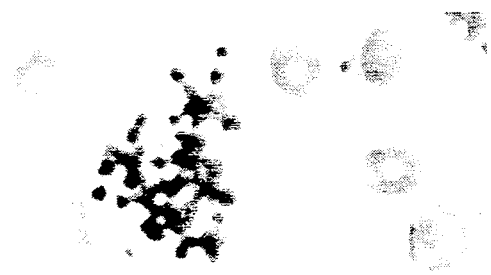

FIG. 5. Platelet-thrombo-erythrocyte interactions. After performing the platelet-thrombo-erythrocyte co-aggregation assay, samples were spread on a glass slide, air-dried, and stained with a Wright stain. Light microscopy was performed at 1,000× magnification with an oil immersion lens. Note the intimate association between the platelets and the thrombo-erythrocytes, with the platelets interdigitated between the thrombo-erythrocytes. With PRP+control erythrocytes, activation with ADP led to platelet aggregates, but the control erythrocytes did not enter into the aggregates.

Figure 6:
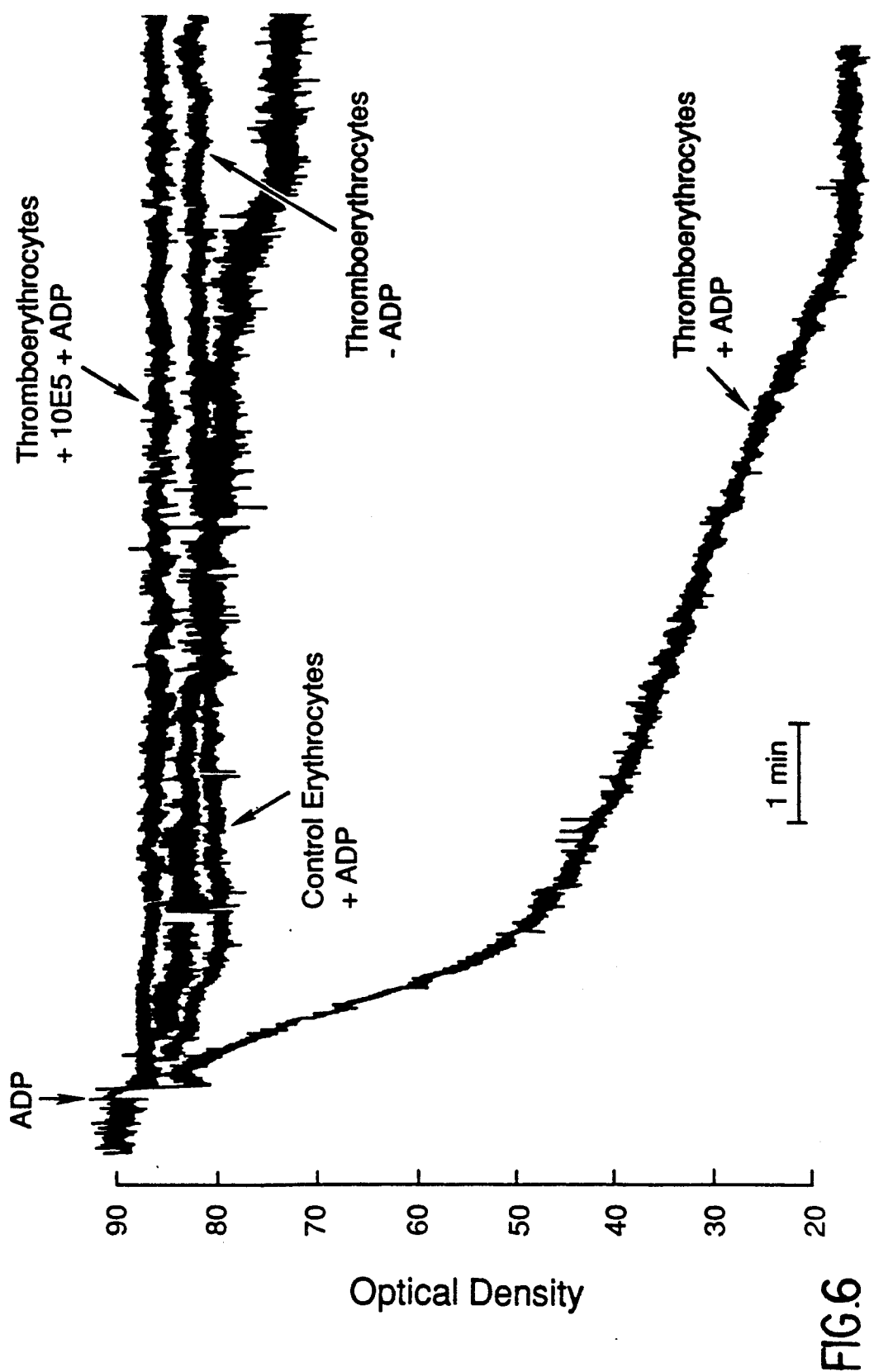

FIG. 6. Interactions of control erythrocytes and thrombo-erythrocytes with gel-filtered platelets. Gel-filtered platelets (450 µl; 340,000/µl), prepared as described in Section 8.1, and control erythrocytes or thrombo-erythrocytes (20 µl; 10% hematocrit) were stirred in an aggregometer cuvette and then ADP (4.3 µM final concentration) was added. In this assay, the erythrocytes contribute significantly to the optical density. Control erythrocytes do not enter into platelet aggregates and so there is only a slight decrease in optical density in this sample. In contrast, thrombo-erythrocytes do interact with the ADP-activated platelets, resulting in a dramatic decrease in optical density. The thrombo-erythrocytes do not, however, interact with unactivated platelets despite stirring at 37° C. Finally, preincubating the platelets with antibody 10E5, which reacts with GPIIb/IIIa, blocks the platelet-platelet and platelet-thrombo-erythrocyte interactions. A mixture of gel-filtration buffer (450 µl) and control erythrocytes (20 µl) was used to establish the full scale deflection.

Figure 7:
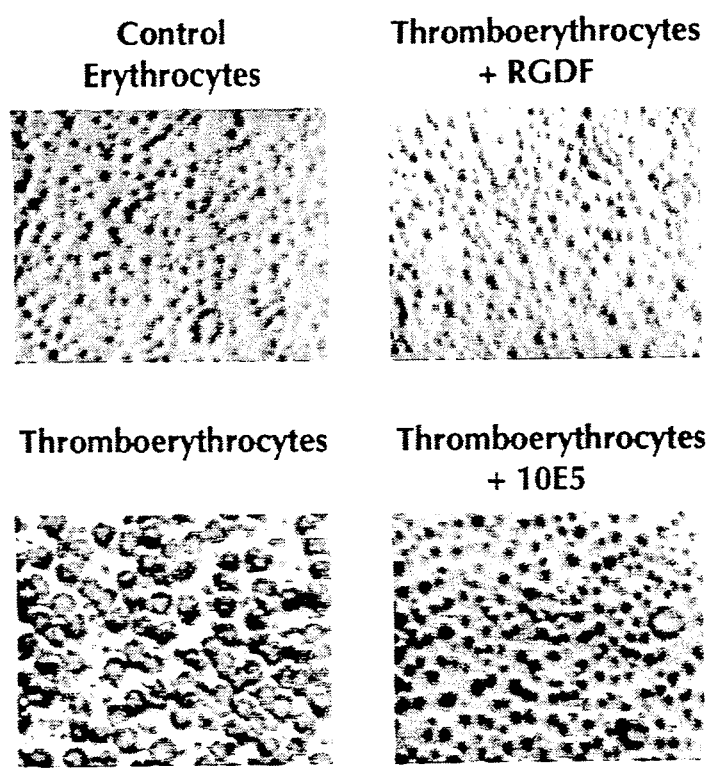

FIG. 7. Interactions of control erythrocytes and thrombo-erythrocytes with platelets adherent to collagen. Gel-filtered platelets were allowed to form a dense lawn on collagen-coated microtiter wells and then, after washing, control erythrocytes or thrombo-erythrocytes (50 µl; 10% hematocrit) were added to the wells for 1 hour at 22° C. Finally, non-adherent control erythrocytes and thrombo-erythrocytes were removed by washing. With control erythrocytes, the dense lawn of platelets can be seen with only a single adherent erythrocyte in the field. In sharp contrast, the thrombo-erythrocytes bound extensively to the adherent platelets. The binding of thrombo-erythrocytes to the adherent platelets was inhibited by antibody 10E5 (20 µg/ml), which is specific for GPIIb/IIIa, or the peptide RGDF (400 µg/ml). The experiment shown is representative of more than 12 separate experiments.

Figure 8A:
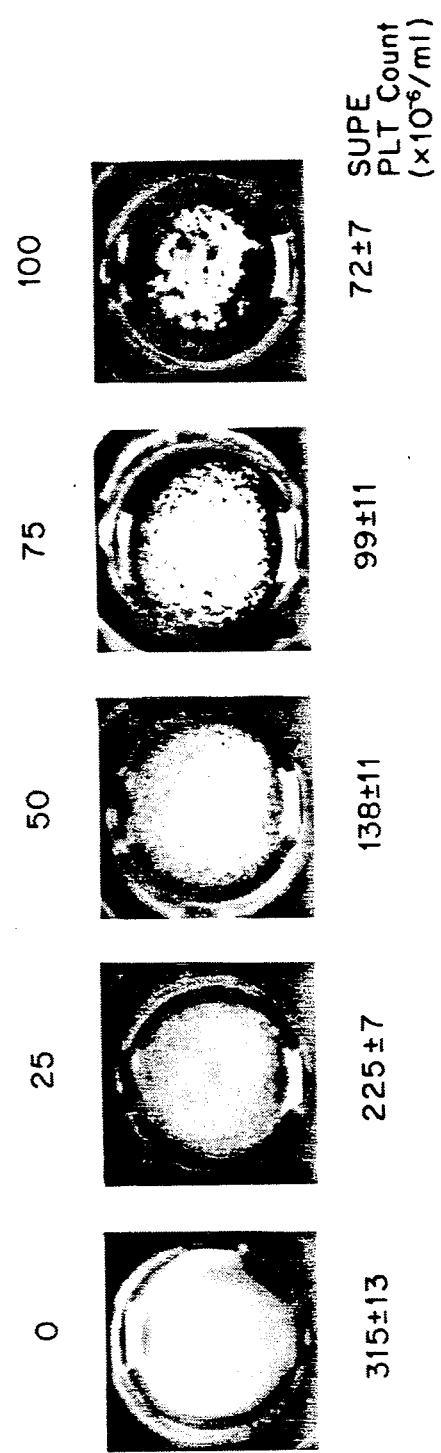

FIG. 8A. Rating of (G)$_n$RGDF bead agglutination. Platelet-rich plasma (PRP; 70 μl) was reacted with G$_9$-RGDF beads (5 μl containing 0.22 mg beads) as described in Section 9.1 and rotated at 260 rpm. With increasing time, the agglutination became more extensive. The examples shown were selected at different time intervals to demonstrate the semiquantitative scale used for judging the extent of agglutination. Also shown are the platelet counts in the supernatant fluid after allowing the bead agglutinates to settle for 3 minutes.

Figure 8B:
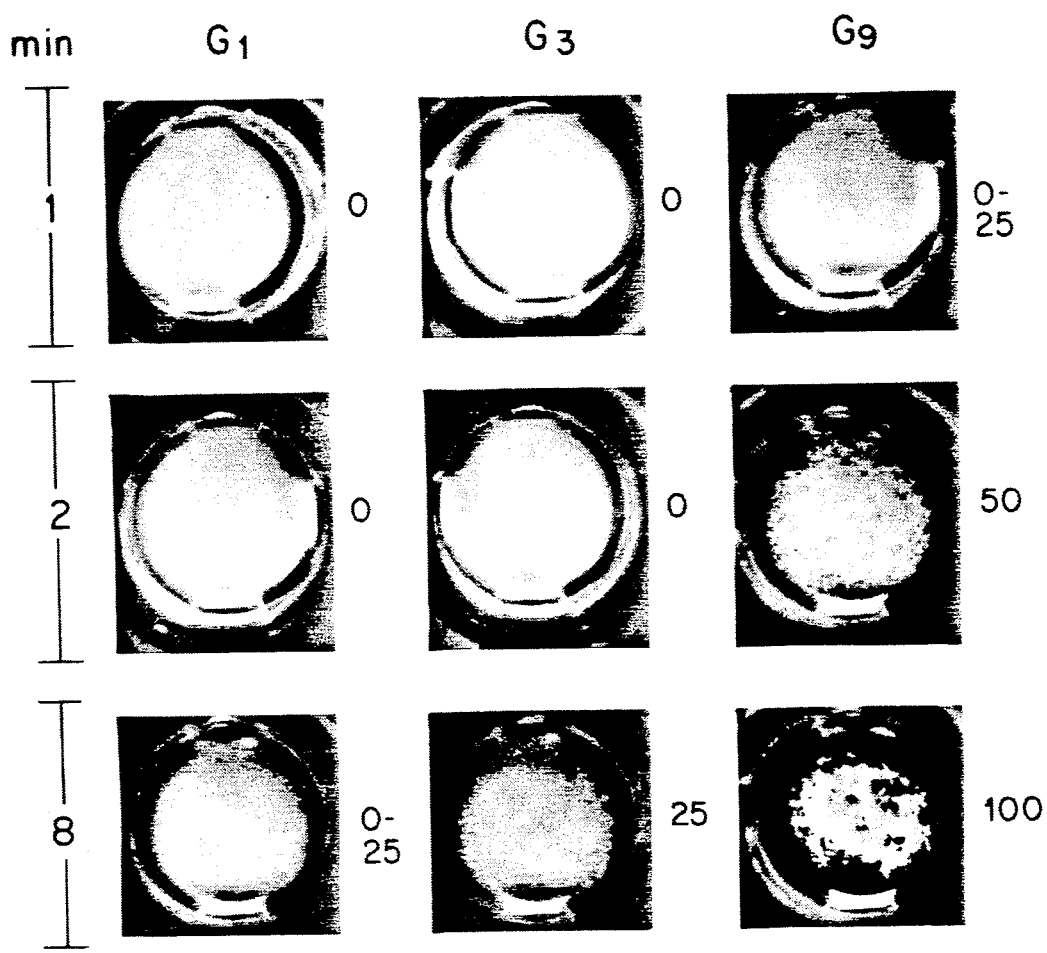

FIG. 8B. (G)$_n$-RGDF bead agglutination in PRP. The experiment was conducted as above using G$_1$-RGDF, G$_3$-RGDF, and G$_9$-RGDF beads. The reaction was stopped at the time points indicated on the left and the microtiter plate was photographed. The grading of the extent of agglutination is indicated on the right of each well. Note the minimal agglutination with the G$_1$-RGDF beads, the modest agglutination with the G$_3$-RGDF beads, and the extensive agglutination of the G$_9$-RGDF beads over the first 8 min.

Figure 9A:
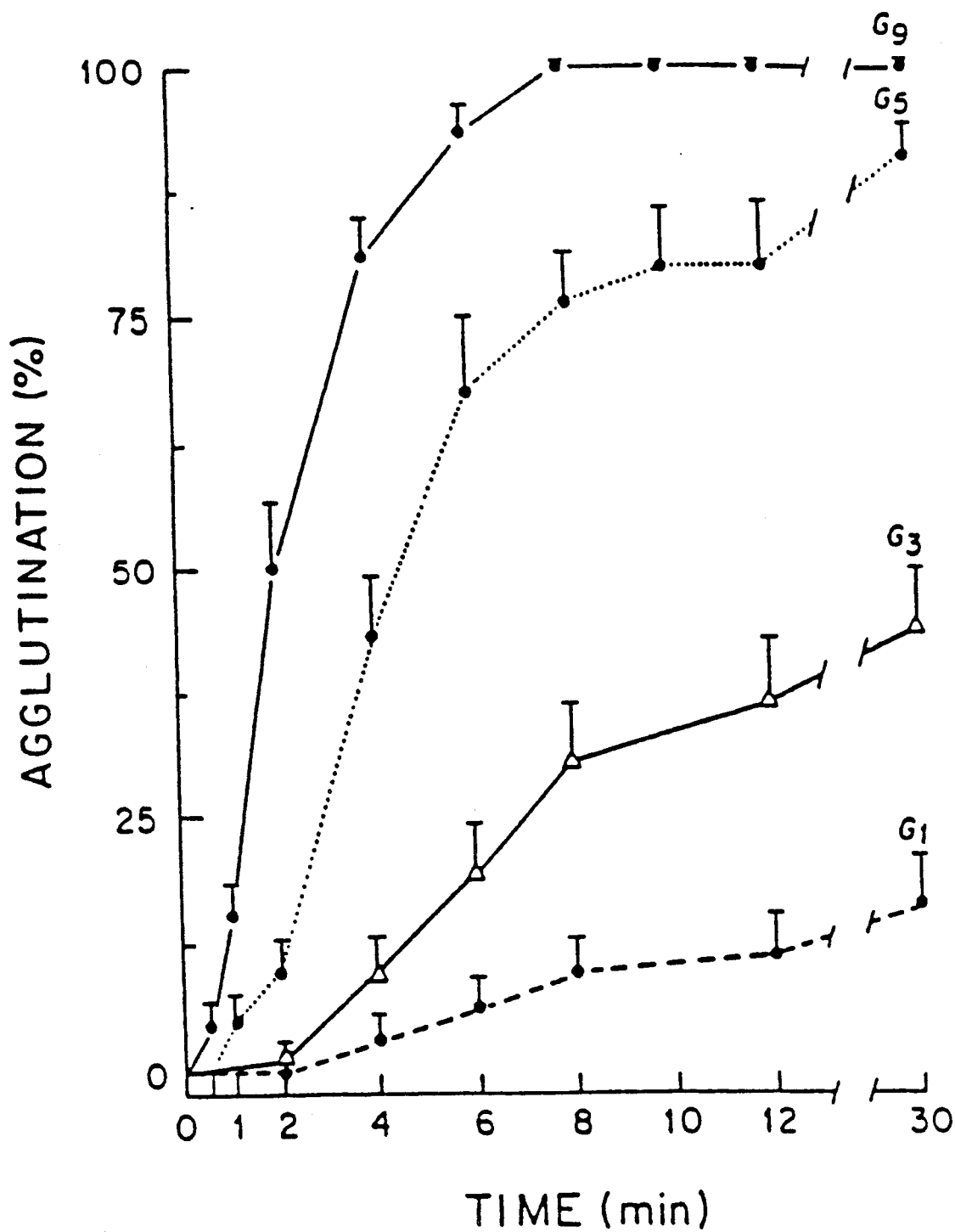

FIG. 9A. Agglutination of (G)$_n$-RGDF beads by PRP. The experiments were carried out with PRP and G$_1$-PGDF (n=15), G$_3$-RGDF (n=17), G$_5$-RGDF (n=15), and G$_9$-RGDF (n=16) beads as indicated in the text. The values plotted are the mean±SEM.

Figure 9B:
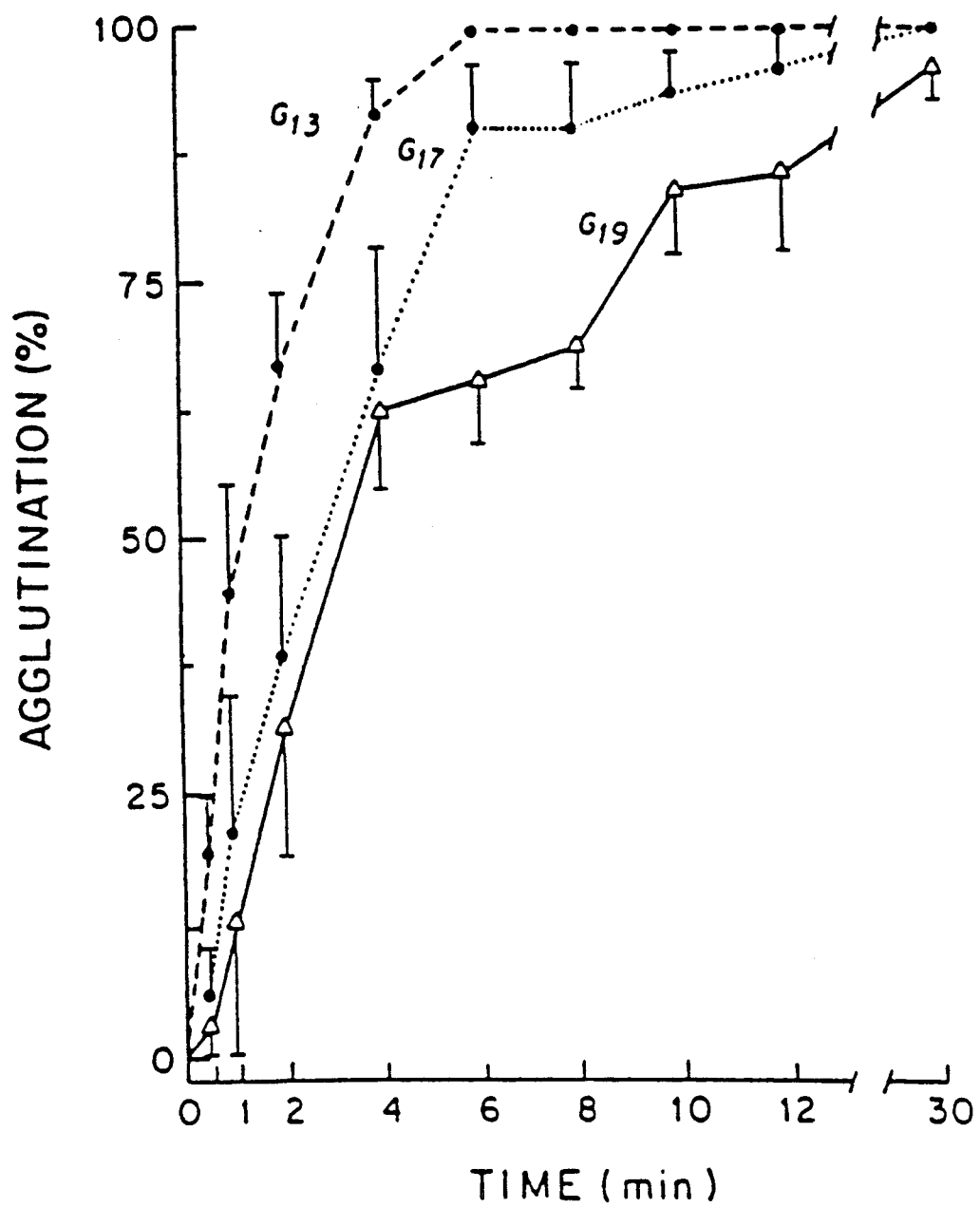

FIG. 9B. Agglutination of (G)$_n$-RGDF beads by PRP. The experiments were carried out with PRP and G$_{13}$-RGDF (n=9), G$_{17}$-RGDF (n=7), and G$_{19}$-RGDF (n=7) beads as indicated in the text. The values plotted are the mean±SEM.

Figure 10A:
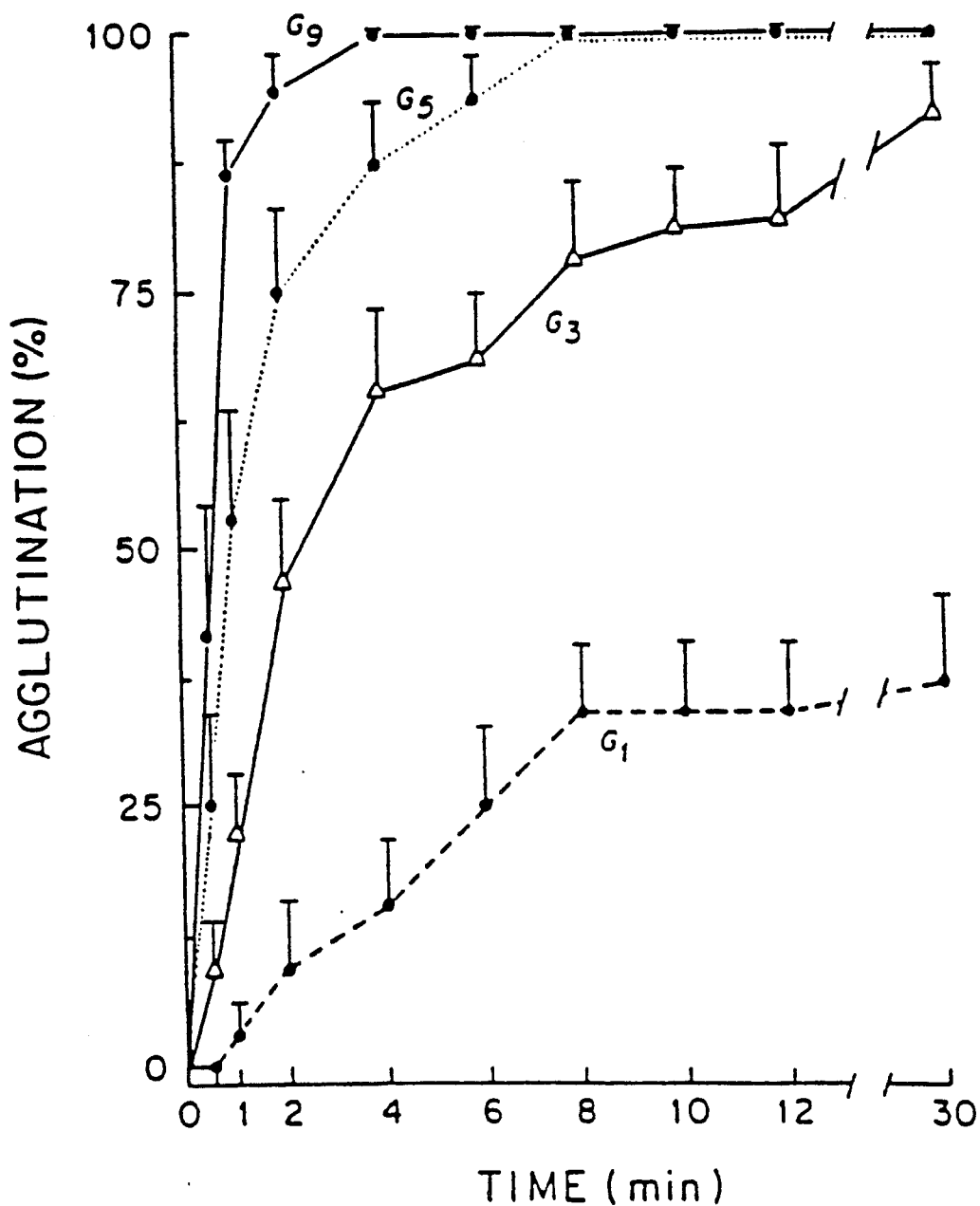

FIG. 10A. Agglutination of (G)$_n$-RGDF beads by PRP pretreated with ADP. PRP was incubated with ADP (6.7 μM) for 30 sec at 22° C. before adding G$_1$-RGDF (n=8), G$_3$-RGDF (n=7), G$_5$-RGPF (n=8), or G$_9$-RGDF (n=9) beads. The values plotted are the mean±SEM.

Figure 10B:
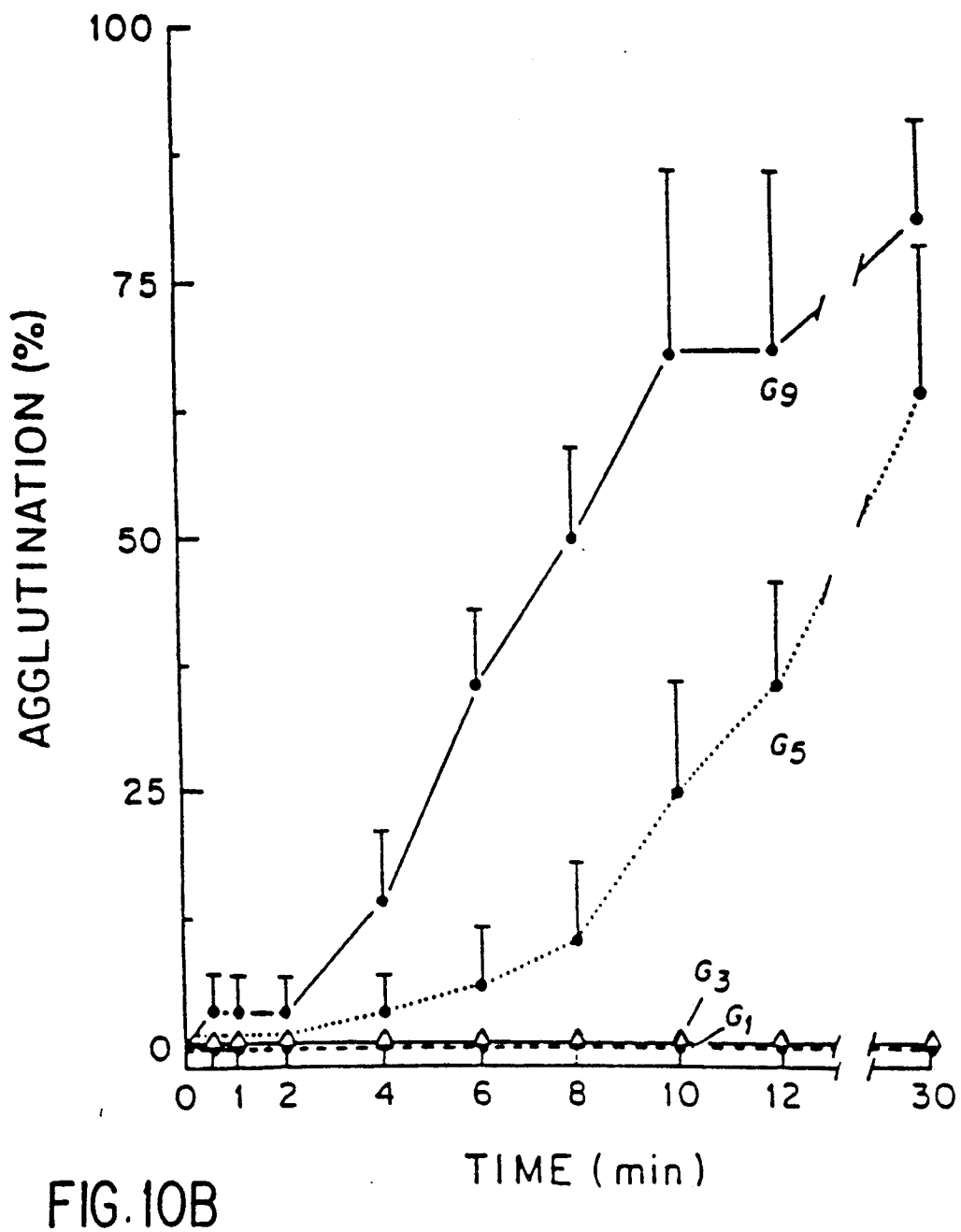

FIG. 10B. Agglutination of (G)$_n$-RGDF beads by PRP pretreated with PGE$_1$. PRP was incubated with PGE$_1$, (0.14 μM) for 30 min before adding G$_1$-RGDF (n=7), G$_3$-RGDF (n=7), G$_5$-RGDF (n=7), or G$_9$-RGDF (n=7) beads. The values plotted are the mean±SEM.

Figure 10C:
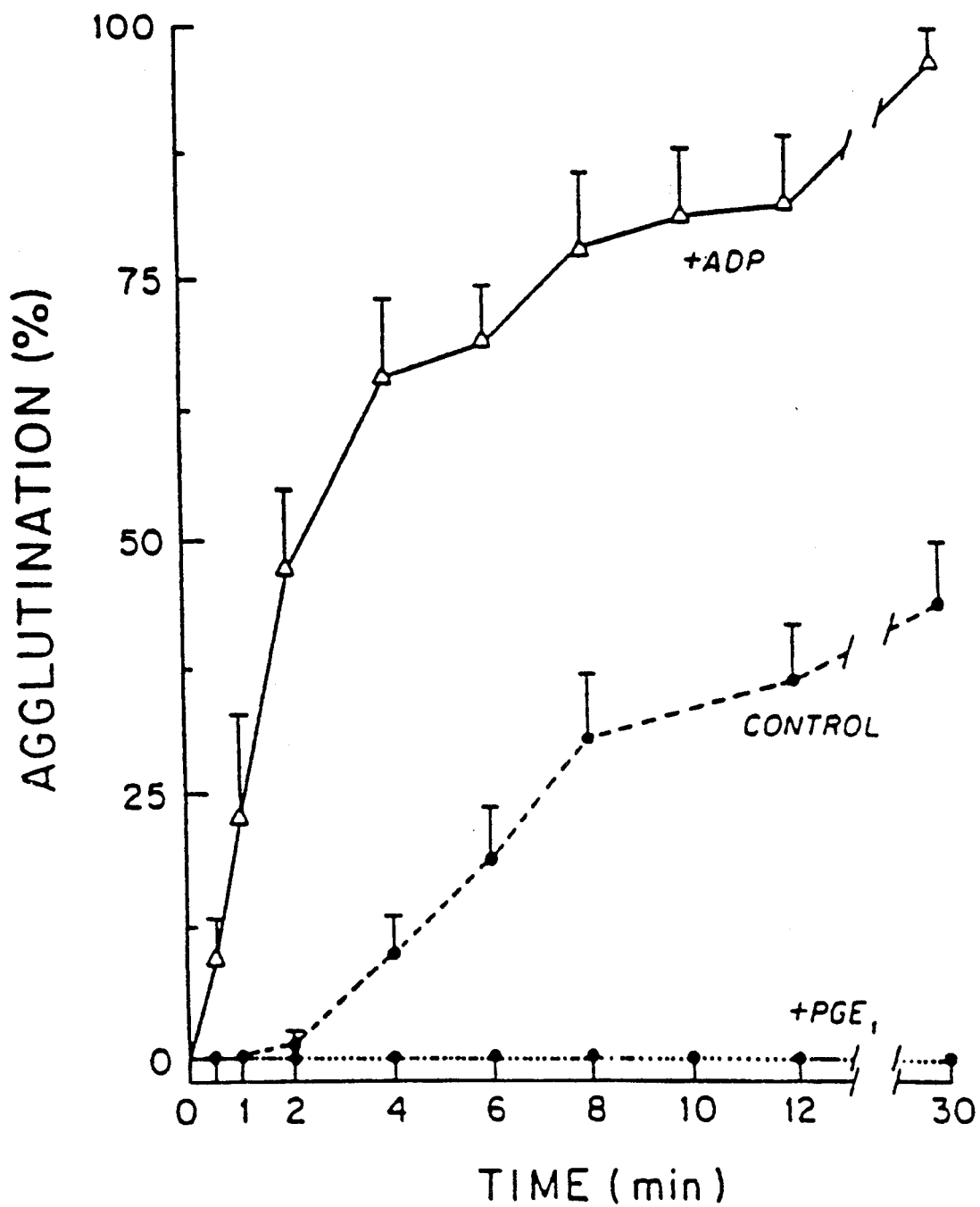

FIG. 10C. Agglutination of G$_3$-RGDF beads by native platelets, platelets pretreated with ADP, and platelets pretreated with PGE$_1$. Experiments were conducted as described in A and B above. The values plotted are the mean±SEM.

Figure 11A:
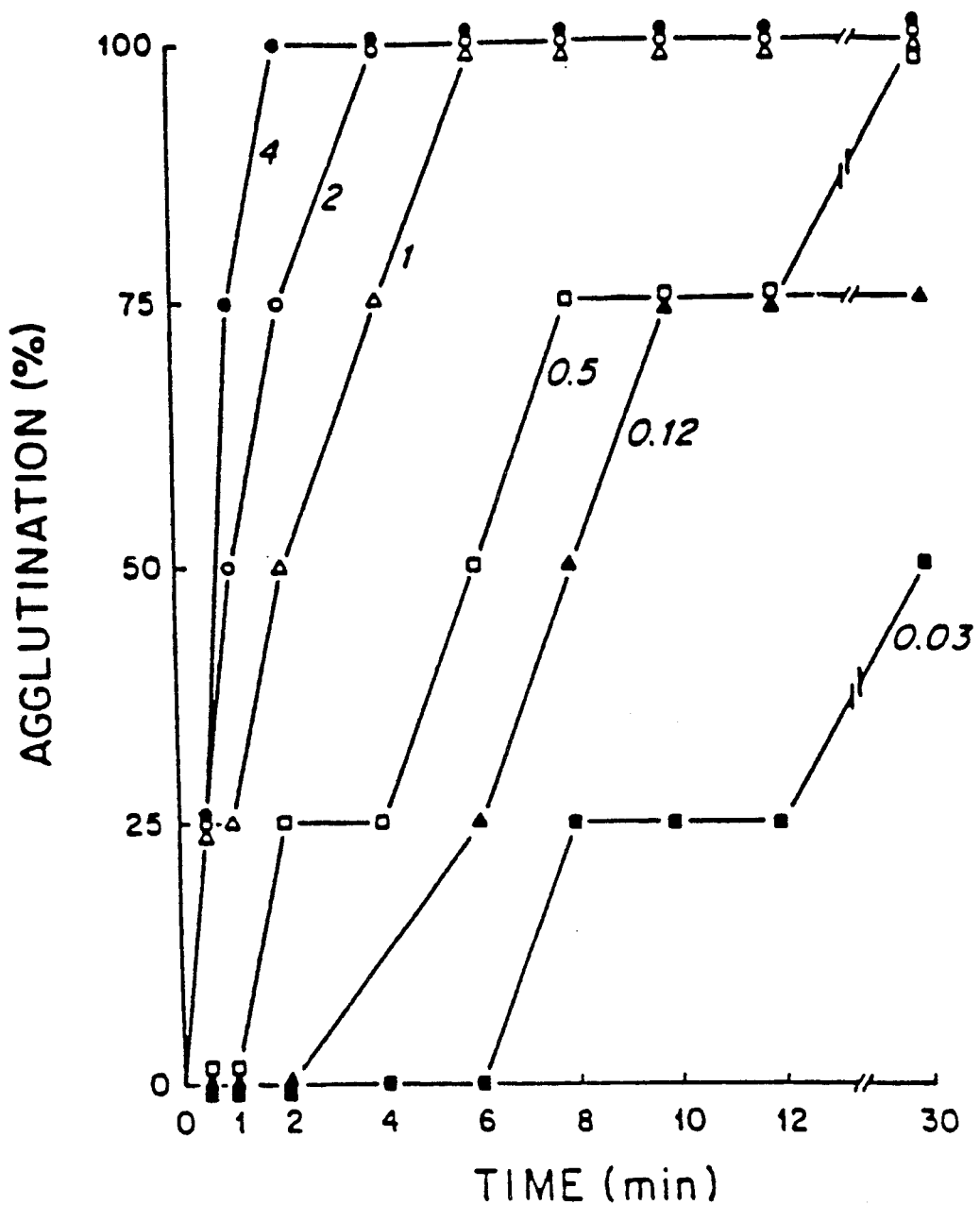

FIG. 11A. Effect of decreasing the bead surface density of (G)$_9$-RGDF peptides on agglutination by PRP. The G$_9$-RGDF peptide was coupled to beads at the different millimolar concentrations indicated on the graph. The efficiency of coupling was similar for all of the peptides (see Table IV for coupling efficiencies and Table V for maximal mean distances between peptides). The agglutination of the beads by PRP was then tested as indicated in the text. The values plotted are the results of a single experiment.

Figure 11B:
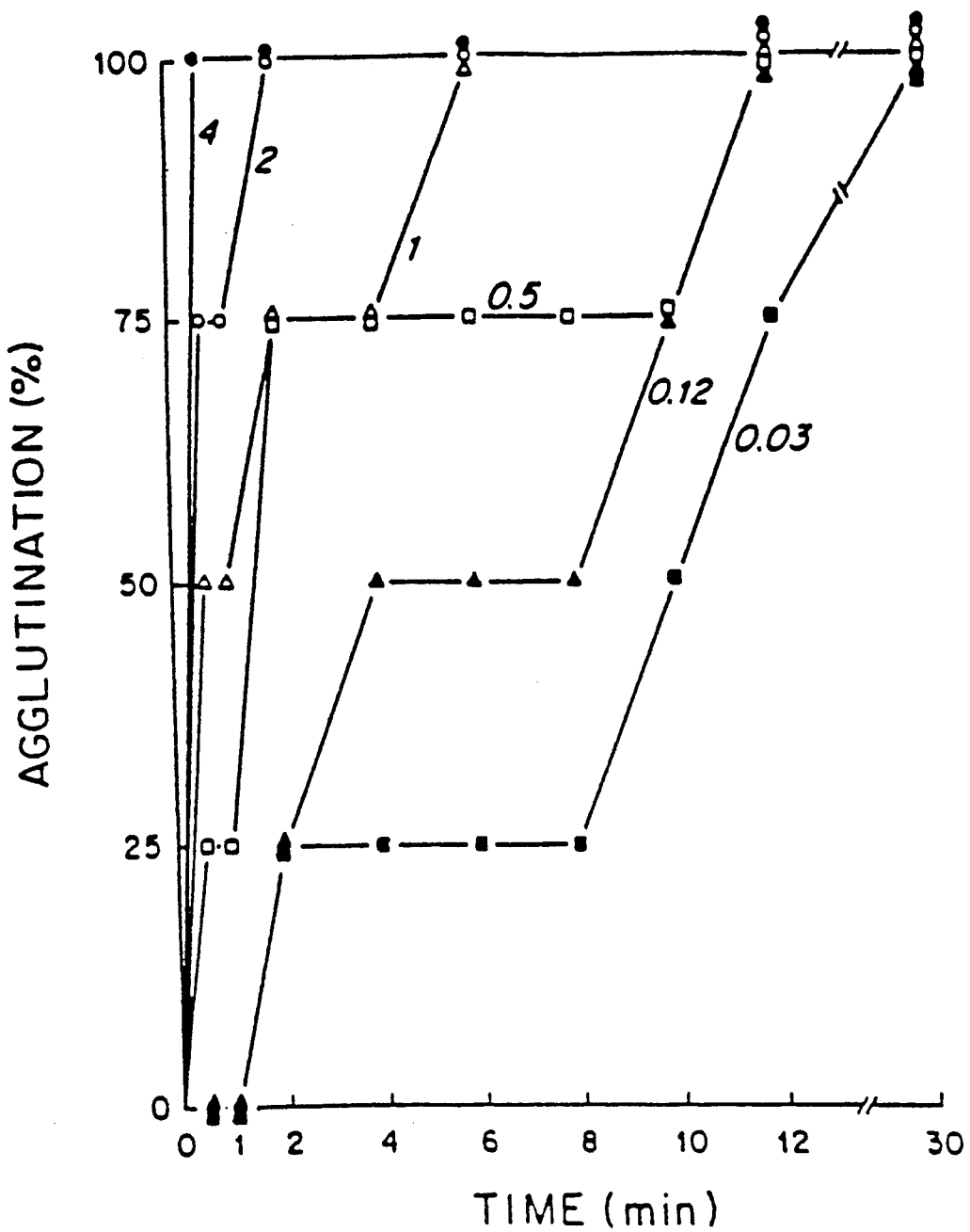

FIG. 11B. Effect of decreasing G$_9$-RGDF peptide density on agglutination by PRP pretreated with ADP. Experiment was conducted as indicated in A except that the PRP was pretreated with ADP (6.7 μM) for 30 sec at 22° C. before the beads were added. The values plotted are the results of a single experiment.

Figure 12:
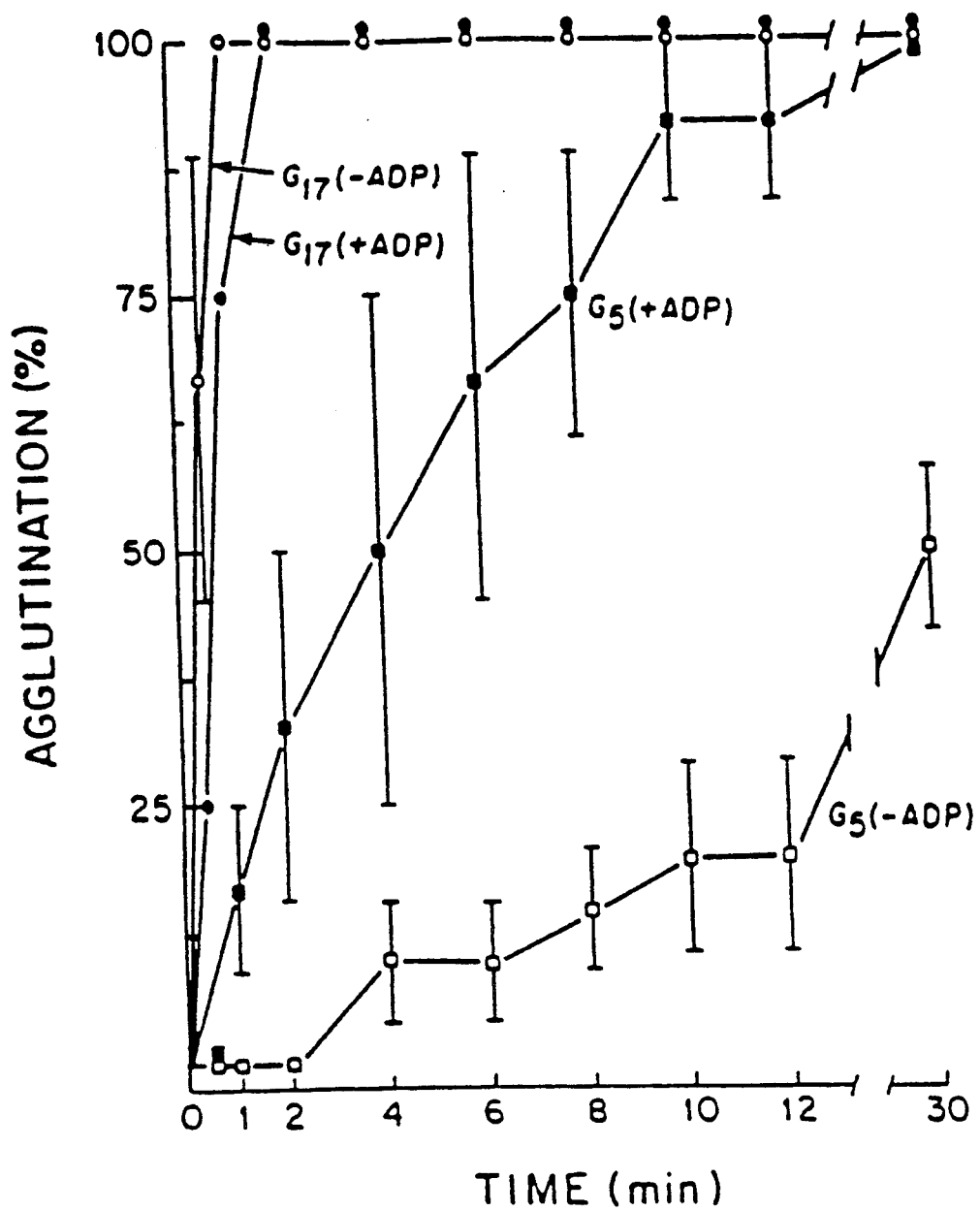

FIG. 12. Agglutination of G$_5$-RGDF and G$_{17}$-RGDF beads by gel-filtered platelets (GFP) in the presence and absence of ADP. Native GFP (70 μl) was reacted with either 5 μl of G$_5$-RGDF beads (n=5), or G$_{17}$-RGDF beads (n=3). In other experiments, the GFP was pretreated with ADP (6.7 μM) for 30 sec at 22° C. before adding the G$_5$-RGDF beads (n=3) or G$_{17}$-RGDF beads (n=2). The values plotted are mean±SEM.

Figure 13A:
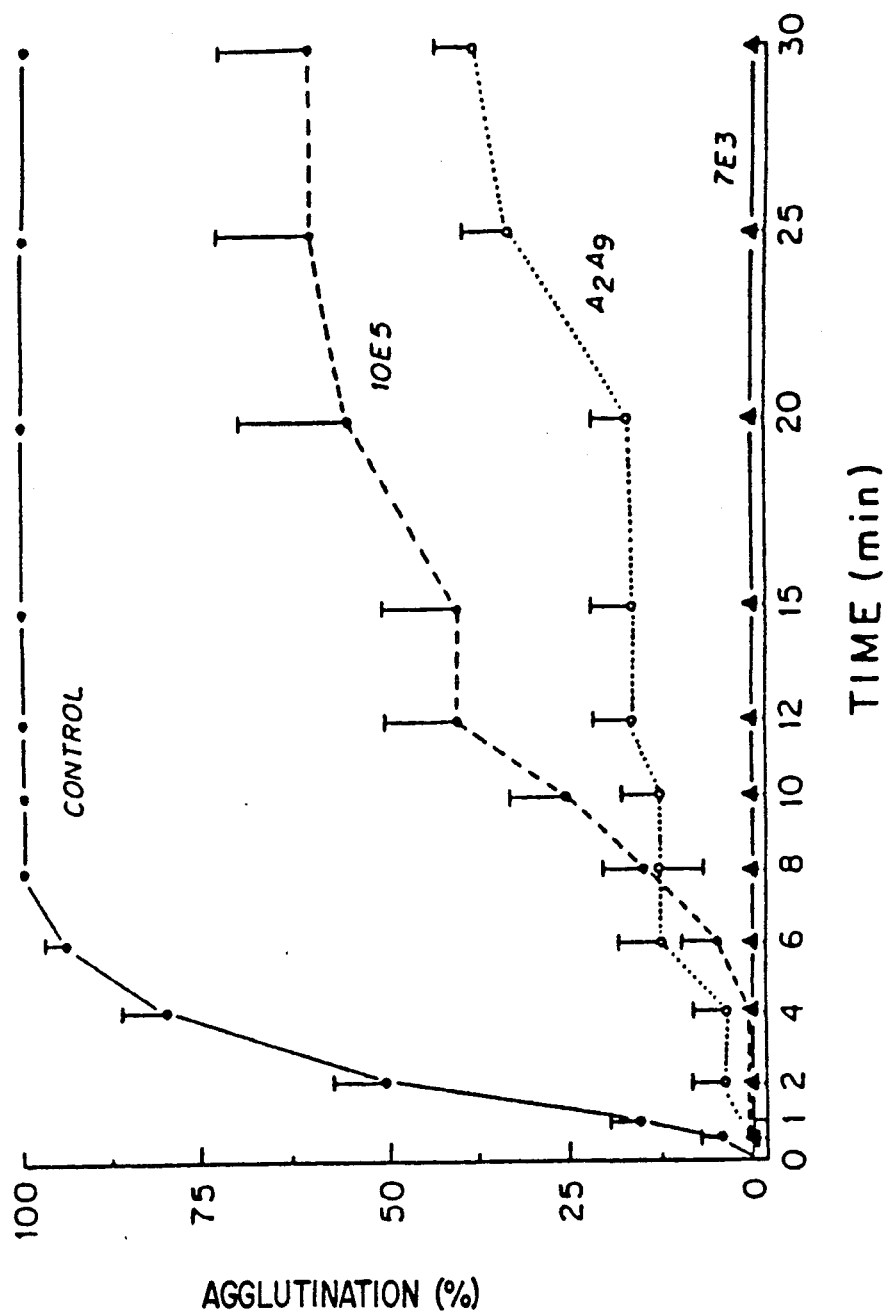

FIG. 13A. Agglutination of (G)$_9$-RGDF beads by PRP pretreated with monoclonal antibodies 10E5, A$_2$A$_9$, and 7E3. Experiments were carried out with PRP pretreated with 20 μg/ml 10E5 (n=5), 20 μg/ml A$_2$A$_9$ (n=5), or 20 μg/ml 7E3 (n=4) for 30–60 min. The values plotted are the mean±SEM.

Figure 13B:
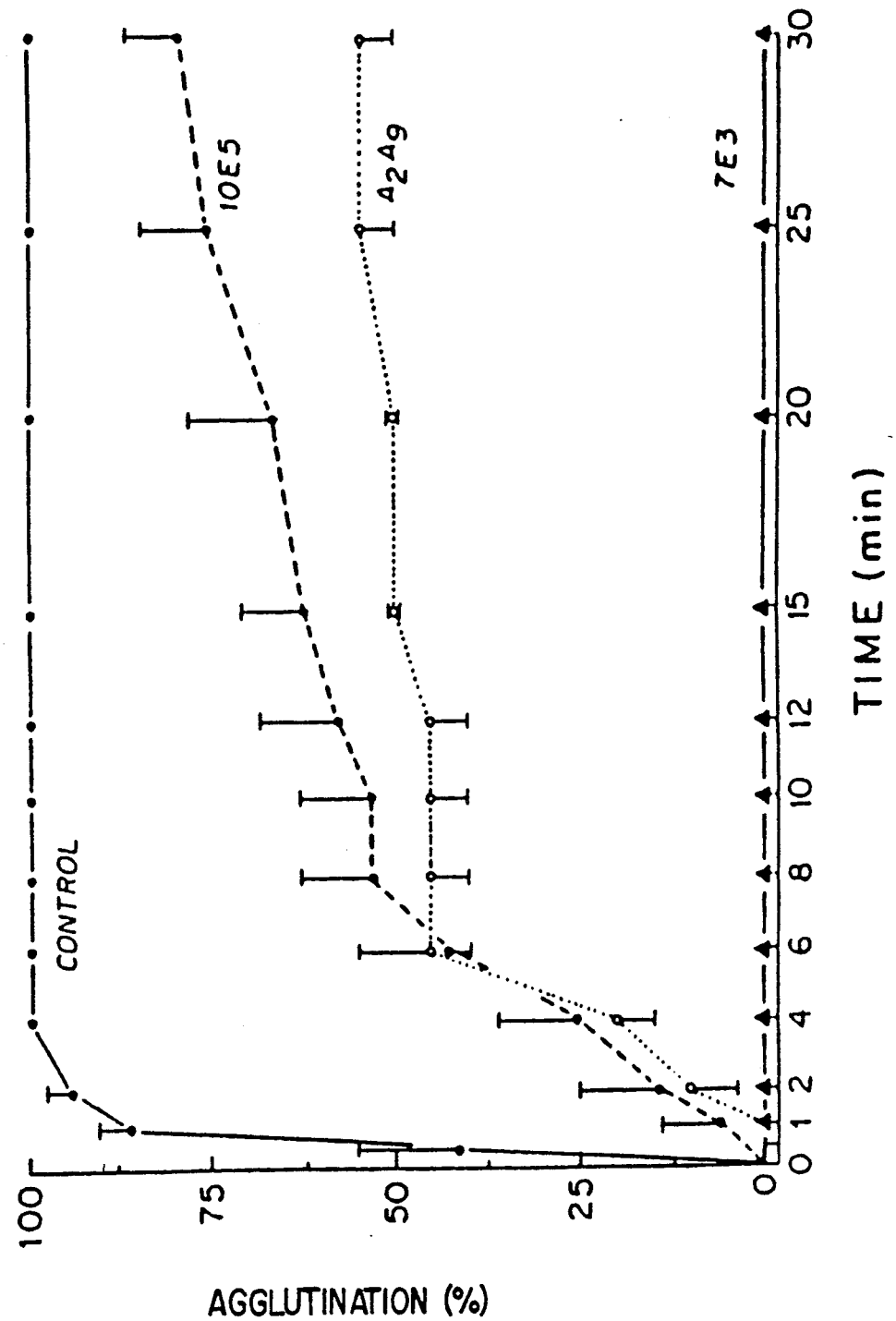

FIG. 13B. Agglutination of (G)$_9$-RGDF beads by PRP pretreated with monoclonal antibodies 10E5, A$_2$A$_9$, or 7E3, followed by preactivation with ADP. Experiments were carried out as in A except that the platelets were pretreated with ADP (6.7 μM) for 30 sec before adding the beads. The values plotted are the mean±SEM.

Figure 14:
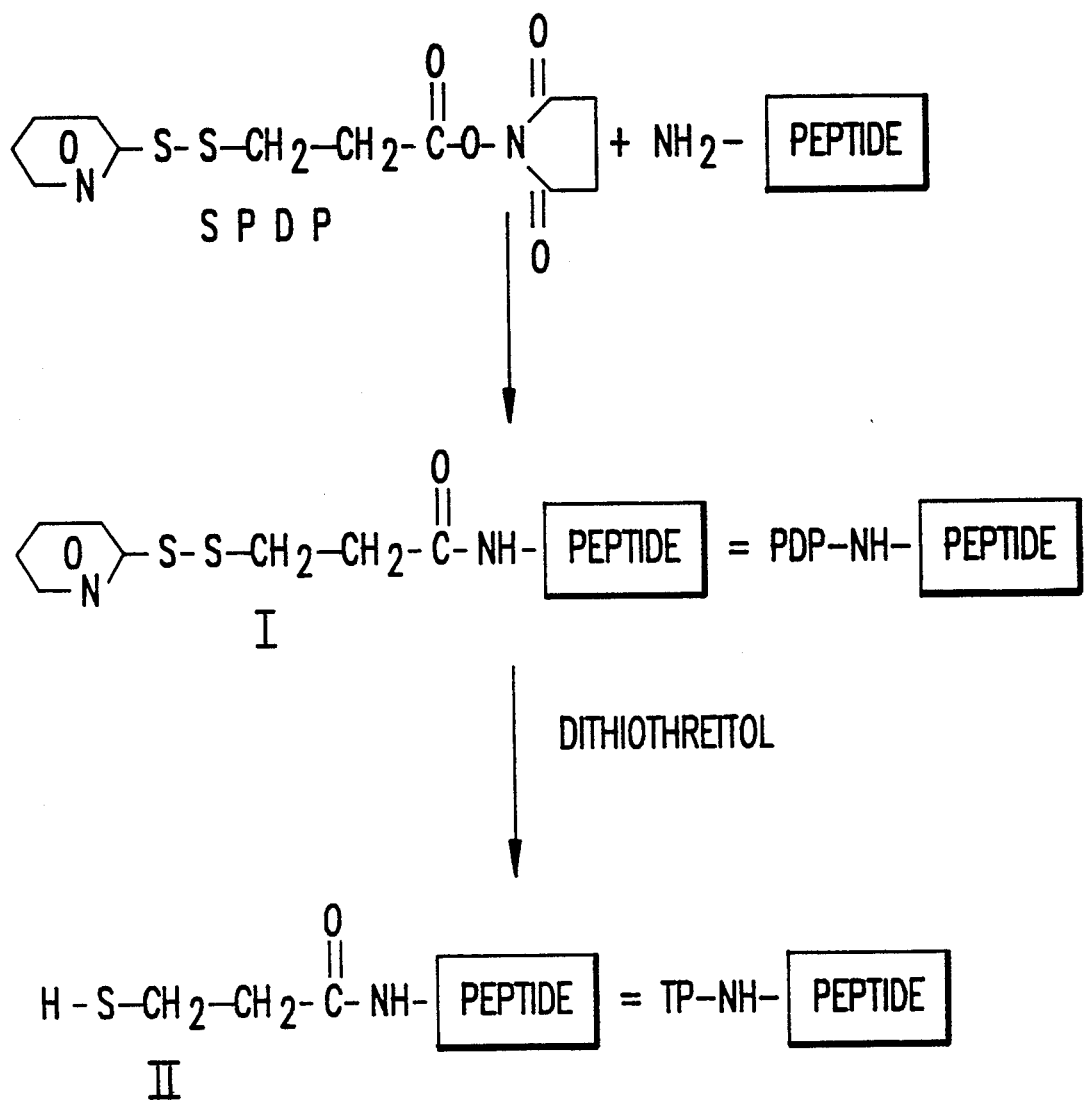
Figure 14:
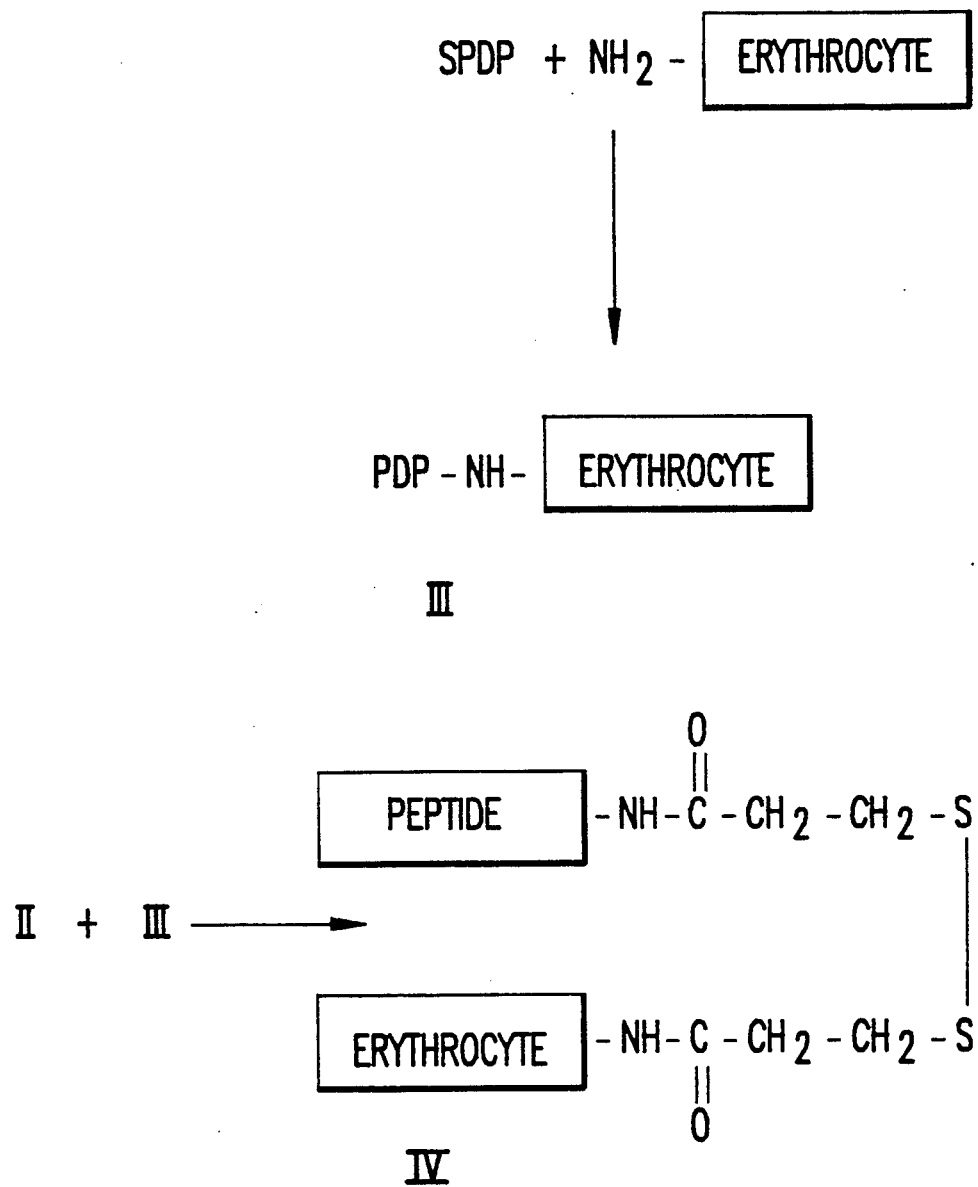

FIG. 14. Scheme 1: Preparation of thrombo-erythrocytes.

Figure 15:
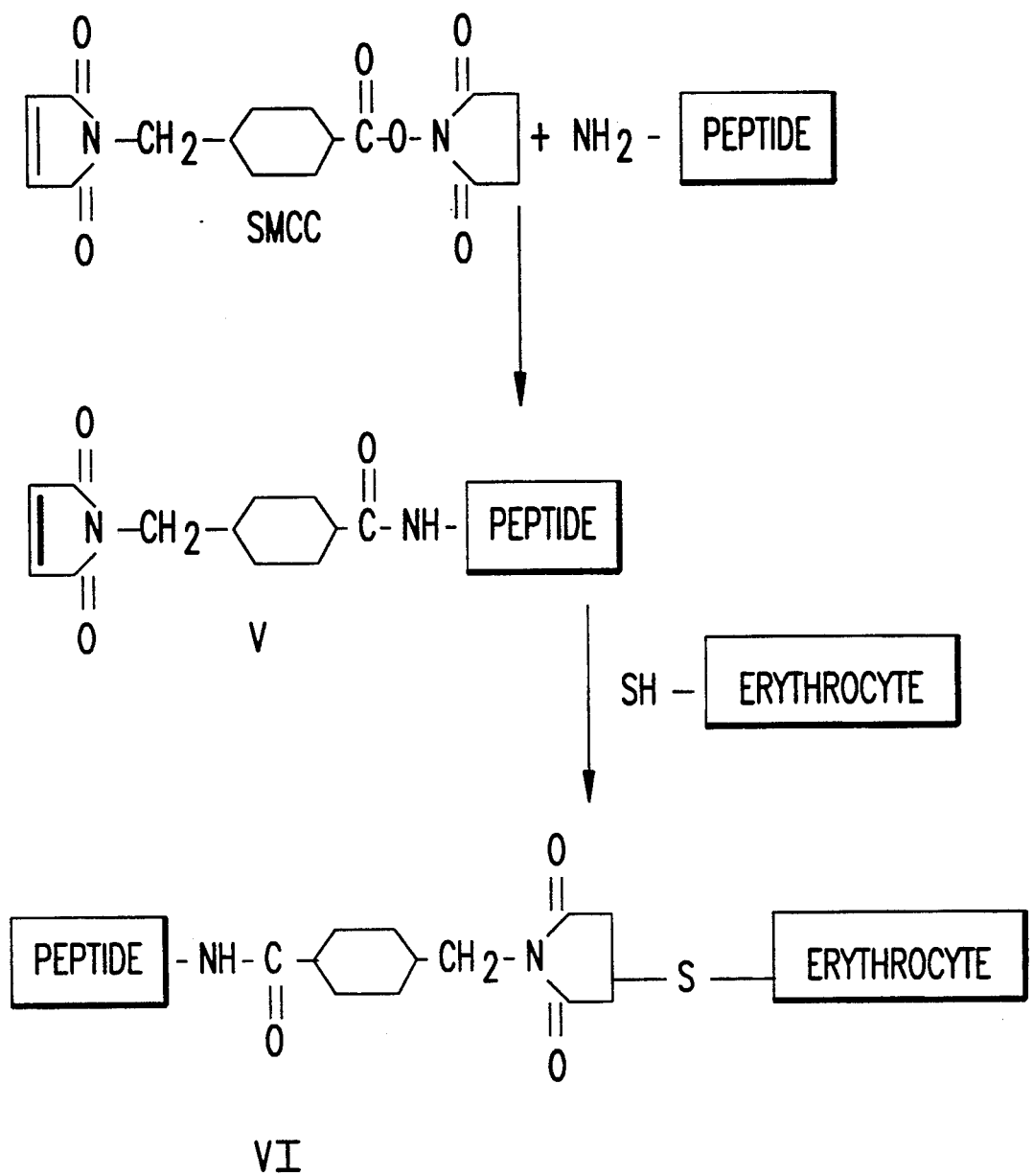

FIG. 15. Scheme 2: Preparation of thrombo-erythrocytes.

Figure 16:
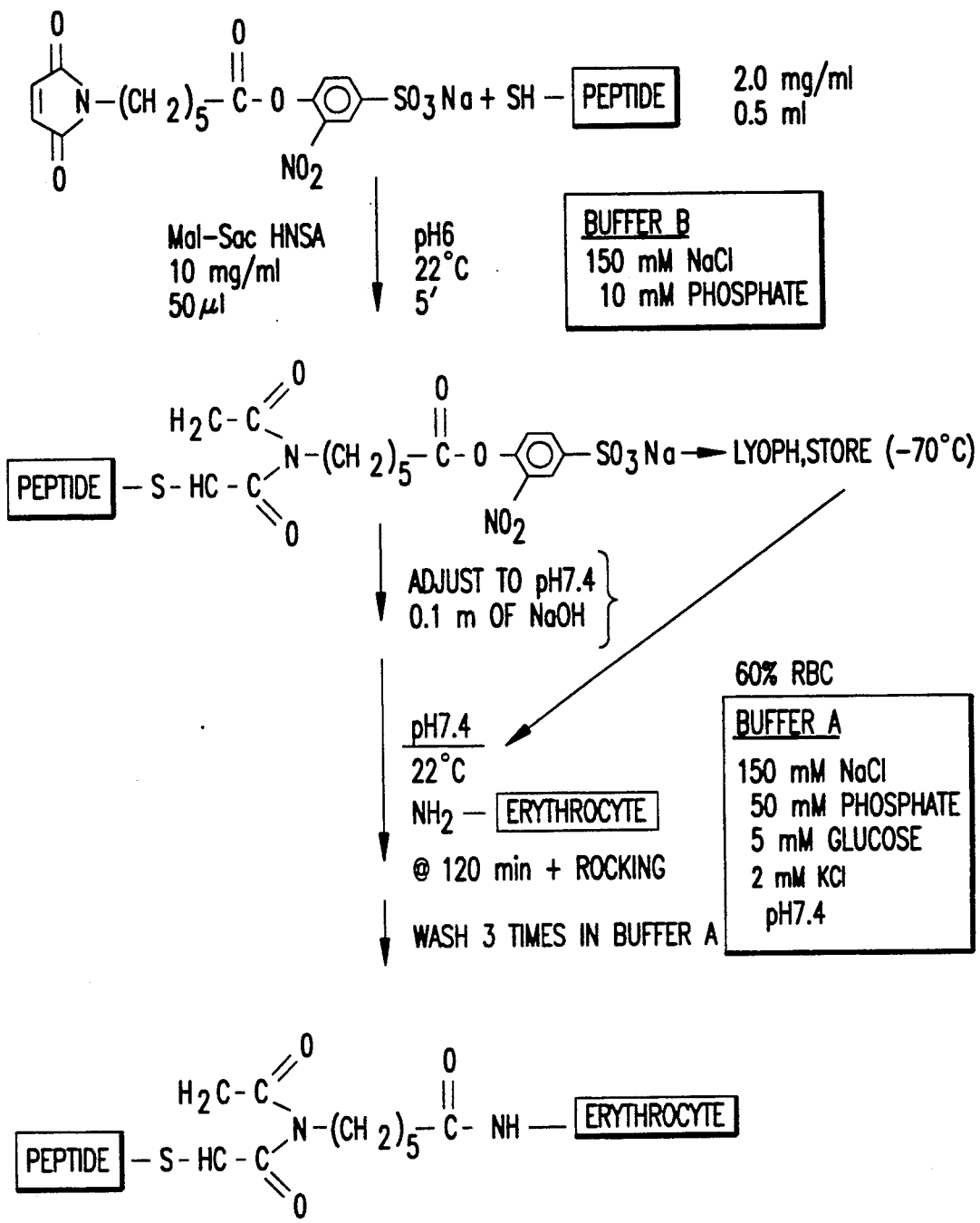

FIG. 16. Scheme 3: Two-step method for the preparation of thrombo-erythrocytes.

5. DETAILED DESCRIPTION OF THE INVENTION

The present invention relates to thrombo-erythrocytes, which are erythrocytes conjugated as provided herein to a RGD-containing peptide or polypeptide ("the RGD peptide"), and which are able to bind selectively to activated, but not to unactivated, platelets, causing co-aggregation of the activated platelets and thrombo-erythrocytes. This highly selective binding to activated platelets is in contrast to the behavior of RGD peptides in solution or long RGD peptides on the surface of beads, which bind to both activated and non-activated platelets with much less selectivity. The specificity of the thrombo-erythrocytes for activated platelets can be exhibited in vitro in the absence of an exogenous activating agent (see Section 8, infra). The thrombo-erythrocytes of the invention overcome the problems associated with prior art platelet substitutes by providing an abundant, safe material to promote platelet aggregation in vivo, specific for sites of injury. Thus, bleeding can be controlled, and hemorrhage can be prevented. In a preferred aspect involving the administration of autologous thrombo-erythrocytes, the possibility of infectious agent transmittal and adverse alloimmune reactions present in prior art methods are thus avoided.

The thrombo-erythrocytes bind to activated platelets via a specifically spaced R-G-D sequence in a peptide conjugated to the erythrocytes. The distance from the erythrocyte to the N-terminal end of Arg within the RGD peptide influences the binding profile, and is preferably about 9 to about 50 Angstroms, more preferably about 10 to about 40 Angstroms, and most preferably about 11 to about 25 Angstroms. The distance is estimated by considering the crosslinker and peptide sequence at the N-terminus of Arg as a linear molecule using standard bond lengths, assuming an extended conformation for the amino acids in the polypeptide. The distance represents the length of the segment from the covalent bond between the erythrocyte and linker molecule, including the bond length, to the N-terminal end of Arg in the RGD peptide.

Surprisingly, the thrombo-erythrocytes also exhibit rheological properties which do not significantly differ from those of untreated red blood cells. Furthermore, in a preferred aspect of the invention, the thrombo-erythrocytes surprisingly have the majority of the RGD peptides cross-linked to glycophorin A and glycophorin B on the erythrocyte cell surface. In this aspect, the specific binding to glycophorin provides important advantages because it is present in very high copy number on the erythrocyte surface (600,000 to 1 million per red blood cell), which allows highly effective binding of the RGD peptide-linker. Furthermore, since glycophorin has no definable role in erythrocyte physiology, it presumably can have the RGD-peptide linker bound to it without distortion of the erythrocyte's physiological or rheological properties.

In another embodiment of the invention, targeted thrombo-erythrocytes and targeted erythrocytes are provided, by conjugation of a targeting molecule such as an antibody or physiological ligand to the thrombo-erythrocytes or erythrocytes. In a preferred aspect, the targeted erythrocytes are carrier erythrocytes, which have been treated to release their contents (form erythrocyte "ghosts") and then incorporate an agent before resealing of their membrane, so that they can be used as in vivo delivery vehicles for their internalized agent. As used herein, the term "targeting molecule" refers to a molecule that can be conjugated to an erythrocyte (or thrombo-erythrocyte) and that binds specifically to a molecule found in vivo, such as a receptor or other recognition molecule or a molecule specific to a cell or cells, etc. In a specific embodiment, the targeting molecule is a peptide, e.g., a peptide containing the sequence Arg-Gly-Asp (R-G-D). In an embodiment where such a peptide is as described in Section 5.1.1 and has been conjugated to an erythrocyte as described in Section 5.1, resulting in the cell's retention of rheological properties and specificity for activated platelets, the cell is a targeted thrombo-erythrocyte. Such a targeted thrombo-erythrocyte will react with activated platelets in a thrombus, allowing imaging of the thrombus or the delivery of therapeutic agents to the thrombus. However, a targeted erythrocyte need not be a thrombo-erythrocyte. In another embodiment, the targeting molecule is an antibody, or fragment of an antibody, a lectin, asteroid or a carbohydrate. More than one targeting molecule can be used, for example, by using two different molecules to target an erythrocyte to the same in vivo location.

5.1. PREPARATION OF THE THROMBO-ERYTHROCYTES

In order to produce thrombo-erythrocytes, a polypeptide according to the present invention is prepared and covalently conjugated to an erythrocyte through a polyfunctional molecule according to methods described infra. However, it should be noted that upon completion of the conjugation reaction, the thrombo-erythrocytes should be tested for their unusual ability to retain both normal rheological properties and the platelet's specificity for forming thrombi at sites of vascular injury, i.e., for their ability to interact selectively with activated platelets. The lack of significant difference in the rheological properties displayed by the thrombo-erythrocytes of the invention and those of untreated erythrocytes can be observed by detecting a lack of significant difference between the thrombo-erythrocytes and untreated red blood cells in one or more of the following characteristics: surface/volume ratio, internal cell water, and/or membrane shear rigidity, as tested by laser diffraction ektacytometry as described in Example 8, infra, or by other methods known in the art. Examples of in vitro assays that can be used to demonstrate the ability of the thrombo-erythrocytes to bind selectively to activated platelets are described in Sections 8.1.5. and 8.1.8. infra). In a preferred aspect, the thrombo-erythrocytes of the invention are mainly conjugated via glycophorin A and glycophorin B on the cell surface, and have the ability, via their conjugated RGD peptides to interact with the GPIIb/IIIa receptor on activated platelets.

Certain mammals may provide the erythrocytes for preparation of thrombo-erythrocytes. Human and monkey erythrocytes are preferred for use, while baboon, dog, and rat erythrocytes do not appear to be useful. Erythrocytes may be purified and concentrated by methods that are known in the art. Typically, by way of example but not limitation, blood is removed from a patient and added to an anti-coagulant such as citrate. The blood is then centrifuged, and the plasma supernatant is removed with a pipet, leaving the erythrocytes. Buffer of about pH 6 to about pH 8 and about 0.15N ionic strength, preferably phosphate buffered saline (PBS), may be added and the mixture re-centrifuged to wash the erythrocytes. This process is repeated several times until the erythrocytes are sufficiently pure. However, to avoid damaging the erythrocytes, the washing steps are kept to a minimum.

The polypeptide and the erythrocytes are then each covalently bonded to a polyfunctional molecule. All operations are preferably performed in aqueous solution in order to avoid lysing the erythrocytes, which are sensitive to organic solvents. The pH should be between 6 and 8, preferably between 6.5 and 7.5.

It is preferable to use a heterobifunctional cross-linking reagent that reacts directly with each type of group. A heterobifunctional reagent that works well is Mal-Sac-HNSA (N-maleimido-6-aminocaproyl ester of 1-hydroxy-2-nitrobenzene-4-sulfonic acid sodium salt), which may be obtained from Bachem Biosciences, Inc., Philadelphia, Pa. Other cross-linking agents known in the art can be used, and are described in Section 5.1.2 infra, as long as the resultant cell is tested for the retention of rheological properties and specificity of binding to activated platelets associated with the thrombo-erythrocytes of the invention.

It was initially believed that the order of adding the RGD polypeptide and the erythrocyte to the polyfunctional molecule is not critical. Accordingly, initially the three components were simply combined in one reaction mixture, as illustrated in Section 6.

The dynamics of the one-step reaction described in Section 6 showed that the thrombo-erythrocytes of the present invention can be prepared and that they bind to activated platelets. However, the dynamics of the one-step reaction indicate that this one-step method is unpredictable. First, a sulfhydryl (thiol) group of the erythrocyte could react with the Mal-Sac-HNSA linker, rather than the desired reaction between the sulfhydryl (thiol) groups of the peptide and the Mal-Sac-HNSA linker. Cross-linking of erythrocyte cell-surface proteins would result. This potentially competing and undesirable reaction may damage the erythrocytes, and would make less linker available for binding to the peptide.

Accordingly, a more preferred two-step method was devised and tested, as shown in Scheme 3 (FIG. 16) and described in Section 7. In the preferred two-step method, the RGD polypeptide-linkers are prepared first separately, and then subsequently reacted with proteins on the erthrocyte. For example, this can be carried out as follows: the erythrocytes are maintained in a buffer solution at about pH 7.4. This prevents any osmotic damage to the erythrocytes. The polypeptide-linker is prepared separately at a pH of about 6.0. After conjugating the peptide sulfhydryl of the linker, the pH of the reaction solution is raised to a pH of about 7.4. The peptide-linker complex in solution at pH 7.4 can be added to an erythrocyte suspension, thus allowing free amino groups on the erythrocyte proteins to react with the second reactive group on the linker. The peptide linker complex can be lyophilized and stored for later use.

Alternatively, a peptide-linker complex is chemically synthesized by attaching the cross-linking group as a subsequent step after peptide synthesis, by standard chemical methods. This complex is suitable in the present invention as long as the linker which is attached to the peptide has an attachment point that is available for linking to reactive functional groups of the erythrocyte. In a specific aspect, the RGD peptide-linker intermediates can be stored for later use in conjugation to erythrocytes.

To ensure that the density of RGD peptides on the erythrocytes is high enough to support the reaction with platelets, the peptide must be added in great molar excess to the erythrocytes. For example, the molar excess of RGD peptides added to the erythrocytes should be approximately $0.5 \times 10^8$ to approximately $20 \times 10^8$, preferably approximately $1 \times 10^8$ to approximately $10 \times 10^8$ and more preferably approximately $3 \times 10^8$ to approximately $7 \times 10^8$. Preferably, the number of polypeptides attached to each erythrocyte should be approximately $0.05 \times 10^6$ preferably approximately $1 \times 10^6$ to approximately $20 \times 10^6$ although it is possible that as few as $0.01 \times 10^6$ attached polypeptides will yield a functional thrombo-erythrocyte.

Preferably, after the conjugation reaction is complete, excess cross-linker is removed by thorough washing. Additionally, albumin or autologous serum can be added during the washing procedure to react with any remaining reactive sites, and then be removed in the wash step.

The erythrocytes have both amino and sulfhydryl groups exposed on their surfaces. Either of these groups may be used to form the covalent bond to one of the functional groups of the polyfunctional molecule. Alternatively a carboxylic acid group can be used to form a covalent bond to one functional group of the polyfunctional molecule, e.g., via carbodiimide activation. Another functional group of the polyfunctional molecule is covalently bonded to the RGD peptide. Preferably, an amino group will usually form the bond to the polyfunctional molecule. In a specific aspect, when the site of attachment on the RGD peptide is cysteine, either the amino group or the sulfhydryl group may be bonded to the polyfunctional molecule. Where bonding is to the sulfhydryl group, the amino group should be protected, e.g., by acetylation.

5.1.1. The RGD Peptides of the Invention

The RGD peptide for conjugation to erythrocytes in accordance with the present invention includes a sequence of amino acids, preferably naturally occurring L-amino acids and glycine, having the following formula (I):

$$R_1\text{-Arg-Gly-Asp-}R_2 \qquad \text{I}$$

in which $R_1$ represents an amino acid or a sequence of more than one amino acid; in a specific embodiment, $R_1$ represents $XY(Z)_n$, in which X, Y and Z independently represent an amino acid; and n represents 0 or 1; $R_2$ represents OH or $NH_2$; or any amino acid; or a sequence of more than one amino acid. In a specific embodiment, $R_2$ represents an amino acid other than serine, threonine or cysteine or the amide thereof; in another specfic embodiment, $R_2$ is more than one amino acid, the first amino acid in the sequence, which is attached to asp, being other than serine, threonine or cysteine, or the amide of any free carboxyl groups.

In Formula I, $R_1$ and $R_2$ may be any amino acid or sequence thereof. The amino acids are preferably naturally occurring. The most common naturally-occurring amino acids are shown in Table I:

TABLE I

| NATURAL AMINO ACIDS AND THEIR ABBREVIATIONS | | |
|---|---|---|
| Name | 3-Letter Abbreviation | 1-Letter Abbreviation |
| (+)-Alanine | Ala | A |
| (+)-Arginine | Arg | R |
| (−)-Asparagine | Asn | N |
| (+)-Aspartic acid | Asp | D |
| (−)-Cysteine | Cys | C |
| (+)-Glutamic acid | Glu | E |
| (+)-Glutamine | Gln | Q |
| Glycine | Gly | G |
| (−)-Histidine | His | H |
| (+)-Isoleucine | Ile | I |
| (−)-Leucine | Leu | L |
| (+)-Lysine | Lys | K |
| (−)-Methionine | Met | M |
| (−)-Phenylalanine | Phe | F |
| (−)-Proline | Pro | P |
| (−)-Serine | Ser | S |
| (−)-Threonine | Thr | T |
| (−)-Tryptophan | Try | W |
| (−)-Tyrosine | Tyr | Y |
| (−)-Valine | Val | V |

However, $R_1$ and $R_2$ in Formula I are not limited to the 20 natural amino acids. In other embodiments, $R_1$ and $R_2$ can be non-classical amino acids or cyclic peptides or peptidomimetics (chemical peptide analogs). Non-classical amino acids include but are not limited to the D-isomers of the common amino acids, α-amino isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, Nα-methyl amino acids, and amino acid analogs in general.

Furthermore, the Arg and/or Asp in the RGD sequence can be the D (dextrarotary) or L (levorotary) amino acid.

In a specific embodiment, where $R_I$ is $XY(Z)_n$, X can be any amino acid, and specifically need not be valine. Preferably, X represents a naturally occurring amino acid, and most preferably cysteine or glycine. In a specific embodiment, Y can represent any amino acid, and specifically need not be threonine. Preferably Y represents a naturally occurring amino acid, and most preferably glycine. In a specific embodiment, Z can represent any amino acid, preferably a naturally occurring amino acid. Although Z preferably represents glycine, Z need not represent glycine when X represents valine and/or Y represents threonine.

As discussed above, $R_2$ can represent OH or $NH_2$. In another embodiment, $R_2$ may represent an amino acid, preferably a naturally occurring L-amino acid or glycine; in a specific embodiment, $R_2$ does not represent serine, threonine or cysteine or the amide thereof. In a preferred embodiment, $R_2$ represents phenylalanine or the amide of phenylalanine. In yet a further embodiment, $R_2$ can represent a sequence of more than one amino acid, in particular, the first amino acid in the sequence, which is attached to the carboxyl functional group of Asp, being other than serine, threonine or cysteine, or the amide of any free carboxyl groups in the sequence.

When $R_2$ is a sequence of amino acids, there is no necessary limitation on the number of amino acids in the sequence. Accordingly, the polypeptide for conjugation to erythrocytes can be any size, and encompasses what might otherwise be called an oligopeptide or a protein. Preferably, the polypeptide will have no more than about 1,000 amino acids.

When combined, $R_1$ and $R_2$ may represent a sequence of the amino acids discussed above. In a specific embodiment, $R_2$ is not serine, threonine or cysteine. For example, in a preferred embodiment, where $R_1$ is $XY(Z)_n$, X represents cysteine or glycine, Y represents glycine, and Z represents glycine. In a more preferred embodiment, X represents cysteine or glycine, Y represents glycine, Z represents glycine, and $R_2$ represents phenylalanine or the amide of phenylalanine. In the most preferred embodiment, X represents cysteine, Y represents glycine, Z represents glycine, and $R_2$ represents the amide of phenylalanine.

When $R_1$ is $XY(Z)_n$, X, Y, and Z may represent any tripeptide sequence. The tripeptide need not be Val-Tyr-Gly.

The polypeptide may be prepared by methods that are known in the art. For example, in brief, solid phase peptide synthesis consists of coupling the carboxyl group of the C-terminal amino acid to a resin and successively adding N-alpha protected amino acids. The protecting groups may be any known in the art or those described in Section 5.1.2 infra. Before each new amino acid is added to the growing chain, the protecting group of the previous amino acid added to the chain is removed. The coupling of amino acids to appropriate resins is described by Rivier et al., U.S. Pat. No. 4,244,946. Such solid phase syntheses have been described, for example, by Merrifield, 1964, *J. Am. Chem. Soc.* 85:2149; Vale et al., 1981, *Science* 213:1394–1397; Marki et al., 1981, *J. Am. Chem. Soc.* 103:3178 and in U.S. Pat. Nos. 4,305,872 and 4,316,891.

5.1.2. Crosslinking Agents

The polypeptide is conjugated to the erythrocytes through a polyfunctional molecule, i.e., a polyfunctional crosslinker. As used herein, the term "polyfunctional molecule" encompasses molecules having one functional group that can react more than one time in succession, such as formaldehyde (although formaldehyde is not indicated for use due to its potential carcinogenicity), as well as molecules with more than one reactive group. As used herein, the term "reactive group" refers to a functional group on the crosslinker that reacts with a functional group on a peptide, protein, or carbohydrate so as to form a covalent bond between the cross-linker and peptide or protein. The term "functional group" retains its standard meaning in organic chemistry. The polyfunctional molecules which can be used are biocompatible linkers, i.e., they are noncarcinogenic, nontoxic, and substantially non-immunogenic in vivo. Polyfunctional cross-linkers such as those known in the art and described herein can be readily tested in animal models to determine their biocompatibility. The polyfunctional molecule is preferably bifunctional. As used herein, the term "bifunctional molecule" refers to a molecule with two reactive groups. The bifunctional molecule may be heterobifunctional or homobifunctional. Preferably, the bifunctional molecule is heterobifunctional, allowing for vectorial conjugation of the RGD peptide and erythrocyte. It is particularly preferred for the polyfunctional molecule to be sufficiently soluble in water for reactions with the polypeptide and with the substrate to occur in aqueous solutions such as in aqueous solutions buffered at pH 6 to 8. Typically, the polyfunctional molecule covalently bonds with an amino or a sulfhydryl group on X of the polypeptide and on the surface of the erythrocytes. However, polyfunctional molecules reactive with other functional groups, such as carboxylic acids or hydroxyl groups, are contemplated in the present invention.

The homobifunctional molecules have at least two reactive functional groups, which are the same. The reactive functional groups on a homobifunctional molecule include, for example, aldehyde groups and active ester groups. Homobifunctional molecules having aldehyde groups include, for example, glutaraldehyde and subaraldehyde. The use of glutaraldehyde as a crosslinking agent was disclosed by Poznansky et al., *Science* 223, 1304–1306 (1984).

Homobifunctional molecules having at least two active ester units include esters of dicarboxylic acids and N-hydroxysuccinimide. Some examples of such N-succinimidyl esters include disuccinimidyl suberate and dithio-bis-(succinimidyl propionate), and their soluble bis-sulfonic acid and bis-sulfonate salts such as their sodium and potassium salts. These homobifunctional reagents are available from Pierce, Rockford, Ill.

The heterobifunctional molecules have at least two different reactive groups. The reactive groups react with different functional groups on the peptide and on a protein on the surface of the erythrocyte. These two different functional groups of the peptide and of the erythrocyte protein that react with the reactive group are usually an amino group, e.g., the epsilon amino group of lysine, and a sulfhydryl group, i.e., the thiol group of cysteine. However, the carboxylic acid and hydroxyl functional groups on the peptide and the erythrocyte protein can also react with the crosslinker.

When a reactive group of a heterobifunctional molecule forms a covalent bond with an amino group, the covalent bond will usually be an amido or imido bond. The reactive group that forms a covalent bond with amino groups may, for example, be an activated carboxylate group, a halocarbonyl group, or an ester group. The preferred halocarbonyl group is a chlorocarbonyl group. The ester groups are preferably reactive ester groups such as, for example, an N-hydroxy-succinimide ester group or that of Mal-Sac-HNSA.

The other functional group typically is either a thiol group, a group capable of being converted into a thiol group, or a group that forms a covalent bond with a thiol group. The covalent bond will usually be a thioether bond or a disulfide.

The reactive group that forms a covalent bond with a thiol group may, for example, be a double bond that reacts with thiol groups or an activated disulfide. A reactive group containing a double bond capable of reacting with a thiol group is the maleimido group, although others, such as acrylonitrile, are also possible. A reactive disulfide group may, for example, be a 2-pyridyldithio group or a 5,5'-dithio-bis-(2-nitrobenzoic acid) group.

Some examples of heterobifunctional reagents containing reactive disulfide bonds include N-succinimidyl 3-(2-pyridyl-dithio)propionate (Carlsson, et al., 1978, *Biochem J.*, 173:723–737), sodium S-4-succinimidyloxycarbonyl-alpha-methylbenzylthiosulfate, and 4-succinimidyloxycarbonyl-alpha-methyl-(2-pyridyldithio)-toluene. N-succinimidyl 3-(2-pyridyldithio)propionate is preferred. Some examples of heterobifunctional reagents comprising reactive groups having a double bond that reacts with a thiol group include succinimidyl 4-(N-maleimidomethyl)cyclohexahe-1-carboxylate and succinimidyl m-maleimidobenzoate.

Other heterobifunctional molecules include succinimidyl 3-(maleimido)propionate, sulfosuccinimidyl 4-(p-maleimido-phenyl)butyrate, sulfosuccinimidyl 4-(N-maleimidomethyl-cyclohexane)-1-carboxylate, maleimidobenzoyl-N-hydroxy-succinimide ester. The sodium sulfonate salt of succinimidyl m-maleimidobenzoate is preferred. Many of the above-mentioned heterobifunctional reagents and their sulfonate salts are available from Pierce.

Additional information regarding how to make and use these as well as other polyfunctional reagents may be obtained from the following publications or others available in the art:

Carlsson, J. et al., 1978, *Biochem. J.* 173:723–737.
Cumber, J. A. et al., 1985, *Methods in Enzymology* 112:207–224.
Jue, R. et al., 1978, *Biochem* 17:5399–5405.
Sun, T. T. et al., 1974, *Biochem.* 13:2334–2340.
Blattler, W. A. et al., 1985, *Biochem.* 24:1517–152.
Liu, F. T. et al., 1979, *Biochem.* 18:690–697.
Youle R. J. and Neville, D. M. Jr. , 1980, *Proc. Natl. Acad. Sci. U.S.A.* 77:5483–5486.
Lerner, R. A. et al., 1981, *Proc. Natl. Acad. Sci. U.S.A.* 78:3403–3407.
Jung, S. M. and Moroi, M., 1983, *Biochem. Biophys. Acta* 761:162.
Caulfield, M. P. et al., 1984, *Biochem.* 81:7772–7776.
Staros, J. V., 1982, *Biochem.* 21:3950–3955.
Yoshitake, S. et al., 1979, *Eur. J. Biochem.* 101:395–399.
Yoshitake, S. et al., 1982, *J. Biochem.* 92:1413–1424.
Pilch, P. F. and Czech, M. P., 1979, *J. Biol. Chem.* 254:3375–3381.
Novick, D. et al., 1987, *J. Biol. Chem.* 262:8483–8487.
Lomant, A. J. and Fairbanks, G., 1976, *J. Mol. Biol.* 4:243–261.
Hamada, H. and Tsuruo, T., 1987 , *Anal. Biochem.* 483–488.
Hashida, S. et al., 1984, *J. Applied Biochem.* 6:56–63.

Additionally, methods of cross-linking are reviewed by Means and Feeney, 1990, *Bioconjugate Chem.* 1:2–12.

Exemplary strategies for conjugating the peptide to the substrate through a heterobifunctional reagent are shown in schemes 1 and 2 (FIGS. 14 and 15, respectively) . In scheme 1, N-succinimidyl 3- (2-pyridyldithio)-propionate (SPDP) is treated with a RGD peptide. A free amino group on X of the polypeptide replaces the succinimidyloxy group and forms the corresponding 3-2-pyridyldithio)propionyl (PDP) amide. The 2-pyridyldithio group may be cleaved, for example, with dithiothreitol, forming the corresponding thiopropionyl (TP) amide (II). SPDP is then treated with an erythrocyte having at least one amino group, forming the corresponding PDP amide (III). Treatment of II, which has a free sulfhydryl group, with III, which has a group which forms a covalent bond with a sulfhydryl group, namely a pyridyldithio group, yields a compound wherein the peptide is covalently bonded to the substrate (erythrocyte-protein) through two polyfunctional molecules (IV).

In scheme 2, a polypeptide in accordance with the invention is treated with succinimidyl 4-(N-maleimidomethyl)cyclohexane-1-carboxylate (SMCC), forming the corresponding N-maleimidomethylcyclohexane-1-carboxylate amide (V). Reaction of V with the free sulfhydryl groups of an erythrocyte surface protein results in compound VI, wherein the peptide and the erythrocyte are covalently bonded through a polyfunctional molecule.

In a preferred aspect, Mal-Sac-HNSA is used, instead of SMCC.

It is also possible to bind a sulfhydryl group from the polypeptide of the invention to the polyfunctional reagent. This would occur when X represents cysteine. In such a case, the free amino group of the cysteine residue is protected if the polyfunctional molecule is a heterobifunctional molecule that reacts with amino groups as well as with sulfhydryl groups. The protecting group can be any of the large number of protecting groups known in the art. For example, an acetyl group can be added to the free amino group by treating the polypeptide with acetic anhydride. Alternatively, a carbobenzoxy group can be added by treating the polypeptide with carbobenzoxy chloride. Other N-protecting groups that are useful include the formyl, L-butoxycarbonyl-, trifluoroacetyl-, tosyl-, p-nitrocarbobenzoxy-, cyclopentyloxycarbonyl-, and phenoxycarbonyl- groups.

5.2. Use of Thrombo-Erythrocytes To Control Bleeding

The thrombo-erythrocytes of the invention may be used to control bleeding in vivo. In particular, the thrombo-erythrocytes may be used to control bleeding from small wounds in thrombocytopenic mammals, including humans. In a preferred aspect, the thrombo-erythrocytes are administered autologously to control bleeding. In a less preferred aspect, the administration is allogeneic.

In a specific embodiment, approximately 0.286–3.57 ml of blood per kg of the mammal is removed. The erythrocytes are then washed and concentrated. The washed erythrocytes are then covalently bonded to a RGD peptide through a polyfunctional molecule as described in Section 5.1, supra. The resulting thrombo-erythrocyte is then introduced into the mammal by means of standard transfusion techniques.

In one embodiment, the thrombo-erythrocytes of the invention are used in the treatment of thrombocytopenia, i.e., to augment a deficiency in platelet levels in a patient. In another embodiment, the thrombo-erythrocytes of the invention are introduced into a mammal, including a human, to help control bleeding, e.g., after trauma or during surgery.

The thrombo-erythrocytes for administration to a mammal are preferably formulated in a pharmaceutical composition, as described in Section 5.4, infra. The thrombo-erythrocytes can be administered to a mammal by intravenous or intra-arterial bolus injection or by intravenous drip. The number of thrombo-erythrocytes to be administered, i.e., the dose, depends upon the degree of thrombocytopenia in the mammal, and can be determined on a case-by-case basis by one skilled in the art. Preferably, the number of thrombo-erythrocytes augments the number of platelets in proportion to the amount absent from the thrombocytopenic individual relative to a normal individual.

5.3. Targeted Carrier Erythrocytes

According to the instant invention, erythrocytes, or in particular thrombo-erythrocytes, prepared in accordance with the present invention can be modified for delivery, to various target tissues, of labels or biologically active agents that have been incorporated into the erythrocytes (i.e. taken up by erythrocyte ghosts) to form carrier erythrocytes. In one embodiment, the carrier erythrocyte is a carrier thrombo-erythrocyte (i.e., a thrombo-erythrocyte whose intracellular contents have been replaced by a composition comprising a label or agent, and then whose membrane is resealed).

The carrier erythrocytes have advantages over liposomes by virtue of their larger size, which avoids the problem of non-specific endocytosis of liposomes by scavenging cells such as macrophages, and because of the presence of an extensive cytoskeleton, that, for example, protects the erythrocytes from complete osmotic lysis under hypotonic conditions. Moreover, the cell surface integral membrane proteins of erythrocytes provide a convenient scaffold for cross-linking targeting molecules. Most importantly, since erythrocytes are inherently biocompatible, the carrier erythrocytes are more likely also to be biocompatible.

5.3.1. Materials For Targeted Delivery

A large number of different molecules, macromolecules or macromolecular material can be incorporated in the carrier erythrocytes of the invention for delivery to a specific target.

In one embodiment, imaging agents can be incorporated in the carrier erythrocyte. Imaging agents include but are not limited to heavy metal contrast agents for x-ray imaging, magnetic resonance imaging agents, and radioactive nuclides (i.e., isotopes) for radio-imaging.

In another embodiment, the carrier erythrocyte can be loaded with one or more therapeutic agents. For example, and not by way of limitation, the therapeutic agent can be a chemotherapeutic, an enzyme, a neurotoxin, a growth factor, a neurotrophic factor, a hormone, a thrombolytic agent, or any drug. Generally, specific targeting of a drug to the site where it is needed results in more effective therapy because a larger therapeutic dose can be delivered than could be tolerated systemically. For example, larger doses of a chemotherapeutic can be delivered locally to a tumor than can be tolerated systemically by an organism, e.g., a human. In another example, a thrombolytic agent can be administered to the site of thrombosis in a concentration that would lead to uncontrollable bleeding if administered systemically.

In a further embodiment, the carrier erythrocyte can be loaded with nucleic acid sequences. For example, and not by way of limitation, the nucleic acids can be anti-sense RNA or DNA for delivery to a target cell. In another embodiment, the nucleic acids can be genetic information, such as a gene for gene therapy or an entire genome for fertilization. The carrier erythrocyte can be loaded with sperm, or fused with sperm to obtain the sperm haploid genome. In yet another embodiment, the carrier erythrocyte can contain plasmids, or modified virus or viral nucleic acids targeted for delivery.

5.3.2. Targeting Molecules

The instant invention provides for conjugating targeting molecules to the erythrocytes or erythrocyte ghosts. "Targeting molecule" as used herein shall mean a molecule which, when administered in vivo, localizes to desired location(s). The crosslinkers for the conjugation of peptides to erythrocytes described in Section 5.1.2, supra can be used to conjugate the targeting molecule to the erythrocyte; furthermore, carrier erythrocytes and carrier thrombo-erythrocytes need not retain the rheological properties of control red blood cells, in contrast to non-carrier thrombo-erythrocytes. The targeting molecule can be conjugated to the erythrocyte either prior to or subsequent to the introduction of a material into the carrier erythrocyte.

In various embodiments, the targeting molecule can be a peptide or protein, antibody, lectin, carbohydrate, or steroid. In one embodiment, the targeting molecule is a peptide ligand of a receptor on the target cell. In a specific embodiment, the targeting molecule is a peptide sequence described in Section 5.1.1, Supra, or variants thereof that bind RGD receptors on the surface of cells such as endothelial cells, cancer cells, or ova, e.g., human ova that have receptors that recognize the RGD sequence. In a specific embodiment directed to the use of carrier thrombo-erythrocytes, the targeting molecule is the peptide $R_1$-RGD-$R_2$ attached as described supra, and the erythrocyte targeting agent is loaded with a thrombolytic agent. Such a thrombo-erythrocyte is useful for the treatment of thrombosis, particularly since it is targeted to activated platelets.

In another embodiment, the targeting molecule is an antibody. Preferably, the targeting molecule is a monoclonal antibody. In one embodiment, to facilitate crosslinking to the erythrocyte, the antibody can be reduced to two heavy and light chain heterodimers, or the F(ab')$_2$ fragment can be reduced, and crosslinked to the erythrocyte via the reduced sulfhydryl. In another embodiment, the carbohydrate portion of the antibody can be directly, or via a derivative, utilized for attachment to the erythrocyte or thrombo-erythrocyte.

Antibodies for use as targeting molecule are specific for cell surface antigen. In one embodiment, the antigen is a receptor. For example, an antibody specific for a receptor on cancer cells, such as melanoma cells, can be used. In another embodiment, antibodies specific for leukocyte surface antigens, such as lymphocyte antigens, CD (clusters of differentiation) antigens, and receptors (e.g., T cell antigen receptors) can be conjugated to the erythrocyte ghosts. Any antibody known in the art that is specific for a cell antigen can be used as a targeting molecule.

In another embodiment, where a desired antibody is not available, the antibody can be prepared. Various procedures known in the art can be used for the production of antibodies specific for a target antigen that can be used to modify erythrocytes to prepare targeted erythrocytes. Such antibodies include but are not limited to polyclonal, monoclonal, chimeric, single chain, Fab fragments and an Fab expression library, although monoclonal antibodies or a fragment thereof are preferred. For the production of antibodies, various host animals, including but not limited to rabbits, mice, rats etc., may be immunized by injection with a target antigen marker. In one embodiment, target antigen is conjugated to an immunogenic carrier. In another embodiment, a target antigen epitope, e.g., a hapten, is conjugated to a carrier, such as keyhole limpet hemocyanin. As used herein, an "epitope" is a fragment of an antigen capable of specific immunoactivity, e.g., antibody binding. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as BCG (*bacille Calmette-Guerin*) and *Corynebacterium parvum*.

Monoclonal antibodies to a target antigen can be prepared by using any technique that provides for the production of antibody molecules by continuous cell lines in culture. These include but are not limited to the hybridoma technique originally described by Kohler and Milstein, (1975, *Nature* 256: 495–497), the more recent human B-cell hybridoma technique (Kozbor et al., 1983, *Immunology Today* 4:72) and the EBV-hybridoma technique (Cole et al., 1985, *Monoclonal Antibodies and Cancer Therapy*, Alan R. Liss, Inc., pp. 77–96). In an additional embodiment of the invention, monoclonal antibodies specific for a target antigen can be produced in germ-free animals utilizing recent technology (PCT/US90/02545). According to the invention, human antibodies can be used and can be obtained by using human hybridomas (Cote et al., 1983, *Proc. Natl. Acad. Sci., U.S.A.* 80:2026-2030) or by transforming human B cells with EBV virus in vitro (Cole et al., 1985, in *Monoclonal Antibodies and Cancer Therapy*, Alan R Liss, pp 77-96) In fact, according to the invention, techniques developed for the production of "chimeric antibodies" (Morrison et al., 1984, *Proc. Natl. Acad. Sci. U.S.A.* 81:6851-6855; Neuberger et al., 1984, *Nature* 312:604-608; Takeda et al., 1985, *Nature* 314:452-454) by splicing the genes from a mouse antibody molecule specific for target antigem together with genes from a human antibody molecule of appropriate biological activity can be used; such antibodies are within the scope of this invention.

According to the invention, techniques described for the production of single chain antibodies (U.S. Pat. No. 4,946,778) can be adapted to produce target antigen-specific single chain antibodies. An additional embodiment of the invention utilizes the techniques described for the construction of Fab expression libraries (Huse et al., 1989, *Science* 246:1275-1281) to allow rapid and easy identification of monoclonal Fab fragments with the desired specificity for target antigen.

Antibody fragments that contain sites specific for target antigen can be generated by known techniques. For example, such fragments include but are not limited to: the F(ab')$_2$ fragments, which can be produced by pepsin digestion of the antibody molecule and the Fab' fragments, which can be generated by reducing the disulfide bridges of the F(ab')$_2$ fragments. Preferably reduced fragments are used, since these can be conjugated to erythrocyte protein via their sulfhydryl groups.

This invention further provides for the use of other targeting molecules, such as lectins, carbohydrates, proteins and steroids, conjugated to erythrocytes.

5.3.3. Preparation of Carrier Erythrocytes

The key to the use of the present invention for targeting is the ability of red cells to be made temporarily "leaky". Making these modified erythrocytes leaky allows them to release their contents and take up the desired molecules, small cells such as sperm, viruses, drugs or altered genetic material; after which the erythrocytes may be resealed. As is well known to those skilled in the art, many modifications to and variations of this method can be used, and therefore it is intended that the present invention encompass all such variations.

Erythrocytes can be prepared as described in Section 5.1, supra. Any mammal can be the source of such erythrocytes. In order to incorporate molecules into erythrocytes for transport to selected target tissues, any procedure known in the art can be used to make the erythrocytes leak their contents (i.e., prepare erythrocyte ghosts) and then take up new molecules before being resealed. Such methods are described in the following references: (editorial), 1988, *Lancet* pp.1437-1438; Brearley et al., 1990, *J. Pharm. Pharmacol.* 42:297-301; Tonetti et al., 1990, *Biotech. Appl. Biochem.* 12:261-269; Updike and Rokania, 1983, *J. Lab. Clin. Med.* pp. 679-691; Ramsey et al., 1986, *Clin. Res.* 34:468A.

In one embodiment, by way of example but not limitation, the following procedure can be used:

Resealed erythrocytes are prepared by a gel-filtration method similar to that described by Kaplan in "Sodium pump-mediated ATP:ADP exchange: The sided effect of sodium and potassium ions", *Journal of General Physiology* 80:915-937 (1982); and "Sachs in Volume-sensitive K influx in human red cell ghosts, *Journal of General Physiology*, 92:685-711 (1988).

The modified cells are separated from plasma and washed with a 150 mM choline-chloride solution that contains 0.1 mM EDTA (ethylenediamine tetraacetic acid) and 10 mM PIPES (piperazine-N,N'-bis (2-ethanesulfonic acid) adjusted to pH 5.5 with Tris (Tris (hydroxymethyl) aminomethane). The cells are washed repeatedly until the pH of the cell suspension is 6.0. The cells are then brought to 50% hematocrit in the wash solution and stored on ice until run into a column.

The column is 45×10 cm and is filled with Bio Gel A50 beads (Bio Rad Inc., Rockville Center, N.Y.); the bed volume is 3.5 liters. The column is enclosed in a water jacket and maintained at about 1° C. The gel is equilibrated with a solution that contains 10 mM PIPES, 11.2 mM choline chloride, and 0.1 mM EDTA; the solution is adjusted to pH 6.0 with Tris (buffer A).

To prepare thrombo-erythrocyte ghosts, 200 ml of solution identical to buffer A except that the choline-chloride concentration is 150 mM (buffer B) is run into the column followed by 75-100 ml of cell suspension. The cells hemolyse (leak their content of hemoglobin and other materials) on the column and intracellular contents are retained by the beads. Ghosts are eluted with buffer B and collected on ice. They are concentrated by centrifugation (40,000 g for 10 min) and aspiration of the supernatant, collected in one or two tubes, and resuspended in buffer A. The ghosts are again centrifuged, the supernatant removed, and the ghosts distributed to resealing solutions. These contain 2% by volume (final volume including ghosts) of a 500 mM Tris HEPES (4-[2-hydroxymethyl]-1-piperazineethanesulfonic acid) solution (500 mM HEPES adjusted to pH 8.0 at 37° C. with Tris), 0.5 mM Tris EGTA (ethyleneglycol bis-[β-aminoethylether] N,N'-tetraacetic acid), 50 mg/100 ml albumin, and the molecules designed for incorporation into the thrombo-erythrocytes.

Ghosts account for 10–40% of the volume of the suspension. The ghost suspension is kept at 0° C. for 5 min and then incubated at 37° C. for 60 min. The resealed thrombo-erythrocyte ghosts are separated from the suspension by washing 3 times in 0.15M Nacl, 0.1M NAPO$_4$, 1 mg/ml human albumin, pH 7.4, and are then ready for use in vivo or in vitro.

Molecules to be introduced into carrier erythrocytes are discussed in Section 5.3.1.

In one embodiment, where it is desired to facilitate delivery of the molecule incorporated within the carrier erythrocyte, the lipid composition of the red blood cell can be manipulated by known methods to destabilize the cell membrane or treated by other methods (e.g., heating or removal of surface sialic acid residues) to reduce in vivo half-life of the carrier erythrocyte.

5.3.4. Administration of Targeted Carrier Erythrocytes

The present invention provides for administering the targeted carrier erythrocytes to a subject via any route known in the art. For example, the erythrocyte targeting agents can be administered via any route used to administer liposomes. In other embodiments, erythrocyte targeting agents can be administered intraventricularly, intraperitoneally, intramuscularly, subcutaneously, intravenously, and intraarterially, to mention but a few routes. Preferably, the administration is intravenously or intraarterially.

In a preferred embodiment, the targeted carrier erythrocytes are administered in a pharmaceutical composition comprising the targeted erythrocytes and a pharmaceutically acceptable carrier or excipient (see Section 5.4.1, infra).

5.4. Pharmaceutical Compositions Comprising Thrombo-Erythrocytes or Targeted Carrier Erythrocytes The present invention contemplates administering thrombo-erythrocytes or targeted carrier erythrocytes to a mammal, preferably in admixture with a pharmaceutically acceptable carrier or excipient. Such admixtures comprise a pharmaceutical composition of the invention.

A pharmaceutically acceptable carrier or excipient for use in the invention should comprise an aqueous solution having the following characteristics: pH of between about pH 6 and about pH 8; ionic strength of about 0.15N to maintain the appropriate osmotic environment for the modified erythrocytes; and physiological compatibility. The pharmaceutically acceptable carrier or excipient should not disrupt or solubilize the modified erythrocytes, e.g., contain oils, emulsifiers, detergents, or surfactants at concentrations lytic to the cell membrane.

Within the above parameters, the pharmaceutically acceptable carrier or excipient can comprise dextrose, glucose, starch, lactose and the like in aqueous solution or suspension.

6. EXAMPLE: PREPARATION AND TESTING OF THROMBO-ERYTHROCYTES

Blood (10 ml) was drawn from a human by syringe and a 19 gauge needle and placed into a polypropylene tube containing 0.1 ml 40% trisodium citrate. The blood was centrifuged at approximately 2,000×g for 10 min at 22° C. and the supernatant plasma removed. The erythrocyte pellet was washed three times with buffer A (0.15M NaCl, 0.05M phosphate, 5 mM glucose, 2 mM KCl, pH 7.4) by repetitive centrifugation at approximately 2,000 g for 10 min at 22° C. An aliquot of 0.5 ml of the washed erythrocytes in the same buffer at a concentration such that 60% of the volume was comprised of erythrocytes (60% hematocrit) was removed. The aliquot was mixed with 0.5 ml Buffer B (0.15M NaCl, 0.01M Na phosphate, pH 7.0) containing 2.9 mg/ml solution of the polypeptide:

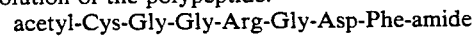
acetyl-Cys-Gly-Gly-Arg-Gly-Asp-Phe-amide

A 50 μl aliquot of 10 mg/ml Mal-Sac-HNSA (N-maleimido-6-aminocaproyl ester of 1-hydroxy-2-nitrobenzene-4-sulfonic acid sodium salt; Bachem Biosciences, Inc.; Philadelphia, Pa.) in buffer D was then added and the reaction allowed to proceed at 22° C. for 2 hr with rocking. After the incubation, 0.5 ml was removed and washed three times in buffer A. The resulting thrombo-erythrocytes were resuspended in buffer A to a hematocrit of 10%. A control sample of erythrocytes was treated identically but no peptide or Mal-Sac-HNSA was added.

The assay contained 50 μl of citrated platelet-rich plasma (prepared by centrifuging whole blood anticoagulated with 0.01 volume of trisodium citrate at 700×g for 3.5 min at 22° C. and adjusting the count to 3.0×10$^8$ platelets per ml with plasma free of platelets) and 5 μl of the thrombo-erythrocytes with, or without, adding 5 μl of adenosine diphosphate (ADP) (100 μM stock solution) to activate the platelets.

Agglutination of erythrocytes was graded from 1-4+ based on microscopic examination after rotating the samples in a microtiter plate at 260 rpm at 22° C. for various periods of time. At 2-3 min, the thrombo-erythrocytes produced 0-1+ agglutination in the absence of ADP and 4+ agglutination in the presence of ADP. These values remained unchanged for the remaining 6 min of observation. The control erythrocytes did not agglutinate.

7. EXAMPLE: TWO-STEP PROTOCOL FOR THE PREPARATION OF THROMBO-ERYTHROCYTES

The dynamics of the one-step reaction described in Example 6 illustrated that the thrombo-erythrocytes of the present invention can be prepared and that they bind to activated platelets. However, the dynamics of the one-step reaction provide reason for believing that this one-step method is at best unpredictable. First, the sulfhydryl (thiol) groups of the erythrocyte could react with the Mal-Sac-HNSA linker, rather than the desired reaction between the sulfhydryl (thiol) groups of the peptide and the Mal-Sac-HNSA linker. This potentially competing and undesirable reaction may damage the erythrocytes, and would make less linker available for binding to the peptide.

Accordingly, a more preferred two-step method was devised and tested, as shown in Scheme 3 (FIG. 16) and described herein.

Preparation of erythrocytes—Blood (10 ml) was drawn from a human by syringe and a 19 gauge needle and placed into a polypropylene tube containing 0.1 ml 40% trisodium citrate. The blood was centrifuged at approximately 2,000×g for 10 min at 22° C. and the supernatant plasma removed. The erythrocyte pellet was washed three times with buffer A (0.15M NaCl, 0.05M phosphate, 5 mM glucose, 2 mM KCl, pH 7.4) by repetitive centrifugation at approximately 700×g for 5 min at 22° C. An aliquot of 0.5 ml of the washed erythrocytes in the same buffer at a density such that 60% of the volume was comprised of erythrocytes (60% hematocrit) was removed.

Preparation of peptide—linker—A 0.5 aliquot of a solution of 2.0 mg/ml of the polypeptide with the formula shown in Section 6, supra, was prepared in buffer B (0.15M Nacl, 0.01M Na phosphate, pH 6.0). To this solution was added a 50 μl aliquot of 10 mg/ml Mal-Sac-HNSA (N-maleimido-6-aminocaproyl ester of 1-hydroxy-2-nitrobenzene-4-sulfonic acid sodium salt; Bachem Biosciences, Inc.; Philadelphia, Pa.) in buffer B. The reaction was allowed to proceed at 22° C. for 5 minutes at a pH of 6.0, thus forming the peptide-linker complex. The peptide-linker complex could be lyophilized and stored at approximately −70° C. for future use.

The peptide-linker complex was adjusted with a 0.1M solution of sodium hydroxide (NaOH) to a pH of 7.4. The 0.5 ml aliquot containing the linked peptide was added and mixed with the 0.5 ml aliquot of erythrocytes prepared as described above and the mixture was rocked for 120 minutes at 22° C. and pH of 7.4.

After the incubation, the thrombo-erythrocytes were washed three times in buffer A. The resulting thrombo-erythrocytes were resuspended in buffer A to a hematocrit of 10%. A control sample of erythrocytes were treated identically but no peptide or Mal-Sac-HNSA was added.

The assay contained 100 μl of citrated platelet-rich plasma (prepared by centrifuging whole blood anticoagulated with 0.01 volume of trisodium citrate at 700 g for 3.5 min at 22° C. and adjusting the count to $3.0 \times 10^8$ platelets per ml with plasma free of platelets) and 10 μl of the thrombo-erythrocytes with, or without, adding 10 μl of adenosine diphosphate (ADP) (100 μM stock solution) to activate the platelets.

Agglutination of erythrocytes was graded from 1–4+ based on microscopic examination after rotating the samples in a microtiter plate at 260 rpm at 22° C. for various periods of time. At 2–3 min, the thrombo-erythrocytes produced 0–1+ agglutination in the absence of ADP and 4+ agglutination in the presence of ADP. These values remained unchanged for the remaining 6 min of observation. The control erythrocytes did not agglutinate.

8. EXAMPLE: DETAILED CHARACTERIZATION OF THROMBO-ERYTHROCYTES

The present example shows that erythrocytes coated with RGD-containing peptides interact with platelets, and critically, that the interactions are selective for activated platelets, a prerequisite for diminishing the risks of indiscriminate thrombus formation.

8.1. MATERIALS AND METHODS

8.1.1. PEPTIDES

The peptide Ac-CGGRGDF-NH$_2$ was made on an automated peptide synthesizer (Applied Biosystems 430A; Foster City, Calif.) using t-boc chemistry and a 4-methylbenzhydrylamine resin. In 4 of the 5 syntheses, the coupling solvent was dimethylformamide, whereas in the fifth it was N-methyl-pyrrolidone. The protecting groups were β benzyl ester for the aspartic acid, tosyl for the arginine, and 4-methylbenzyl for the cysteine. Double couplings were performed with the phenylalanine in three of the syntheses and arginine in all of the syntheses. The amino-terminus was acetylated while the peptide was still on the resin by reaction with acetic anhydride. Cleavage of the peptide from the resin was accomplished with anhydrous HF in the presence of dimethylsulfide, parathiocresol, and anisole, starting at −10° C. After HF cleavage, the peptide-resin mixture was washed with ether alone (first 2 syntheses) or ether and dichloromethane (last 3 syntheses), and then extracted into acetic acid before lyophilization. HPLC analysis (C-8 column, 220 ×4.6 mm, Applied Biosystems 300 RP) demonstrated a single dominant peak in each synthesis representing 45–57% of the total absorbance at 220 nm. For some experiments the peptide was purified by HPLC before use. Fast atom bombardment mass spectrometry (xenon gun parameters: 7 kV, 1 mA, 0.4 mA ion current; mass spectrometer parameters: acceleration potential 6 kV, mass range 132–1172, resolution 1,500, scan speed 10 sec/decade; lyophilized sample transferred to glycerin or thioglycerin matrix) was performed on 2 of the 5 peptides and demonstrated that the peptides had the expected mass (751).

The peptide concentration for the coupling experiments was determined by titrating the free sulfhydryl groups with 5,5'-dithio-bis-(2-nitrobenzoic acid) (Ellman's reagent; Pierce Chemicals, Rockford, Ill.) using cysteine as a standard. A radiolabeled peptide was prepared by performing the peptide acetylation reaction (0.3 mg of resin) with 0.05 mmol (25 mCi) of $^3$H-acetic anhydride (Amersham Corp., Arlington Heights, Ill.) in a mixture of 4.75 ml dichloromethane and 0.25 ml diisopropyl ethylamine for 120 min at 22° C. with stirring and then adding 0.5 ml (5 mmol) unlabeled acetic anhydride for an additional 5 min. The resin was then allowed to float undisturbed, the infranatant fluid was removed, and 5 ml of 10% acetic anhydride (~5 mmol) in dichloromethane was added to the resin and allowed to react for another 5 min. The resin was then filtered, washed first in dichloromethane and then in methanol, and cleaved from the resin with HF in the presence of scavengers. The $^3$H-peptide had a specific activity of $1.3 \times 10^{11}$ dpm per mmol peptide. HPLC analysis demonstrated that 83% of the radioactivity eluted with the peptide peak.

8.1.2. Preparation of Thrombo-Erythrocytes

Preparation of thrombo-erythrocytes. The crosslinking strategy was: 1) to join the peptide to the heterobifunctional crosslinking agent N-maleimido-6 aminocaproyl ester of 1-hydroxy-2-nitrobenzene-4-sulfonic acid (mal-sac-HNSA; Bachem Bioscience, Bubendorf, Switzerland) via a reaction between the free sulfhydryl on the peptide and the crosslinker's maleimide moiety, and then, 2) to join the peptide-crosslinker to the erythrocyte via a reaction between the erythrocytes' amino groups and the aminocaproyl ester, resulting in the release of the highly absorbent 1-hydroxy-2-nitrobenzene-4-sulfonic acid dianion from the mal-sac-HNSA. In order to minimize hydrolysis of the ester during the maleimide-sulfhydryl reaction, a pH of 6.0 was chosen for the first reaction. To speed the reaction between the ester and the erythrocyte amino groups and to insure a physiological pH for the erythrocytes, a pH of 7.4 was chosen for the second reaction.

Whole blood was collected by syringe and placed in a polypropylene test tube containing either 0.1 ml 40% trisodium citrate or 1.2 ml CPDA-1 anticoagulant (89 mM trisodium citrate, 16 mM citric acid, 16 mM $NaH_2PO_4$, 160 mM dextrose, 2 mM adenine) so that the final volume was 10 ml. The blood was centrifuged at $700 \times g$ for 3.5 min at 22° C. for platelet-rich plasma (PRP). After removing the PRP, the blood was recentrifuged at $1600 \times g$ for 10 min at 22° C. and the resulting platelet-poor plasma (PPP) was removed. The buffy coat layer was then removed and discarded, and the erythrocytes were brought up to 50 ml with buffer A (140 mM NaCl, 5 mM KCl, 10 mM glucose, 10 mM Na phosphate, pH 7.4). The erythrocytes were then washed 3 times in buffer A and resuspended to a hematocrit of 10% in the same buffer. A 3 ml sample was transferred to a small polypropylene tube and centrifuged at $700 \times g$ for 5 min at 22° C.; 2.5 ml of the supernatant buffer was then removed, leaving 0.5 ml of a 60% hematocrit solution ($3.3 \times 10^9$ erythrocytes). In some experiments, a slightly different buffer was employed (150 mM NaCl, 50 mM Na phosphate, 2 mM KCl, 5 mM glucose, pH 7.4) and the results were the same.

The Ac-CGGRGDF-$NH_2$ peptide was then dissolved in buffer B (150 mM NaCl, 10 mM Na phosphate, pH 6.0) at ~2.0 mg/ml (2.6 mM) and the solution was readjusted to pH 6.0 with 1M NaOH. The mal-sac-HNSA was then dissolved at 10 mg/ml in buffer B, and 0.5 ml of the peptide solution (1.3 μmol) and 0.05 of the mal-sac-HNSA (1.1 μmol) were incubated at room temperature for 10 min. The pH of the solution was then increased to 7.4 with 0.1M NaOH, and the solution was immediately added to the 0.5 ml of erythrocytes in buffer A. The tube was then gently rocked at 22° C. for various periods of time, usually up to 2 hr, but in some cases 18 hr. In other experiments, the reaction took place in one step, with the peptide, crosslinker, and erythrocytes incubated together at pH 7.4–7.5. After the reaction was complete, the thrombo-erythrocytes were washed $\times 3$ in buffer A. Thrombo-erythrocytes were used immediately or stored at 4° C.

Preliminary studies monitored with Ellman's reagent (to assess the reaction between the maleimide group of mal-sac-HNSA and the sulfhydryl group on the peptide) indicated that when equimolar (2 mM) concentrations of crosslinker and peptide were used at pH 6.0, the maleimide-cysteine reaction was >95% complete within 5 min. These preliminary reactions were also monitored at 405 nm for release of the 1-hydroxy-2-nitrobenzene-4-sulfonic acid dianion from mal-sac-HNSA as an indicator of hydrolysis of the amino-reactive moiety on the crosslinker (Aldwin and Nitecki, 1987 *Anal. Biochem.* 164:494–501). At the end of these experiments, samples were treated with 0.05 volume of 5N NaOH, which produces complete release of the dianion (id.), to establish the percentage of total dianion that had been released during the reaction. The results indicated that less than ~1% of the amino-reactive groups on mal-sac-HNSA were hydrolyzed during the 10 min maleimide-cysteine reaction at pH 6.0.

8.1.3. Quantification of Peptide Binding

To determine the number of peptide molecules crosslinked to each thrombo-erythrocyte, the radiolabeled peptide was used in combination with unlabeled peptide. At selected time intervals, thrombo-erythrocytes were removed from the incubation mixtures, washed $\times 3$ in buffer A, and then subjected to hypotonic lysis to produce erythrocyte ghosts. This was accomplished by first incubating the erythrocytes with 10% buffer A (i.e., buffer A diluted to 10% of its original concentration) at 0° C., then centrifuging at 38,000 g for 20 min at 0° C., removing both the supernatant fluid and the hard red button of cell debris, resuspending the remaining pink ghosts in 1% cold buffer A, and washing $\times 2$ in cold 1% buffer A. In some experiments, 0.5 mM EDTA was added to the wash buffer to prevent resealing of erythrocyte ghosts. Finally, the erythrocyte ghosts were solubilized in 0.1–0.4 ml 1% sodium dodecyl sulfate (SDS), and this solution was added to 6 ml of scintillation fluid (Ultima Gold; Packard) and counted in a liquid scintillation counter (Packard 1900CA, Downers Grove, Ill.). The number of peptide molecules bound per erythrocyte was then calculated from the radioactivity specifically incorporated into the thrombo-erythrocytes [i.e., radioactivity associated with the ghosts after reaction with the full thrombo-erythrocyte incubation mixture (erythrocytes +peptide crosslinker) minus the radioactivity associated with the ghosts of the nonspecific control (erythrocytes+peptide)]. In one experiment, the 10% and 1% lysis buffers contained the protease inhibitors PMSF (1 mM), leupeptin (0.5 mM), and EDTA (0.5 mM). An extra, final wash in the 1% lysis buffer with just 0.5 mM EDTA was employed in this experiment because the ghosts were not easy to resuspend, and solubilization at 37° C. was achieved with a mixture of 200 μl 10% SDS +20 μl 0.1M NaOH+200 μl of a tissue solubilizer (TS-2, 0.5N; Research Products International, Mount Prospect, Ill.). The solubilized ghosts were then added to 18 ml of scintillation fluid and counted.

8.1.4. Identification of Erythrocyte Proteins To which Peptides are Crosslinked Pure $^3$H-peptide (1.3 μmol) was reacted for 120 min with erythrocytes in a 2-step reaction as described above. The thrombo-erythrocytes were then lysed using the cold, hypotonic buffers containing EDTA (0.5 mM), and the resulting ghosts were then dissolved in 100 μl 1.7% SDS at 15° C. and frozen at −80° C. A platelet-thrombo-erythrocyte co-aggregation assay (see below) on a sample removed before lysis demonstrated that the thrombo-erythrocytes were active in the assay. Subsequently, a 20 μl sample of the solubilized thrombo-erythrocytes was thawed, mixed with 20 μl of sample mixer and 2 μl of 2-mercaptoethanol, heated to 100° C. for 3 min, and electrophoresed in a polyacrylamide gel (3% stacking, 12.5% resolving gels) according to the method of Laemmli (1970, *Nature*, 227:680–682). The gel was then stained with the periodic acid-Schiff method by fixing overnight in 25% isopropanol-10% acetic acid, washing with 10% acetic acid, incubating with 1% periodic acid in 3% acetic acid for 60 min, washing with water $\times 4$, reacting with Schiff stain for 60 min in the dark, and washing with 1% $Na_2S_2O_5$ in 0.1M $HCl \times 3$. The gel was then stored overnight in 7% acetic acid at 4° C., photographed, stained with Coomassie blue, destained, and rephotographed. Finally, the gel was prepared for fluorography by fixing in 30% methanol, 10% acetic acid for 30 min×3, incubating in a precipitating reagent (solution A) of a fluorography preparation kit (Entensify, New England Nuclear Research Products, Boston, Mass.) for 30 min, and incubating in an aqueous fluorescent reagent (solution B) for 30 min. The gel was then dried and placed in a cassette with XAR-5 film (Eastman Kodak, Rochester, N.Y.) for 7 days at −70° C.

8.1.5. Platelet-Thromboerythrocyte Co-Aggregation Assay

To assess the ability of thrombo-erythrocytes to enter into developing platelet aggregates, a microtiter assay was developed. Platelet-rich plasma (PRP) was prepared from blood anticoagulated with 0.01 volume 40% sodium citrate and adjusted to a platelet count of $3.5 \times 10^8$/ml with platelet-poor plasma. Aliquots (50 or 100 μl) of the PRP were added to microtiter wells and then 5 or 10 μl of ADP (100 μM stock solution) was added to selected wells, followed by the addition of 5 or 10 μl of thrombo-erythrocytes (10% hematocrit in buffer A). The microtiter plate was then rotated at 270 rpm at 22° C. for variable periods of time between 0.5 and 20 min and the extent of platelet-thrombo-erythrocyte coaggregation was assessed visually on a scale from 0-4+ with the aid of a magnifying mirror. To assess the specificity of the reaction, in some experiments the PRP was preincubated with 10 mM EDTA, 300 μg/ml of the peptide RGDF, or 20 μg/ml of an antibody directed against both the GPIIb/IIIa receptor and the $\alpha_v\beta_3$ vitronectin receptor that blocks fibrinogen binding to activated platelets (7E3) (Coller, 1985, *J. Clin. Invest.* 76:101-108; Coller et al., 1991, *Blood* 77:75-83). Blood smears were made from the samples in some experiments and stained with a standard Wright stain (Hemastain, Geometric Data, Wayne, Pa.).

To obtain more quantitative data on the co-aggregation of thrombo-erythrocytes with platelets, the assay was adapted to the aggregometer. PRP was prepared from whole blood anticoagulated with ACD-A (8.5:1.5) and gel-filtered over a column of Sepharose 2B (Pharmacia) using a modified Tyrodes buffer (140 mM NaCl, 3 mM KCl, 12 mM NaHCO$_3$, 0.4 mM NaH$_2$PO$_4$, 10 mM HEPES, 2 mM MgCl$_2$, 0.2% bovine serum albumin, 5 mM glucose, pH 7.4). Samples consisted of 450 μl of gel-filtered platelets+20 μl of thrombo-erythrocytes (10% hematocrit) or control erythrocytes (i.e., erythrocytes incubated with peptide but no cross-linker). Maximal transmission was set with 450 μl of buffer+20 μl of control erythrocytes. Platelets were activated with ADP (4.3 μM final concentration) or epinephrine (10 μM).

8.1.6. Assessment of Hemolysis

Hemolysis of erythrocytes during thrombo-erythrocyte preparation was assayed by the reaction of any free hemoglobin with leucomalachite green (Kodak; 0.1% p,p'-benzylidenebis-(N,N-dimethylaniline) in 3.3 M acetic acid). The resulting compound was detected by absorbance at 617 nm, a wavelength that is not interfered with by the mal-sac-HNSA dianion. Standards were prepared by lysing known amounts of erythrocytes in deionized water. The assay consisted of 10 μl of sample (the supernatant of the reaction mixture after centrifuging to remove intact erythrocytes), 1 ml of leucomalachite green, and 1 ml of 0.1% H$_0$O$_2$. After 10 min the absorbance of each sample was read at 617 nm.

8.1.7. Osmotic Fragility

Thrombo-erythrocytes, control erythrocytes, and untreated erythrocytes were added to NaCl solutions of various concentrations. After 20 min at 22° C. the samples were centrifuged and the optical density of the supernatant fluid assessed at 540 nm. Results were expressed as the percent hemolysis, with 100% hemolysis defined as the optical density of a sample of erythrocytes added to water.

8.1.8. Binding of Thrombo-Erythrocytes To Platelets Adherent to Collagen

The first stage of the assay, involving the adhesion of platelets to purified type 1 rat skin collagen, was performed as described previously, but without radiolabeling the platelets (Coller et al., 1989, *Blood* 74:182-192). In brief, a sample of gel-filtered platelets (100 μl; $5.5 \times 10^8$/ml) in the presence of 2 mM MgCl$_2$ was added to microtiter plate wells precoated with collagen and the platelets were allowed to adhere for 1 hour at 22° C. The wells were then emptied and washed×3 with buffer (0.15M NaCl, 0.01M Tris/HCl, 0.5% bovine serum albumin, 5 mM glucose, pH 7.4). Control erythrocytes or thrombo-erythrocytes (50 μl; 10% hematocrit) were then added to the wells in the same buffer, which was now supplemented with 2 mM MgCl$_2$. After 60 min, the wells were emptied and washed×3 as above. The wells were then visually inspected at 400× magnification with the aid of a microscope with Nomarski optics. The effect of 20 μg/ml of an antibody to GPIIb/IIIa that blocks fibrinogen binding and platelet aggregation (10E5) (Coller et al., 1983, *J. Clin. Invest.* 72:325-338) and 400 μg/ml of the peptide RGDF on thrombo-erythrocyte adhesion to platelets was tested by adding these agents to the thrombo-erythrocytes immediately before the thrombo-erythrocytes were added to the microtiter wells.

8.1.9. Assessment of Thrombo-Erythrocyte Volume and Surface Properties

Laser diffraction ektacytometry was performed on the thrombo-erythrocytes and control erythrocytes essentially as previously described (Mohandas et al., 1980, *J. Clin. Invest.* 66:563-579; Clarck et al., 1983, *Blood* 61:899-910) using samples sent by overnight mail on 4° C. cold packs from Stony Brook to Berkeley. Control erythrocytes or thrombo-erythrocytes (20 μl of a ~33% suspension in 0.15M NaCl, 0.01M Tris/HCl, 5 mM KCl, 10 mM glucose, 1% bovine serum albumin, pH 7.4 buffer) were added to 3.5 ml of 4% (w/v) polyvinyl pyrrolidone in phosphate buffered NaCl adjusted to 290 mOsm (viscosity=22 cp). The samples were then placed in the instrument and the deformability index (a measure of the change in cell shape from circle to ellipse) was measured continuously as the cells were subjected to increasing shear rates (0–1,037 s$^{-1}$).

8.2. RESULTS

8.2.1. Characterization of Thrombo-Erythrocytes

The supernatant fluid after performing the thrombo-erythrocyte reaction had 0.40±0.09% (mean−SD; n=6) erythrocyte hemolysis compared with 0.13±0.04% (n=6) in the control reaction. Studies of osmotic fragility showed only minor differences between thrombo-erythrocytes and control erythrocytes (FIG. 1 contains data on 3 separate experiments), and the control erythrocytes did not differ from untreated erythrocytes. Laser ektacytometry demonstrated that the thrombo-erythrocytes had the same deformability properties as did control erythrocytes and untreated erythrocytes (FIG. 2). Both control erythrocytes and thrombo-erythrocytes had plateau values that were within the normal range determined from studies on more than 200 individuals (0.6±0.02; mean±SD).

8.2.2. Studies with the $^3$H-Peptide

The results of 5 separate experiments to determine the number of peptide molecules that bound per thrombo-erythrocyte are shown in Table II.

TABLE II

Binding of $^3$H-CGGRGDF Peptide to Erythrocytes

| Experiment | 1 Step or 2 Step | $^3$H-Peptide (μmol)* | Mal—Sac-HNSA (μmol)* | Number of Peptide Molecules Bound Per Thrombo-Erythrocyte Time (min) | | | |
|---|---|---|---|---|---|---|---|
| | | | | 30 | 60 | 90 | 120 |
| 1 | 1 | 0.9 | 1.1 | | | | 570,000 |
| 2 | 1 | 1.3 | 1.1 | 780,000 | 1,100,000 | 1,400,000 | 1,400,000 |
| 3 | 1 | 1.3 | 1.1 | | 750,000 | | |
| | 2 | 0.6 | 0.55 | | 480,000 | 570,000 | |
| | 2 | 1.3 | 1.1 | 540,000 | 750,000 | 870,000 | 1,100,000 |
| 4 | 2 | 1.3 | 1.1 | | | | 1,000,000 |
| 5 | 2 | 1.3 | 1.1 | | | | 500,000 |

*The number of μmol of the $^3$H-CGGRGDF peptide and the crosslinking reagent (mal—sac-HNSA) employed in the reactions are indicated. Each reaction mixture contained ~3.3 × 10$^9$ erythrocytes.

There was a progressive increase in $^3$H-peptides bound per thrombo-erythrocyte as a function of time, with the reaction slowing down or stopping at the 90-120 min time point. Maximum specific incorporation using 1.3 μmol of peptide and 1.1 μmol of crosslinker per 3.3×10$^9$ erythrocytes was 0.5-1.4×10$^6$ peptide molecules per thrombo-erythrocyte, representing ~0.3-0.7% of the added peptide. Nonspecific association of peptide with control erythrocytes was <3% of the specific incorporation as judged by control samples in which the crosslinker was omitted. In the 3 experiments in which the reaction was conducted in a single step, the results were comparable to those achieved using the 2-step reaction. In studies where radiolabeled thrombo-erythrocytes were solubilized in SDS and subjected to polyacrylamide gel electrophoresis, there were 3 identifiable radioactive bands (FIG. 3). The strongest was at Mr 87 kD, corresponding to the major periodic acid-Schiff (PAS)-staining band (PAS-1) (Thompson and Maddy, 1982, in *Red Cell Membranes—A Methodological Approach*, Ellory and Young, eds. Academic Press, N.Y., pp. 67-93). The second was at Mr 42 kD and corresponded to the second PAS-positive band (PAS-2), and the third was a weak band at Mr 22 kD corresponding to the third PAS-positive band (PAS-3).

8.2.3. Platelet-Thrombo-Erythrocyte Interactions

In more than 20 separate experiments, thrombo-erythrocytes prepared by incubating the peptide-crosslinker with erythrocytes for 120 min gave a positive response in the platelet-thrombo-erythrocyte co-aggregation assay using ADP; epinephrine and thrombin were tested in a smaller number of experiments and also found to be effective in stimulating platelet-thrombo-erythrocyte interactions, visible as macroscopic, red co-aggregates (FIG. 4). Microscopic examination of stained smears confirmed the intimate association between platelets and thrombo-erythrocytes (FIG. 5), with the platelet aggregates acting as bridges between thrombo-erythrocytes. In contrast, the thrombo-erythrocytes did not interact with platelets when no agonist was added, demonstrating the selectivity of the thrombo-erythrocytes for activated platelets. Control erythrocytes, which had been reacted with the peptide but not the crosslinker, did not interact with either unactivated or activated platelets (FIG. 4). When the platelets in these samples were activated, pure platelet aggregates could be identified microscopically (FIG. 5); macroscopically these appeared as small white clumps (FIG. 4). In time course experiments, crosslinking incubation times as short as 15 min were found sufficient to produce thrombo-erythrocytes that gave positive reactions in this assay, although the reactions tended to be less strong.

To exclude any confounding effects of the citrate anticoagulant used in these studies, the assay was also performed with PRP anticoagulated with heparin (4 U/ml) or hirudin (10 U/ml; Sigma) and similar results were obtained, although as expected, thrombin-induced activation did not occur with these anticoagulants. It is important to note that since these assays contain normal plasma, fibrinogen is available for binding to activated GPIIb/IIIa receptors; thus, the thrombo-erythrocytes were able to compete effectively with fibrinogen for the GPIIb/IIIa receptors.

Several inhibitors were used to assess whether the thrombo-erythrocytes were actually binding to the RGD binding site on the activated platelets' GPIIb/IIIa receptors. In fact, the co-aggregation was inhibited by a fluid-phase RGD peptide, a monoclonal antibody to GPIIb/IIIa and the $a_v\beta_3$ vitronectin receptor that blocks both the binding of fibrinogen to platelets and the interactions between RGD-coated beads and platelets (Coller, 1985, *J. Clin. Invest.* 76: 101-108; Coller et al., 1991, *Blood* 77:75-83), and EDTA, a strong divalent cation chelator that inhibits the interactions of all ligands with integrin receptors (FIG. 4).

To obtain more quantitative data, an assay was developed using gel-filtered platelets and thrombo-erythrocytes in an aggregometer. FIG. 6 depicts the results of an experiment demonstrating that thrombo-erythrocytes, but not control erythrocytes, interact with ADP-activated platelets. The thrombo-erythrocytes did not interact with unactivated platelets despite the stirring and 37° C. temperature. 10E5, a monoclonal antibody to GPIIb/IIIa that blocks the binding of fibrinogen to platelets and partially blocks the interaction of platelets with RGD-coated beads (Coller et al., 1983, *J. Clin. Invest.* 72:325-338) inhibited the interaction between platelets and thrombo-erythrocytes. In this assay, plasma proteins were removed in the gel-filtration step and thus there was little or no exogenous fibrinogen to compete with the thrombo-erythrocytes for binding to the activated platelets.

8.2.4. Binding of Thrombo-Erythrocytes to Platelets Adherent to Collagen

Hemostasis in vivo is thought to be initiated by adhesion of platelets to subendothelial proteins, in particular collagen, when blood vessels are damaged (Coller et al., 1989, *Blood*, 74:182-192). Platelets then aggregate on top of the adherent platelets, presumably as a result of the GPIIb/IIIa receptors on the lumenal surface of the adherent platelets undergoing the transformation that allows them to bind adhesive glycoproteins such as fibrinogen and von Willebrand factor with high affinity (Plow and Ginsberg, 1989, *Prog. Hem. Thromb.* 10:117-156). We therefore tested the ability of thrombo-erythrocytes to bind to platelets that had adhered to collagen. As in our previous studies (Coller et al., supra), a dense lawn of platelets adhered to the collagen in the presence of 2 mM $MgCl_2$. When control erythrocytes were then added, virtually none of the erythrocytes bound to the platelets (FIG. 7). In sharp contrast, the thrombo-erythrocytes formed a dense lawn on top of the platelet lawn and this reaction could be virtually completely inhibited by antibody 10E5 or the peptide RGDF (FIG. 7).

8.3. Discussion

In an attempt to succeed where previous approaches have failed, we have covalently attached the peptide Ac-CGGRGDF-$NH_2$ to erythrocytes via surface amino groups with the aid of a heterobifunctional cross-linking reagent. Approximately $0.5.-1.5 \times 10^6$ peptide molecules were cross-linked per erythrocyte after 120 min. The peptide appeared to be selectively crosslinked to glycoproteins that are present in the PAS-1, PAS-2, and PAS-3 regions, making it most likely that it is cross-linked to glycophorin A (whose dimeric form is largely responsible for PAS-1 and whose monomeric form is largely responsible for PAS-2), and the related glycoprotein, glycophorin B (which is largely responsible for PAS-3) (Anstee, 1990, Vox Sang. 58:1-20). It is interesting that there are an estimated $0.2-10 \times 10^6$ glycophorin A molecules per erythrocyte and $\sim 0.25 \times 10^6$ glycophorin B molecules per erythrocyte (Anstee, 1990, *Vox Sang.* 58:1-20.), raising the possibility that there is 1:1 stoichiometry between the number of crosslinked peptide molecules and the number of glycophorin A+-glycophorin B molecules.

Thrombo-erythrocytes were analyzed in several ways. The crosslinking reaction itself produced only slightly more hemolysis than simply washing the erythrocytes. In addition, there were only minimal changes in osmotic fragility. Laser diffraction ektacytometry, a technique that is sensitive to changes in the erythrocyte membrane and the hydration state of the cytoplasm of the erythrocyte, has been a useful tool in analyzing erythrocytes altered in vitro and erythrocytes from patients with a variety of disorders (Mohandas et al., 1980, *J. Clin. Invest.* 66:563-573; Clarck et al., 1983, *Blood* 61:899-910; Pasvol et al., 1989, *Blood* 74:1836-1843). Abnormal values are obtained in many disorders associated with shortened in vivo erythrocyte survival (Clarck et al., 1983, *Blood* 61:899-910). It is notable, therefore that thrombo-erythrocytes were indistinguishable from untreated erythrocytes in this assay.

Thrombo-erythrocytes are able to selectively interact with platelets activated with ADP, epinephrine, or thrombin to produce large aggregates containing mixtures of platelets and erythrocytes. Studies wich monoclonal antibodies to GPIIb/IIIa and fluid phase RGD peptides indicate that the RGD peptides on the erythrocytes bind to the activated GPIIb/IIIa receptors on the platelets. The interactions occur even in the presence of normal amounts of plasma fibrinogen, indicating that the thrombo-erythrocytes can compete effectively with fibrinogen for binding to activated GPIIb/IIIa receptors. In addition, the interactions are not limited to platelets in citrated PRP since platelets in PRP prepared from blood anticoagulated with either heparin or hirudin are also able to interact with the thrombo-erythrocytes.

To simulate better the likely in vivo situation at a site of vascular injury, where platelets first adhere to adhesive proteins in the blood vessel wall, we also tested the ability of the thrombo-erythrocytes to bind to platelets that had adhered to collagen. The thrombo-erythrocytes, but not control erythrocytes, bound readily to the adherent platelets, and studies with a monoclonal antibody to GPIIb/IIIa and RGD peptides again supported a mechanism involving the interaction of the RGD peptides with the activated GPIIb/IIIa receptors.

These in vitro studies are positive indicators of the utility of the thrombo-erythrocyte as a potential alternative to fresh platelets. Since there are 20 times as many erythrocytes as platelets in the circulation of normal individuals, conversion of the erythrocytes contained in 50 ml of blood into thrombo-erythrocytes would produce as many thrombo-erythrocytes as there are platelets in 1 liter of blood, or approximately 2 conventional units of platelets. Moreover, since erythrocytes are 9 times as large as platelets, the 50 ml of blood would yield the equivalent of 18 conventional units of platelets by mass. The technique of erythrocyte washing is already standard practice in blood banks and the cross-linking reaction can be carried out within 1-2 hours, depending upon the density of peptides selected. Thus, thrombo-erythrocytes can function as an autologous, semi-artificial platelet alternative.

In addition to their functions in platelet adhesion and aggregation, platelets make other contributions to enhancing hemostasis and so it is appropriate to question whether thrombo-erythrocytes might also serve to enhance the hemostatic response. One of the functions platelets serve is to act as a surface on which coagulation reactions take place (Walsh and Schmaier, 1987, In *Homeostasis and Thrombosis: Basic Principles and Clinical Practice*, Colman et al., eds., Lippincott, Philadelphia, pp. 689-703). Both unique platelet receptors and the platelets' non-specific phospholipid membrane have been implicated in this function and it is unclear how much each contributes (Walsh and Schmaier, 1987, In *Homeostasis and Thrombosis: Basic Principles and Clinical Practice*, Colman et al., eds., Lippincott, Philadelphia, pp. 689-703). The erythrocyte membrane can also serve to accelerate coagulation reactions under certain circumstances and so it is possible that thrombo-erythrocytes may also be able to facilitate thrombin formation (Zwaal et al., 1989, *Molec. Cell Biochem.* 91:23-31). The recent discovery that erythrocytes can enhance platelet activation via cooperative biochemical interactions with platelets involving eicosanoid metabolism (Santos et al., 1991, *J. Clin. Invest.* 87:571-591) provides another potential mechanism by which thrombo-erythrocytes may enhance the function of residual platelets. Platelets release ADP from their dense granules when stimulated, leading to ADP-induced platelet activation; erythrocytes are rich in ADP and so it is possible that ADP may leak from thrombo-erythrocytes that become enmeshed in hemostatic plugs. Finally, the identification of nitric oxide produced by cells in the blood vessel wall as a potent inhibitor of platelet activation suggests another potential mechanism by which thrombo-erythrocytes may enhance platelet function since free hemoglobin and hemoglobin in erythrocytes have been demonstrated to neutralize the effect of nitric oxide (Houston et al., 1990, *Blood* 76:953-958).

9. A Bead Model for RGD Binding to Platelets

In the series of studies described herein on peptides of the general structure $(G)_n$-RGDF (where n equals the number of glycine residues) that were covalently attached to polyacrylonitrile beads via their amino termini, it was discovered that the length of the peptide profoundly affected the ability of the beads to interact with platelets. Thus, with beads coated with peptides with n=1, very little interaction occurred between the beads and either unactivated or activated platelets, whereas when n=9, strong interactions occurred with both unactivated and activated platelets. When the peptide had n=3, the interactions were highly dependent on the state of platelet activation, with platelets treated with $PGE_1$ reacting poorly if at all, and platelets treated with ADP reacting briskly.

Specifically, to gain additional information on the RGD binding domains of the platelet integrins (see Table III), a series of RGD peptides containing variable numbers of glycine residues as spacers [$(G)_n$-RGDF] were immobilized on polyacrylonitrile beads via their amino-terminal glycine residues and the ability of these beads to interact with platelets was then evaluated. The differential platelet agglutinating effects of these beads as a function of the number of glycine residues permitted the exploration of the RGD binding site(s) under basal conditions and in the presence of platelet agonists and inhibitors. In addition, we were able to analyze a series of monoclonal antibodies directed at the different integrin receptors for their ability to inhibit the interactions.

TABLE III

PLATELET INTEGRIN RECEPTORS

| Common Name | Platelet Protein Composition | Chain Composition α | β | Ligands | Number of Surface Receptors Per Platelet | Mean Distance Between Receptors (Angstroms)+ |
|---|---|---|---|---|---|---|
| Collagen Receptor | Ia/IIa (VLA-2) | $\alpha_2$ | $\beta_1$ | Collagen | ~1,000 | 1,490 |
| Fibronectin Receptor | Ic*/IIa (VLA-5) | $\alpha_5$ | $\beta_1$ | Fibronectin | ~1,000 | 1,490 |
| Laminin Receptor | Ic/IIa (VLA-6) | $\alpha_6$ | $\beta_1$ | Laminin | ~1,000 | 1,490 |
| Vitronectin Receptor | $\alpha_v$/IIIa | $\alpha_v$ | $\beta_3$ | Vitronectin, Fibrinogen, von Willebrand factor, Thrombo-spondin | ~100 | 4,700 |
| Fibrinogen Receptor | GPIIb/IIIa | $\alpha_{IIb}$ | $\beta_3$ | Fibrinogen, Fibronectin, von Willebrand Factor, Vitronectin, Thrombo-spondin | 50,000 | 214 |

+Assumes a platelet surface area of $22.2\mu^2$ and equal spacing between receptors

9.1. MATERIALS AND METHODS

9.1.1. Platelet Preparation

Blood was drawn by syringe and placed in polypropylene test tubes containing 0.01 volume 40% trisodium citrate. Platelet-rich plasma (PRP) was prepared by centrifugation at ~700×g for 3.5 min at 22° C. and adjusted to $3 \times 10^{11}/l$ with platelet-poor plasma (PPP, prepared by centrifuging for 10 min at 1600×g at 22° C.). Gel-filtered platelets (GFP) were prepared as previously described (Coller et al., 1989, *Blood* 74:182) by layering the PRP onto a column of Sepharose 2B and eluting with a modified Tyrode's solution containing no added $CaCl_2$ and 2 mmol/l $MgCl_2$ (138 mmol/l NaCl, 2.7 mmol/l KCl, 0.4 mmol/l $NaH_2PO_4$, 12 mmol/l $NaHCO_3$, 2 mmol/l $MgCl_2$, 0.2% bovine serum albumin (BSA), 0.1% glucose, 10 mmol/l HEPES, pH 7.4 ).

9.1.2. Peptides

The peptides $(G)_n$-RGDF were synthesized on two different occasions on a solid phase synthesizer (Applied Biosystems, Foster City, Calif., Model 430A) using t-Boc chemistry; a 4-methylbenzhydrylamine (4-MBHA) resin was used so that the peptides contained carboxy-terminal amides rather than free carboxyl groups after cleavage. Benzyl-ester and tosyl side chain protection groups were used, respectively, for aspartic acid and arginine. In the first synthesis, the peptide $G_1$ RGDF was prepared and 20% of the resin was removed and subjected to cleavage with HF. Two glycines were then added to the peptide on the resin and another 20% was removed for HF cleavage. The process was continued until the entire series of peptides ($G_1$, $G_3$, $G_5$, $G_7$ and $G_9$RGDF) were synthesized. The second synthesis followed the same general scheme. but consisted of four different syntheses: $G_1$ and $G_3$ RGDF; $G_5$ and $G_7$ RGDF; $G_9$, $G_{11}$ and $G_{13}$ RGDF; and $G_{15}$, $G_{17}$ and $G_{19}$ RGDF. Double couplings were used for arginine, phenylalanine, the fifth and all subsequent glycine residues in the first synthesis, and the fourth and all subsequent glycine residues in the second synthesis. The peptides were cleaved from the resin with HF in the presence of anisol and dimethylsulfide (10:1:1 by volume); the starting temperature was −10° C. and the temperature was maintained below −2° C. throughout the cleavage by adding ice to the ice-salt mixture. The peptides were washed with ethyl ether and then extracted twice with 30% HAc and twice with 10% HAc. The pooled extracts were then diluted to a final concentration of ~10% HAc and lyophilized. Peptide homogeneity was assessed by HPLC using a C8 reverse phase column (Aquapore RP-300, Applied Biosystems, 300 Å pore size, 7 μ spherical silica, 4.6×220 mm) with an acetonitrile gradient of 0.60% in 0.1% trifluoroacetic acid that was programmed to run over 40 min. Average purity was 72±5% (mean±SEM) in the first synthesis and 80±3% in the second. Since $G_{19}$ RGDF exhibited the poorest homogeneity as judged by HPLC (56%), it was purified to >95% homogeneity with preparative HPLC on a larger column of the same material (10×250 mm). The functional activities of the crude and purified $G_{19}$ RGDF peptides in the bead agglutination assay were the same. A fibrinogen γ-chain dodecapeptide (amino acids 400–411) containing an added amino-terminal tyrosine (Y-HHLGGAKQAGDV) was a gift from Dr. Ellinor Peerschke, State University of New York at Stony Brook, N.Y. The snake venom peptide trigramin, which contains an RGD sequence and inhibits fibrinogen binding to GPIIb/IIIa, (Huang et al., 1987, *J. Biol. Chem.* 262:16157) was a gift of Dr. Stephan Niewiarowski, Temple University, Philadelphia, Pa.

Fast atom bombardment mass spectrometry was performed on peptides prepared in the second synthesis by collecting the HPLC elution peaks, drying the samples under vacuum (Speed Vac Concentrator, Savant Instruments Inc., Farmingdale, N.Y.), and redissolving them either in methanol ($G_{1-7}$ RGDF) or 25% HCl ($G_{9-19}$ RGDF). For the $G_{1-11}$ RGDF peptides, the mass spectrometry probe was precoated with 1 μl of 50% glycerine/50% thioglycerine matrix and then 1 μl of the peptide solution was added; for the $G_{13-19}$ RGDF peptides, the probe was precoated with 1 μl of thioglycerine matrix and then 1 μl of the peptide solution was added. The fast atom bombardment mass spectra were generated on a Kratos MS890/DS90 mass spectrometry system (Ramsey, N.J.). A saddle field ion source (Ion Tech, Middlesex, England) was used as a source of fast xenon atoms; it produced 1 mA of ion current when operated at 7 kV. The mass spectrometer was operated at 6.8 kV and the mass range was calibrated with cesium iodide in the positive ion mode using a 10 sec/decade scan speed after adjusting for the 1 amu added to the molecule by protonation. The observed molecular weights of all peptides prepared in the second synthesis ($G_{1-19}$ RGDF) matched precisely the predicted molecular weights. To verify the identity of the peptides prepared in the first synthesis, 1:1 mixtures of the corresponding peptides in the first and second syntheses were analyzed by HPLC and all of them showed only a single peak.

For studies to assess the effect of RGD-containing peptides on the binding of radiolabeled monoclonal antibodies to platelets, the peptide RGDS was obtained from Peninsula Laboratories (Belmont, Calif.) or synthesized as described above. A longer peptide that is a composite of the γ-chain decapeptide (402–411) and one of the polyarginine RGDV peptides described by Ruggeri et al. (Ruggeri et al., 1986, *Proc Natl. Acad. Sci. U.S.A.* 83:5708) (LGGAKQAGDV(R)8RGDV) was also tested. This peptide was synthesized as above; HPLC demonstrated a single major peak containing more than 67% of the absorbance.

The BIOGRAPH molecular modeling computer program (Bio Design, Inc., Pasadena, Calif.; version 1.34) was used to determine the peptide lengths. Calculations were made for the peptides in both the extended form and in the alpha-helical conformation so as to span these two extreme possibilities. We do not know the exact conformation of the peptides in solution, but we suspect that the glycines attached to the RGDF assume a multitude of random conformations because of the rotational freedom of glycine residues. It is possible, however, that immobilization of the peptides on the beads at high density limits this conformational freedom.

9.1.3. Fibrinogen Bead Assay and Functional Assessment of $G_n$-RGDF Peptides The fibrinogen bead agglutination assay was performed as previously described (Coller, 1980, *Blood* 55:169) Briefly, fibrinogen (lot number PR2548, Cutter Laboratories, Berkeley, Calif.) purified according to the method of Mosesson (Mosesson, 1962, *Biochim. Biophys. Acta* 57:204) was coupled to 1.3 μ polyacrylonitrile beads containing N-hydroxysuccinimide groups at a ratio of 3 mg fibrinogen per 1 ml bead slurry (containing 67 mg beads) (Matrex 102; Amicon, Danvers, Mass.). After coupling was completed, the beads were washed extensively with 0.15M NaCl, 10 mM Tris/HCl, pH 7.4, containing 0.05% sodium azide (TSA), resuspended in TSA and kept at 4° C. To perform the assay, thirty-five μl of citrated PRP ($3 \times 10^{11}/l$) was incubated with 35 μl of peptide in TSA in a round bottom 96-well microtiter plate for at least 10 min at 22° C. Then 5 μl of beads containing ~0.4 μg of bound fibrinogen ($5 \times 10^5$ molecules per bead) was added and the plate was rotated at 260 rpm. The degree of agglutination was graded visually on a scale between 0 and 100% as a function of time. Antibody 10E5, which binds to GPIIb/IIIa and blocks fibrinogen binding (Coller et al., 1983, *Blood* 61:99), produces complete inhibition of bead agglutination in this assay when used at 10–20 μg/ml, and so a sample containing 10E5 instead of peptide was included in each assay as a positive control. A negative control consisting of TSA buffer instead of peptide was also included in each assay; this control consistently reached maximal agglutination (100%) after 4 minutes and so the inhibitory effects of the peptides $G_{1-9}$-RGDF in solution were also assessed after 4 minutes. The longer peptides, $Gu_{11-19}$ RGDF, were poorly soluble under these conditions and so could not be tested in this manner (see below).

9.1.4. Covalent Coupling of Peptides to Beads

One ml of the polyacrylonitrile beads (67 mg) (Matrex 102, Lot nos. JC 1236 and 1239) in dry dioxane was centrifuged at 10,000×g for 1 min at 22° C. The supernatant dioxane was removed, and the beads were rapidly washed twice with 0.05M Na acetate, pH 5.5. The pelleted beads were then resuspended in 1 ml of a 4.05 mM solution of peptides $G_1$, $G_3$, $G_5$, $G_7$ or $G_9$ RGDF in 0.05M Na acetate buffer, pH 6.5, and allowed to rock overnight at 4° C. Any remaining reactive N-hydroxysuccinimide groups were blocked by adding 0.1 volume of 1 H glycine ethyl ester, pH 8 for 30 min at 22° C. The beads were then washed extensively in TSA, pH 7.4, resuspended in a volume of 1.5 ml of TSA and stored at 4° C. The $G_{11}$, $G_{13}$, $G_{15}$, $G_{17}$ and $G_{19}$-RGDF peptides were only partially soluble in the acetate buffer, but they were fully soluble in 0.1% trifluoroacetic acid (TFA), pH 2.5, at 22° C. or 37° C. The $G_{11}$, $G_{13}$, $G_{15}$, $G_{17}$ and $G_{19}$-RGDF peptides therefore, were coupled to the beads in 0.1% TFA, pH 2.5 for 72 hrs. For comparison purposes, the $G_1$, $G_3$, $G_5$, $G_7$ and $G_9$ RGDF peptides were also coupled to beads under these circumstances and these beads were similar in coupling efficiency and platelet agglutinating activity to those coupled in the acetate buffer (see below). Bovine serum albumin (BSA, essentially globulin free, Sigma) at 30 $\mu M$ was coupled to 1 ml of the beads as a control. In another series of experiments to assess the impact of decreasing the density of peptides on the beads, the $G_3$ RGDF and $G_9$RGDF peptides were diluted to concentrations between 0.4 $\mu M$ and 4.05 mM before coupling.

Coupling efficiency was assessed by HPLC by comparison of the areas under the peptide peaks in the pre- and post-coupling samples; the results are shown in Table IV for the standard method using 4.05 mM peptide. The $G_1$, $G_3$, $G_5$, $G_7$ and $G9$ RGDF peptides at pH 6.5 and the $G_{11}$, $G_{13}$, $G_{15}$, $G_{17}$ and $G_{19}$ RGDF peptides at pH 2.5 were coupled at ~74% and ~91% efficiency, respectively.

TABLE IV

EFFICIENCY OF PEPTIDE COUPLINGS TO POLYACRYLONITRILE BEADS

| Peptides | Concentration (mM) | Buffer | Coupling Efficiency (%) |
|---|---|---|---|
| $G_{1-9}$-RGDF | 4.05 | Acetate, pH 6.5 | 73 ± 1* (n + 5) and 75 ± 4 (n = 5) |
| $G_{11-19}$-RGDF | 4.05 | TFA+ | 91 ± 5 (n = 5) |
| $G_3$-RGDF | 2 | Acetate, pH 6.5 | 94 |
| $G_3$-RGDF | 1 | Acerate, pH 6.5 | 97 |
| $G_3$-RGDF | 0.5 | Acetate, pH 6.5 | 98 |
| $G_3$-RGDF | 0.0004–0.5 | Acetate, pH 6.5 | >98 |
| $G_9$-RGDF | 2 | Acetate, pH 6.5 | 88 |
| $G_9$-RGDF | 1 | Acetate, pH 6.5 | 92 |
| $G_9$-RGDF | 0.0004–0.5 | Acetate, pH 6.5 | 98 |
| $G_9$-RGDF | <0.5 | Acetate, pH 6.5 | >98 |
| Albumin | 0.03 | Acetate, pH 6.5 | 98 |

*Mean ± SEM
+Trifluoroacetic acid

Assuming an average coupling efficiency of 80% for these peptides then $\sim 19 \times 10^{18}$ peptide molecules were bound to each 67 mg of beads ((4.05 $\mu$moles/ml) ($6.02 \times 10^{17}$ molecules/$\mu$mole) (0.8)); this number of molecules represents ~40% of the N-hydroxysuccinimide groups on the beads, indicating the high efficiency of coupling. Since the estimated surface area of the beads is 6 m2/gram, the peptides are ~4.6 Å apart on the beads ((6 m2/gram)×(0.067 gram)=0.4 m2; $\sqrt{0.4}$ m2=0.63 m or 6.3 $\times 10^9$ Å; $\sqrt{1.9 \times 10^{18}}$ molecules=$1.38 \times 10^9$ molecules; ($6.3 \times 10^9$ Å)/($1.38 \times 10^9$ molecules)=4.6 Å per molecule) (Table V). The extraordinarily high peptide density this represents is best appreciated by translating the results into an equivalent molar concentration assuming that the molecules are 4.6 Å apart in fluid phase; the result is a 17M solution. For comparison, the mean distances between fluid phase peptides at various concentrations are also given, as are comparable values for fibrinogen molecules on beads, fibrinogen molecules in plasma, albumin molecules on beads and albumin molecules in plasma.

TABLE V

LIGAND DENSITIES AND CONCENTRATIONS

| Ligand | Amount Added to 67 mg Beads ($\mu$moles) | Coupling Efficiency (%) | Mean Distance Between Molecules (Å) | Molar Concentration Equivalent |
|---|---|---|---|---|
| Immobilized $G_{1-19}$-RGDF Peptides | 4.05 | ~80 | 4.6 | $1.7 \times 10^1$ |
| | $4.05 \times 10^{-1}$ | 98 | 13 | $7.5 \times 10^{-1}$ |
| | $4.05 \times 10^{-2}$ | 98 | 41 | $2.4 \times 10^{-2}$ |
| | $4.05 \times 10^{-3}$ | 98 | 130 | $7.6 \times 10^{-4}$ |
| | $4.05 \times 10^{-4}$ | 98 | 410 | $2.4 \times 10^{-5}$ |
| Soluble $G_{1-19}$-RGDF Peptides | | | 550 | $1 \times 10^{-5}$ |
| | | | 260 | $1 \times 10^{-4}$ |
| | | | 120 | $1 \times 10^{-3}$ |
| | | | 94 | $2 \times 10^{-3}$ |
| | | | 75 | $4 \times 10^{-3}$ |
| Immobilized Fibrinogen | $5.9 \times 10^{-3}$ | ~88 | 113 | $1.2 \times 10^{-3}$ |
| Fibrinogen in Plasma | | | 570 | $8.8 \times 10^{-6}$ |
| Immobilized Albumin | $3.0 \times 10^{-2}$ | 98 | 47 | $1.6 \times 10^{-2}$ |
| Albumin In Plasma | | | 140 | $6 \times 10^{-4}$ |

9.1.5. Monoclonal Antibodies

Table VI lists the antibodies, their specificities and the concentrations used. They have all been characterized previously: antibodies 10E5 (Coller et al., 1983, *J. Clin. Invest.* 72:325), 7E3 (Coller B. S., 1985, *J. Clin. Invest.* 76:101), 6D1 (Coller et al., 1983, *Blood* 61:99), and 6F1 (Coller et al., 1989, *Blood* 74:182) are from the laboratory; antibody $A_2A_9$ (Bennet et al., 1983, *Proc. Natl. Acad. Sci. U.S.A.* 80:2417) was a gift of Dr. Joel Bennett, University of Pennsylvania; antibody PAC-1 (Shattil et al., 1985, *J. Biol. Chem.* 260:1107) was a gift of Dr. Sanford Shattil, University of Pensylvania; antibody LM 609 (Cheresh et al., 1987, *J. Biol. Chem.* 262:17703) was a gift of Dr. David Cheresh, Scripps Research Institute; antibody $GoH_3$ (Sonnenberg et al., 1988, *Nature* 336:487) was a gift of Dr. A. Sonnenburg of the Netherlands Red Cross; and antibody mAb16 (Akiyama et al., 1989, *J. Cell. Biol.* 109:863) was a gift of Dr. Kenneth Yamada, National Institutes of Health, Bethesda, Md. The platelets were incubated with the antibody concentrations indicated for 30–60 min before the addition of the beads. In the case of PAC-1, which binds only to activated platelets (Shattil et al. 1985, *J. Biol. Chem.* 260:1107), the platelets were activated with ADP (6.7 $\mu M$ final concentration) without stirring for 5 min before adding the antibody.

TABLE VI

MONOCLONAL ANTIBODIES AND PEPTIDES TESTED IN $G_9$-RGDF BEAD ASSAY

| | | | Inhibition of $G_9$-RGDF Bead Agglutination (%) | |
|---|---|---|---|---|
| Designation | Specificity | Concentration | −ADP | +ADP |
| Antibodies | | | | |
| 10E5 | GPIIb/IIIa | 20 $\mu$g/ml | 40 | 21 |
| 7E3 | GPIIb/IIIa + a/IIIa | 20 $\mu$g/ml | 100 | 100 |
| $A_2A_9$ | GPIIb/IIIa | 20 $\mu$g/ml | 62 | 45 |
| PAC-1 | GPIIb/IIIa | 60 $\mu$g/ml | — | 8 |
| LM609 | $a_v$/IIIa | 100 $\mu$g/ml | 0 | 0 |
| GoH3 | GPIc/IIa | 100 $\mu$g/ml | 0 | 0 |
| mAb16 | GPIc*/IIa | 20 $\mu$g/ml | 0 | 0 |
| 6F1 | GPIa/IIa | 20 $\mu$g/ml | 0 | 0 |
| 6D1 | GPIb | 20 $\mu$g/ml | 0 | 0 |

TABLE VI-continued

MONOCLONAL ANTIBODIES AND PEPTIDES TESTED IN G9-RGDF BEAD ASSAY

| Designation | Specificity | Concentration | Inhibition of G9-RGDF Bead Agglutination (%) | |
|---|---|---|---|---|
| | | | −ADP | +ADP |
| Peptides | | | | |
| RGDF | | $\leq 4.2 \times 10^{-4}$M | 0 | |
| | | $1-4 \times 10^{-3}$M | 50-100 | |
| Fibrinogen | | $\leq 4.5 \times 10^{-4}$M | 0 | |
| Dodecapeptide (+Tyr) | | $1.8 \times 10^{-3}$M | 13 | |
| (Y-HHLGAKQAGDV) | | $3.6 \times 10^{-3}$M | 67 | |
| Trigramin | | 4.5 μg/ml | 0 | |

9.1.6. Agglutination Assay with Peptide-Coated Beads

To 70 μl of PRP or GFP at a count of $3 \times 10^{11}$ platelets/l in a 96 well round bottom polystyrene microtiter plate, 5 μl of a well mixed bead suspension (0.22 mg beads) was added and the plate was rotated at 260 rpm (Orbit shaker, Lab Line Instruments, Melrose Park, Ill.) for various times between 0 and 30 min (0.5, 1, 2, 4, 6, 8, 10, 12, 15, 20, 25, 30 min). At the indicated times the wells were observed from the bottom with the aid of a magnifying mirror apparatus (Cooke Microtiter System, Dynatech Laboratories, Inc. Alexandria, Va.) and the degree of the bead-agglutination was rated visually from 0% (no visible agglutination, indistinguishable from the control, albumin-coated beads) to 100% (full agglutination) (FIG. 8A). Platelet counts in the supernatant plasma or buffer were measured by removing 5 μl from the supernatant after allowing the bead agglutinates to settle for 3 min. The platelet counts decreased during the agglutination, indicating that increasing numbers of platelets were incorporated into the agglutinates (FIG. 8B). In some experiments, platelets were activated with 6.7 μM ADP 30 sec prior to the addition of the beads; in other experiments the platelets were preincubated with 0.14 μM PGE$_1$ (Sigma, St. Louis) for 30 min. Control experiments indicated that there was no agglutination at all in the presence of EDTA (10 mM). There was only a minimal increase in the supernatant lactate dehydrogenase level during the agglutination, indicating that the platelet-bead interaction did not produce significant platelet lysis.

9.1.7. Release of $^{14}$C-Serotonin from Platelets

Citrated PRP ($3 \times 10^{11}$/l) was incubated with $^{14}$C-5-serotonin (10 μCi/ml stock solution, 20-25 nCi/ml final concentration, New England Nuclear, Boston, Mass.) for 30 min at 22° C. with gentle stirring (~100 rpm) using a teflon coated stir bar. In order to maintain the PRP pH constant at ~7.60, the PRP was overlayed with 5% CO$_2$, 95% air just before the incubation began. Serotonin uptake was terminated by adding 5 μM imipramine (Sigma) and stirring was continued for another 5 min. Total uptake under these conditions was 70-80% of the added serotonin. The agglutination assay was performed in quadruplicate in the same way as described above except that after 8 min of shaking, 70 μl of cold 2% paraformaldehyde in PBS, pH 7.4 was added to the wells and the microtiter plate was centrifuged at $1000 \times g$ for 5 min at 22° C. The top 50 μl of the supernatant (total volume in each well was 145 μl) was added to scintillation fluid and counted in a scintillation spectrometer. In some experiments the PRP was preincubated with acetylsalicylic acid (50 μM) or PGE$_1$ (0.14 μM) during the serotonin uptake.

9.1.8. Effect of RGD Peptides on 7E3 and 10E5 Binding

To assess the effect of RGD-containing peptides on the initial rate of binding of 7E3 and 10E5, studies were conducted with $^{125}$I-7E3 and $^{125}$I-10E5 essentially as described before (Coller, B.S., 1985, J. Clin. Invest. 76:101). The RGDS or LGGAKQAGDV(R)$_8$RGDV peptide was incubated at 22° C. with citrated PRP (~$3 \times 10^8$/ml) for 1 to 5 min at various concentrations and then non-saturating concentrations of the antibodies (1.5-2.5 μg/ml) were added for 1 to 2 min. The bound antibody was separated from the free by centrifugation of the PRP through 20% sucrose and both the platelet pellet and the supernatant were counted. Results were expressed as either an increase or decrease in antibody binding as compared to a buffer control.

9.2. RESULTS

9.2.1. Effects of Soluble G$_{1-9}$-RGDF Peptides on the Fibrinogen Bead Assay The ability of the soluble G$_{1-9}$-RGDF peptides to inhibit platelet-fibrinogen interactions was tested with the fibrinogen bead assay (Table VII).

TABLE VII

MINIMAL INHIBITORY CONCENTRATIONS OF FREE (G)$_n$-RGDF PEPTIDES IN SOLUTION IN THE FIBRINOGEN-BEAD ASSAY

| Peptide | Minimal Concentration Required to Prevent Complete Agglutination (μM) |
|---|---|
| RGDF | 16, 32* |
| G$_1$-RGDF | 32, 56 |
| G$_3$-RGDF | 32, 56 |
| G$_5$-RGDF | 63, 113 |
| G$_7$-RGDF | 113, 127 |
| G$_9$-RGDF | 227, 253 |

*Values are from 2 different experiments using platelet-rich plasma.

There was a distinct decrease in potency with increasing numbers of glycine residues, with the RGDF peptide approximately ten-fold more potent than the G$_9$-RGDF peptide. The decreased potency of the longer peptides is unlikely to be accounted for solely on the basis of decreased diffusion coefficients since the molecular weight of the G$_9$-RGDF peptide (786) is less than twice that of the RGDF peptide (435).

9.2.2. Peptide Bead Agglutination Assay

Albumin coated beads were not agglutinated by the platelets, even when ADP was added. This indicates that the beads are not non-specifically incorporated into the platelet aggregates that form when ADP is added.

The data in FIGS. 8A-B and 9A-B show the extent of agglutination of (G)$_n$-RGDF beads by PRP as a function of time and the number of glycine residues. Both the total platelet agglutinating activity and the speed of agglutination increased dramatically as the number of glycine residues increased from 1 to 13 and then the activity decreased as the number of glycines increased further to 19. The G$_7$-RGDF beads gave values in between those produced by the G$_5$-RGDF and G$_9$-RGDF beads, and the G$_{11}$-RGDF and G$_{13}$-RGDF beads gave values that were similar to those of the G$_{13}$-RGDF beads. Thus, even though the shorter RGDF peptides were more potent than the G$_9$-RGDF peptide when tested in fluid phase in inhibiting the fibrinogen bead assay, the immobilized $G_9$-RGDF peptide was much more potent in agglutinating platelets than the immobilized smaller peptides. The decrease in platelet agglutinating activity of the longest peptides ($G_{17}$- and $G_{19}$ RGDF) was notable and perhaps suggests that the peptides have sufficient freedom to fold back on themselves or interact with each other.

The addition of ADP to the platelets prior to the $(G)_n$-RGDF beads increased both the speed and extent of agglutination with all of the different beads (FIG. 10A). The $G_3$-RGDF beads showed the greatest increase in total extent of agglutination with ADP stimulation, going from $44 \pm 6\%$ (n=17) to $96 \pm 4\%$ (n=7) at 30 min. Thus preactivation of the platelets with ADP appears to increase the affinity of the RGD-binding sites and/or reduce their distance from the platelet surface.

Preincubation of the PRP with $PGE_1$ significantly diminished the ability of the PRP to agglutinate the $(G)_n$-RGDF beads (FIG. 10B). The agglutination of the $G_1$-RGDF and $G_3$-RGDF beads was completely abolished, but agglutination with the longer beads was less affected; in fact, the $G_9$-RGDF beads underwent $75 \pm 16\%$ (n=7) agglutination at 30 min and the $G_{15}$-RGDF beads underwent $88 \pm 13\%$ (n=4) at the same time point. Thus, the inhibition of platelet activation by $PGE_1$ was not able to prevent significant interactions between platelets and the longer $(G)_n$-RGDF beads. The beads coated with the $G_3$-RGDF peptide showed the most marked differences in platelet interaction as a function of platelet activation; $PGE_1$ totally inhibited the interactions, whereas ADP dramatically increased both the speed and extent of agglutination (FIG. 10C). Thus, the $G_3$-RGDF peptide appears to have a critical length or flexibility for reporting on the state of activation of the RGD receptor site(s).

Decreasing the number of peptides on the bead surface decreased the agglutination reaction (FIGS. 11A-B), but full agglutination could eventually be achieved even when the peptide number was decreased nearly 10-fold. Some agglutination of PRP occurred even when the peptide number was reduced approximately 100-fold. With ADP preactivation, all of the bead preparations showed enhanced agglutination and full agglutination was even achieved with the beads containing approximately 100-fold fewer peptides. Based on the density calculations (Table V), these data indicate that a peptide-peptide distance on the beads $\leq 13$ Å is required for full agglutination of non-activated platelets, whereas a peptide-peptide distance 41 Å is adequate for full agglutination of ADP-activated platelets.

The inhibitory effects of free RGDF and $\gamma$-chain peptides on the bead agglutination were also investigated. High RGDF-concentrations were required to inhibit the agglutination of the beads containing the longer peptides (Table VI) and lower concentrations were required with the shorter peptide beads. For example, 41 µM RGDF abolished agglutination with $G_1$-RGDF beads, whereas 400 µM was required to abolish agglutination with $G_3$-RGDF beads, and 3-4 mM RGDF was needed to abolish agglutination with beads containing 7 or more glycine residues. Lower concentrations of RGD peptides produced incomplete inhibition that was most notable during the early phase of platelet agglutination. The fibrinogen $\gamma$-chain dodecapeptide derivative also inhibited agglutination of the $(G)_n$-RGDF beads; on a molar basis, the potency of the inhibition of the $\gamma$-chain peptide was slightly less than that of the RGDF peptide (Table VI).

9.2.3. The Release of Serotonin

The interaction of the platelets in PRP with the longer immobilized peptides resulted in the release of serotonin, and the extent of release correlated with the extent of agglutination (Table VIII).

TABLE VIII

Release of Serotonin From Platelets in Platelet-Rich Plasma Interacting With $(G)_n$-RGDF Beads For 8 Minutes

| Peptide on Bead | Serontonin Release (% of Maximal) | Agglutination (% of Maximal) |
| --- | --- | --- |
| $G_1$-RGDF | 1* | 0* |
| $G_3$-RGDF | 2 | 17 |
| $G_5$-RGDF | 9 | 75 |
| $G_7$-RGDF | 16 | 88 |
| $G_9$-RGDF | 19 | 100 |

*Mean values for 2 or 3 experiments

Preincubation of the platelets with acetylsalicylic acid (50 µM) did not change this pattern. $PGE_1$, however, abolished release for the 8 min of agglutination with all the beads, but the agglutination response with the longer beads still reached 50%. Thus it can be inferred that the release reaction is not a prerequisite for agglutination, but it may amplify and accelerate the response.

9.2.4. The Interaction of GFP with RGDF Beads

Gel-filtered platelets showed a pattern of interaction with the beads that was similar to that observed with PRP in that the agglutination was dependent on the peptide length and was enhanced by activating the platelets with ADP (FIG. 12). These data indicate that interaction of the beads with plasma proteins is not required for agglutination. There were, however, some minor differences in agglutination with GFP compared to PRP. Thus, with the beads containing the shorter peptides, the agglutination by 5 GFP was slower and less extensive than with PRP. In contrast, with the beads containing the longer peptides, the agglutination by GFP was somewhat brisker than that produced by PRP, although the ultimate extent of agglutination was maximal with both platelet preparations. The effects of gel-filtration on platelet functions, the presence of plasma proteins, and/or the differences in pH (PRP pH ~7.70 and GFP pH 7.40) probably account for these minor differences.

9.2.5. Effect of Monoclonal Antibodies on RGDF Bead Agglutination

Monoclonal antibodies 10E5, $A_2A_9$, 7E3, and PAC-1, which interact with GPIIb/IIIa and inhibit fibrinogen binding to platelets, all inhibited the interaction of platelets in PRP with $G_1$-RGDF, $G_3$-RGDF, and $G_5$-RGDF beads by >90%, even with ADP activation. With the longer beads, however, differences in the antibodies' inhibitory potency became apparent. As illustrated in FIG. 13A, with the $G_9$-RGDF beads 10E5 markedly delayed the initial agglutination response but by 30 min it reached ~60% of the control value. Since 10E5 blocks platelet aggregation, this demonstrates that platelet aggregation is not required for agglutination to occur. Increasing the 10E5 concentration 3-fold (to 60 µg/ml) did not change this pattern. $A_2A_9$ produced greater, but still incomplete, inhibition, with the agglutination reaching only 38% by 30 min. 7E3 produced the most extensive inhibition, with no agglutination detectable at 30 min. When the assay was performed with platelets that were stimulated with ADP, 10E5 and $A_2A_9$ were somewhat less inhibitory, especially at the earlier time points, but the differences were still dramatic compared to the control (FIG. 13B). 7E3 was still able to produce complete inhibition under these circumstances. With $G_{11}$-, $G_{13}$-, and $G_{17}$-RGDF beads and ADP activated PRP, however, even 7E3 could not completely inhibit agglutination, with the values reaching 13-25% after 30 min (data not shown).

One possible explanation for the inhibitory potency of 7E3 is that it reacts with $a_v$/IIIa VnR in addition to GPIIb/IIIa (Coller et al., 1991, *Blood* 77:75; Charo et al., 1987, *J. Biol. Chem.* 262:9935). To assess this, we studied the effect of antibody LM 609, which reacts with $a_v$/IIIa but not GPIIb/IIIa, and can block $a_v$/IIIa function (Coller et al., 1991, supra; Cheresh et al., 1987, *J. Biol. Chem.* 262:17703). Antibody 7E3 also can inhibit $a_v$/IIIa function, and preincubation of platelets with 7E3 decreases the binding of $^{125}$I-LM 609, suggesting that 7E3 and LM 609 may bind to nearby sites on $a_v$/IIIa. LM 609 alone had no effect on bead agglutination and the combination of 10E5 (anti-GPIIb/IIIa) and LM 6099 (anti-$a_v$/IIIa) was not more inhibitory than 10E5 alone. Thus, these data do not support the hypothesis that 7E3 is a more potent inhibitor than other antibodies to GPIIb/IIIa because it also reacts with $a_v$/IIIa.

PAC-1, which effectively inhibited the agglutination of $G_1$-RGDF and $G_3$-RGDF beads, had much less inhibitory activity than the other 3 antibodies when tested with the longer beads. With the $G_9$-RGDF beads, for example, it produced only 8% inhibition at 30 min (Table VI). Thus, even though convincing evidence indicates that PAC-1 binds to the RGD-binding site (Taub et al., 1989 *J. Biol. Chem.* 264:259), it was much less inhibitory than the other antibodies.

Trigramin at 3-4.5 $\mu$g/ml ($\sim$0.6 $\mu$M), which is approximately twice the concentration reported to nearly saturate platelet GPIIb/IIIa receptors (Huang et al., 1987, *J. Biol. Chem.* 262:16157), inhibited the agglutination with the shorter beads, but with the longer beads it inhibited only the early phase, such that at 30 min no inhibition was observed (Table VI). A similar inhibitory pattern was observed with the soluble RGDF peptide at $\sim$200 $\mu$g/ml ($\sim$400 $\mu$M), consistent with data for Huang et al. (supra) showing trigramin to be approximately 500-fold more potent than RGDS peptides in inhibiting fibrinogen binding to platelets.

All of the antibodies against the other integrin receptors on platelets that may recognize RGD-containing sequences within their ligands (GoH3 (anti-Ic/IIa), mAb16 (anti-Ic*/IIa), and 6F1 (anti-Ia/IIa)] did not inhibit the bead agglutination (Table VI; 3 separate experiments with each antibody). 6D1, directed against the non-integrin receptor GPIb, also had no effect on the agglutination. Although these data suggest that the interactions between these receptors and the $(G)_n$-RGDF peptides do not contribute to the observed agglutination, this conclusion must be tempered because it is possible that these antibodies bind to the receptors in a way that inhibits the binding of the macromolecular ligands to the receptors without blocking access to the RGD binding site.

9.2.6. Effect of RGD Peptides on 7E3 and 10E5 Binding

Incubation of citrated PRP with RGDS at concentrations up to 5 mM did not inhibit the initial rate of 7E3 binding; in fact, there was a consistent increase in the rate (at 5 mM a 66% increase in rate (n=2), at 2.5 mM a 63% increase in rate (n=1), and at 0.5-1 mM a 21% increase (n=4). RGDS at similar concentrations had little or no effect on 10E5 binding, decreasing the rate by 5% in one experiment and increasing it by 2% and 24% in 2 other experiments. The longer RGD peptide [LGGAKQAGDV(R)$_8$RGDV], however, consistently inhibited the initial rate of binding of both 7E3 and 10E5. The effect on 7E3 was more pronounced, with increasing concentrations of the peptide showing increasing inhibition of the initial rate of 7E3 binding up to a maximum of $\sim$73% inhibition (n=2) at 20 $\mu$M. Concentrations of peptide much higher than this (80 $\mu$M-1.67 mM) failed to increase the inhibition significantly (76%; n=8). Concentrations of the peptide up to 20 $\mu$M caused progressively greater inhibition of the initial rate of 10E5 binding to platelets, plateauing at 43% inhibition; as with 7E3, further increases in peptide concentration failed to increase the inhibition (80 $\mu$M-1.67 mM=46%; n=4).

9.3. Discussion

The interaction of the RGD sequences contained in adhesive glycoproteins with receptors on the platelet surface is thought to be crucial to normal platelet function. In the present study, we have used immobilized RGD peptides of varying lengths as structural probes of the platelet receptor(s) that mediate these interactions. We found that the shortest immobilized peptide ($G_1$-RGDF) reacted minimally with either unactivated or activated platelets in PRP, whereas the long peptides ($\geq G_9$-RGDF) interacted well with both unactivated and activated platelets, although the latter showed brisker interactions. In addition, the interactions with these longer peptides could induce the platelet release reaction, perhaps by causing receptor clustering. Inhibition of platelet activation with PGE$_1$ abolished the interaction of platelets with the beads containing the shorter peptides, but only partially inhibited the interaction of platelets with beads coated with the longer peptides. Peptides of intermediate size ($G_3$-RGDF) demonstrated the greatest sensitivity to the platelet's activation state, with virtually no interaction with platelets pretreated with PGE$_1$, slow and incomplete interaction with native platelets, and brisk and extensive interaction with ADP-activated platelets.

In contrast to the enhanced ability of the longer immobilized peptides to interact with platelets, the longer peptides in solution were less potent than the shorter ones in inhibiting the interaction between platelets and fibrinogen-coated beads. This indicates that the immobilized longer peptides do not show enhanced interaction with platelets as a result of an intrinsic affinity advantage conferred by the increased number of glycine residues; in fact, they had to overcome an intrinsic disadvantage with regard to affinity. Differences in peptide density on the beads also cannot account for the observed differences because the peptides were all immobilized at approximately the same density and dilutional studies indicated little effect of minor differences in peptide density. It is most likely, therefore, that the longer peptides were more effective because they could more easily gain access to the RGD binding sites in the receptors. Both the increased length and increased flexibility of the longer peptides could contribute to this enhanced ability to interact with the receptors.

The minimal ability of the shortest peptides to interact with platelets under any conditions indicates that the RGD binding sites may be recessed from the surface of the receptors by at least several angstroms. The gradient of increased interactions as the peptide length increased suggests that the RGD binding sites may be arrayed at various depths, either because the receptors themselves are at variable distances from the platelet surface or because the RGD binding sites are variably recessed in the receptors. Since the increase in reactivity was most dramatic between the $G_3$-RGDF and $G_7$-RGDF beads, and since there was very little increase in platelet reactivity after the peptide length was increased beyond 9 glycine residues, it is likely that most of the receptors lie within reach of the $G_3$-RGDF and $G_9$-RGDF peptides. To estimate the maximum lengths this range of peptides represents, we assume that the glycines adopt an extended conformation with 3.5 Å per glycine residue rather than an alpha-helical conformation in which case the glycines would be only 1.55 Å apart. We conclude, therefore, that the majority of RGD binding sites can be reached by peptides that extend out ~11.32 Å from the surface of the bead. Since not even minor increases in agglutination occurred with beads containing peptides longer than $G_{13}$-RGDF, we conclude that virtually all of the receptors can be reached by peptides that extend out ~46 Å from the surface of the bead.

The increased response after ADP-activation indicates that activation either causes the RGD binding sites to move closer to the platelet surface or increases the affinity of the receptor for the RGD peptides, perhaps by decreasing steric hindrance. One could visualize the latter process as either the opening up of an overlying constricting region or the straightening of an otherwise tortuous path to the binding site. The reduced agglutination response produced by PGE1 suggests either that it causes the RGD binding sites to become more recessed or to have lower affinity, perhaps as a result of greater steric hindrance. It is important to emphasize, however, that even with PGE$_1$ pretreatment, the longer beads were able to produce substantial agglutination. One possible explanation is that even under maximal inhibition by an agent such as PGE$_1$ that increases platelet cAMP, the receptors are in a dynamic equilibrium between conformations that can interact with RGD-containing ligands and others that cannot. The binding of a platelet via a receptor in the proper conformation to an RGD peptide on a bead would then allow the platelet to linger at the bead surface while additional receptors transiently adopt the proper conformation. Since the density of RGD peptides is so high, it is very likely that the receptor will find an RGD peptide to interact with even if the length of time the receptor stays in the proper conformation is brief. In this way, each interaction makes the platelet linger longer, facilitating additional interactions and encouraging the process to continue to full agglutination. Alternatively, or additionally, the length and flexibility of the longer peptides may allow them, with sufficient time, to insinuate themselves into the RGD binding sites of otherwise inaccessible receptors. The extraordinarily high density of peptides on the beads would also favor even such low affinity interactions.

10. EXAMPLE: A MONCLONAL ANTIBODY COUPLED TO ERYTHROCYTES

As described supra in Section 5.3, various targeting molecules can be coupled to erythrocytes, to produce targeted erythrocytes, specifically targeted carrier erythrocytes. The present Example demonstrates targeting of erythrocytes to platelets by coupling a monoclonal antibody to the erythrocytes.

10.1. MATERIAL AND METHODS

10.1.1. Preparation of Erythrocytes

Whole blood was collected into a tube containing 1.2 ml of CPD-A1 anticoagulant for a final volume 10 ml. The blood was centrifuged at 700×g for 3.5 min at 22° C. The platelet-rich plasma (PRP) was removed and centrifuged at 1700×g for 10 min at 22° C. The buffy coat and platelet-poor plasma (PPP) were removed, leaving 2 ml of erythrocytes. The erythrocytes were washed three times in Buffer C (140 mM NaCl, 5 mM KCL, 10mM NaPO4, and 10 mM glucose, pH 7.4), and suspended in buffer C at a 10% hematocrit.

10.1.2. Monoclonal Antibody 10E5

A 1.1 mg/ml solution of platelet glycoprotein GPIIb-/IIIa-specific monoclonal antibody 10E5 was prepared (see Sections 8 and 9, supra). To approximately 1 ml of the 10E5 solution was added 10 μl of $^{125}$I-labeled 10E5 antibody (21 μg/ml). The cold and radiolabelled 10E5 antibody solution was dialyzed using 12,000–14,000 molecular weight cut-off dialysis tubing. Buffer C was degassed with N$_2$ bubbling and equilibrated with 10 ml of 10-DG chromatography support (BioRad Econopac). The 10E5 was reduced (into a variety of forms including a pair of heavy chain-light chain univalent molecules) by adding 1 μl (about 14 mM) of 2-mercaptoethanol and incubating at 22° C. for 60 min. The reduced 10E5 was chromatographed on the 10-DG column eluted with Buffer C. Twenty fractions of 0.5 ml each were collected. Fractions #5–8 (2.2 ml) were radioactive and contained 0.53 mg of antibody (1.77×10$^5$ cpm). From these pooled fractions, 75 μl was removed for gel electrophoresis and Ellman's assay.

10.1.3. Coupling of Monoclonal Antibody to Erythrocytes

Three ml of erythrocytes (10% hematocrit) were centrifuged at 430×g for 4 min at 22° C. The pellet was resuspended to 30% hematocrit (1 ml) in Buffer C. To the erythrocytes was added 0.5 mg of freshly prepared 10 mg/ml mal-sac-HNSA in 50 μl of Buffer C. The reaction mixture was rocked for 120 min at 22° C., then washed four times in Buffer C and suspended to 1 ml in Buffer C. A 250 μl aliquot of the erythrocytes was then reacted with 0.53 mg (2.1 ml) of reduced 10E5 antibody for 30 min at 22° C.; the reaction mixture was overlayed with N$_2$.

Control erythrocytes coupled with mal-sac-HNSA were reacted with 2.1 ml of buffer C (no antibody) for 30 min at 22° C.

After reacting with 10E5 or buffer alone, cells were centrifuged 4 min at 430×g at 22° C. The supernatant was removed and stored frozen. The cells were washed three times with Buffer C, and the radioactivity determined. Calculations based on the specific activity of the 10E5 antibody indicated that approximately 1,360 antibody molecules bound per erythrocyte.

10.1.4. Activity Assays

Platelet co-agglutination assays were performed. One hundred μl of erythrocytes (10% hematocrit; 10E5 conjugated, mal-sac-HNSA controls and unmodified controls) were mixed and incubated for 10 min. The mixed cells were rotated for 8 min and microscopic cell association of the fresh samples was immediately determined using a 400× phase contrast microscope. In addition, blood smears were prepared, stained, and viewed microscopically at 1000× using an oil immersion lens.

Microscopic examination clearly differentiated between the 10E5-conjugated erythrocytes, which interacted with platelets, and the mal-sac-conjugated erythrocytes, which did not.

To demonstrate that the association of 10E5 conjugated erythrocytes with platelets was specific, the co-aggregation assay was run in the presence of soluble 10E5 antibody. Microscopic examination of the samples revealed that the platelets, when preincubated with soluble 10E5, did not associate with the 10E5-conjugated erythrocytes, whereas, in the absence of soluble 10E5, platelets again showed the interaction with the 10E5-conjugated erythrocytes.

10.2. Discussion

These results clearly indicate that erythrocytes can be targeted to a specific cell by conjugation with a targeting molecule. In this case, the targeting molecule was reduced univalent monoclonal antibody 10E5, which is specific for the glycoprotein GPIIb/IIIa on platelets.

The present invention is not to be limited in scope by the specific embodiments described herein since such embodiments are intended as but single illustrations of one aspect of the invention and any embodiments which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various references are cited herein, the disclosures of which are incorporated by reference herein in their entireties.

What is claimed is:

1. A method for preparing a targeted carrier erythrocyte comprising
   (a) causing an erythrocyte to release its intracellular contents;
   (b) introducing a material into the erythrocyte produced in step (a);
   (c) substantially resealing the membrane of the erythrocyte produced in step (b);
   (d) conjugating a polyfunctional biocompatible molecule to the erythrocyte such that a covalent bond is formed between a first functional group on the polyfunctional biocompatible molecule and the erythrocyte; and
   (e) binding the polyfunctional biocompatible molecule to a polypeptide having the formula $R_1$-Arg-Gly-Asp-$R_2$ such that a covalent bond is formed between a second functional group of the polyfunctional biocompatible molecule and the polypeptide, in which $R_1$ represents an amino acid or a sequence of more than one amino acid; and $R_2$ represents OH, an amino acid or the amide thereof, or a sequence of more than one amino acid;
   in which the targeted carrier thrombo-erythrocyte is characterized by the ability to bind to platelets.

2. The method according to claim 1 which further comprises conjugating the erythrocyte to a monoclonal antibody or antigen binding fragment thereof which specifically binds to a platelet antigen.

3. The method according to claim 2 in which the platelet antigen is GPIIb/IIIa, the polyfunctional molecule is the N-maleimido-6-aminocaproyl ester of 1-hydroxy-2-nitrobenzene-4-sulfonic acid sodium salt, and the polypeptide is acetyl-Cys-Gly-Gly-Arg-Gly-Asp-Phe-amide.

4. A targeted carrier erythrocyte comprising:
   (a) a resealed erythrocyte ghost containing within it a label;
   (b) a first targeting molecule conjugated to the erythrocyte ghost via a covalent bond, wherein said first targeting molecule is a monoclonal antibody, or antigen binding fragment thereof, which binds to a platelet antigen; and
   (c) a second targeting molecule conjugated to the erythrocyte ghost via a covalent bond, wherein said second targeting molecule is a polypeptide comprising the sequence Arg-Gly-Asp.

5. A targeted carrier erythrocyte comprising a resealed erythrocyte ghost containing within it a label, in which the erythrocyte ghost is covalently bonded to a polyfunctional biocompatible molecule via a first functional group on the polyfunctional molecule; and the polyfunctional molecule is covalently bonded via a second functional group on the polyfunctional molecule to a polypeptide having the formula:

$R_1$-Arg-Gly-Asp-$R_2$ in which $R_1$ represents an amino acid or a sequence of more than one amino acid, and $R_1$ is covalently bonded to a second functional group of the polyfunctional molecule; and $R_2$ represents OH, an amino acid or the amide thereof, or a sequence of more than one amino acid; and in which the targeted carrier erythrocyte is characterized by the ability to bind to platelets.

6. The targeted carrier erythrocyte of claim 5 in which the polyfunctional molecule is the N-maleimido-6-aminocaproyl ester of 1-hydroxy-2-nitrobenzene-4-sulfonic acid sodium salt, and the polypeptide is acetyl-Cys-Gly-Gly-Arg-Gly-Asp-Phe-amide.

7. A targeted carrier erythrocyte comprising a resealed erythrocyte ghost containing within it a label, in which the erythrocyte ghost is covalently bonded to a polyfunctional biocompatible molecule via a first functional group on the polyfunctional molecule; and the polyfunctional molecule is covalently bonded via a second functional group on the polyfunctional molecule to a polypeptide having the formula:

$XY(Z)_n$-Arg-Gly-Asp-R in which X, Y and Z independently represent an amino acid, and X is covalently bonded to a second functional group of the polyfunctional molecule; n represents 0 or 1; and R represents OH, an amino acid or the amide thereof, or a sequence of more than one amino acid; and in which the targeted carrier erythrocyte is characterized by the ability to bind to platelets.

8. The targeted carrier erythrocyte of claim 5 or 7 in which the label is selected from the group consisting of a radionuclide, a heavy metal, and a magnetic resonance imaging agent.

9. A targeted carrier erythrocyte comprising a resealed erythrocyte ghost containing within it a biologically active agent, in which the erythrocyte ghost is covalently bonded to a polyfunctional biocompatible molecule via a first functional group on the polyfunctional molecule; and the polyfunctional molecule is covalently bonded via a second functional group on the polyfunctional molecule to a polypeptide having the formula:

$XY(Z)_n$-Arg-Gly-Asp-R in which X, Y and Z independently represent an amino acid, and X is covalently bonded to a second functional group of the polyfunctional molecule; n represents 0 or 1; and R represents OH, an amino acid or the amide thereof, or a sequence of more than one amino acid; and in which the targeted carrier erythrocyte is characterized by the ability to bind to platelets.

10. The targeted carrier erythrocyte of claim 9 in which the biologically active agent is a thrombolytic agent.

11. A targeted carrier erythrocyte comprising:
(a) a resealed erythrocyte ghost containing within it a biologically active agent;
(b) a first targeting molecule conjugated to the erythrocyte ghost via a covalent bond, wherein said first targeting molecule is a monoclonal antibody, or antigen binding fragment thereof, which binds to a platelet antigen; and
(c) a second targeting molecule conjugated to the erythrocyte ghost via a covalent bond, wherein said second targeting molecule is a polypeptide comprising the sequence Arg-Gly-Asp.

12. The targeted carrier erythrocyte of claim 11 in which the biologically active agent is a thrombolytic agent.

13. A targeted carrier erythrocyte comprising a resealed erythrocyte ghost containing within it a biologically active agent, in which the erythrocyte ghost is covalently bonded to a polyfunctional biocompatible molecule via a first functional group on the polyfunctional molecule; and the polyfunctional molecule is covalently bonded via a second functional group on the polyfunctional molecule to a polypeptide having the formula:

$R_1$-Arg-Gly-Asp-$R_2$ in which $R_1$ represents an amino acid or a sequence of more than one amino acid, and $R_1$ is covalently bonded to a second functional group of the polyfunctional molecule; and $R_2$ represents OH, an amino acid or the amide thereof, or a sequence of more than one amino acid; and in which the targeted carrier erythrocyte is characterized by the ability to bind to platelets.

14. The targeted carrier erythrocyte of claim 13 in which the polyfunctional molecule is the N-maleimido-6-aminocaproyl ester of 1-hydroxy-2-nitrobenzene-4-sulfonic acid sodium salt, and the polypeptide is acetyl-Cys-Gly-Gly-Arg-Gly-Asp-Phe-amide.

15. The targeted carrier erythrocyte of claim 14 in which the biologically active agent is a thrombolytic agent.

16. The targeted carrier erythrocyte of claim 13 in which the biologically active agent is a thrombolytic agent.

17. The targeted carrier erythrocyte of claim 13, 16 or 15 which further comprises a second molecule conjugated to the erythrocyte ghost via a covalent bond, said second molecule being a targeting molecule which specifically binds to a platelet.

18. The targeted carrier erythrocyte of claim 17 in which said second molecule is a monoclonal antibody or antigen binding fragment thereof.

19. The targeted carrier erythrocyte of claim 18 in which the monoclonal antibody or antigen binding fragment binds to GPIIb/IIIa.

20. A pharmaceutical composition comprising the targeted carrier erythrocyte of claim 11, 12, 13, or 14, in which the biologically active agent is a therapeutic agent; and a pharmaceutically acceptable carrier or excipient.

* * * * *